(12) United States Patent
Garrison et al.

(10) Patent No.: US 12,728,229 B2
(45) Date of Patent: Sep. 8, 2026

(54) RAPID ASPIRATION THROMBECTOMY SYSTEM AND METHOD

(71) Applicant: Route 92 Medical, Inc., San Mateo, CA (US)

(72) Inventors: Michi E. Garrison, San Mateo, CA (US); Tony M. Chou, San Mateo, CA (US); Scott D. Wilson, San Mateo, CA (US)

(73) Assignee: Route 92 Medical, Inc., West Jordan, UT (US)

( * ) Notice: Subject to any disclaimer, the term of this patent is extended or adjusted under 35 U.S.C. 154(b) by 96 days.

(21) Appl. No.: 18/369,695

(22) Filed: Sep. 18, 2023

(65) Prior Publication Data

US 2024/0009425 A1 Jan. 11, 2024

Related U.S. Application Data

(63) Continuation of application No. 16/596,535, filed on Oct. 8, 2019, now abandoned, which is a continuation (Continued)

(51) Int. Cl.

*A61M 25/01* (2006.01)
*A61B 17/22* (2006.01)

(Continued)

(52) U.S. Cl.

CPC ......... *A61M 25/0102* (2013.01); *A61B 17/22* (2013.01); *A61B 17/221* (2013.01);

(Continued)

(58) Field of Classification Search

CPC .......... A61M 25/0054; A61M 25/0067; A61M 25/008; A61M 25/0097; A61M 25/0102;

(Continued)

(56) References Cited

U.S. PATENT DOCUMENTS 2,623,520 A 12/1952 Bamford, Jr. et al.
2,730,101 A 1/1956 Hoffman (Continued)

FOREIGN PATENT DOCUMENTS

CN 101121055 A 2/2008
CN 101588835 A 11/2009

(Continued)

OTHER PUBLICATIONS

U.S. Appl. No. 16/890,962, filed Jun. 2, 2020, US 2020-0289136.

(Continued)

*Primary Examiner* — Kami A Bosworth
(74) *Attorney, Agent, or Firm* — Mintz Levin Cohn Ferris Glovsky and Popeo, P.C.

(57) ABSTRACT

An intravascular access system for facilitation of intraluminal medical procedures within the neurovasculature through an access sheath. The system includes an aspiration or support catheter having a flexible, distal luminal portion having an inner diameter defining a lumen extending between a proximal opening at a proximal end of the luminal portion and a distal opening at a distal end of the luminal portion. The catheter has a rigid spine coupled to at least the proximal end of the luminal portion and extending proximally therefrom. The system includes a dilator having a flexible, distal dilator portion sized to be received within the lumen of the luminal portion. Associated systems, devices, and methods of use are also described.

14 Claims, 19 Drawing Sheets

Related U.S. Application Data of application No. 15/856,979, filed on Dec. 28, 2017, now Pat. No. 10,456,555, which is a continuation of application No. 15/805,673, filed on Nov. 7, 2017, now Pat. No. 10,485,952, which is a continuation of application No. 15/015,799, filed on Feb. 4, 2016, now Pat. No. 9,820,761.

(60) Provisional application No. 62/142,637, filed on Apr. 3, 2015, provisional application No. 62/111,841, filed on Feb. 4, 2015.

(51) Int. Cl.

| | |
|---|---|
| ***A61B 17/221*** | (2006.01) |
| ***A61M 1/00*** | (2006.01) |
| ***A61M 5/00*** | (2006.01) |
| ***A61M 25/00*** | (2006.01) |
| ***A61M 25/06*** | (2006.01) |
| ***A61M 25/10*** | (2013.01) |
| ***A61M 29/00*** | (2006.01) |

(52) U.S. Cl.

CPC .............. *A61M 1/84* (2021.05); *A61M 5/007* (2013.01); *A61M 25/0043* (2013.01); *A61M 25/0054* (2013.01); *A61M 25/0067* (2013.01); *A61M 25/01* (2013.01); *A61M 25/0108* (2013.01); *A61M 25/0662* (2013.01); *A61M 25/10* (2013.01); *A61M 29/00* (2013.01); *A61B 2017/22038* (2013.01); *A61B 2017/22079* (2013.01); *A61B 2017/2212* (2013.01); *A61B 2217/005* (2013.01); *A61M 2025/0019* (2013.01); *A61M 2025/0042* (2013.01); *A61M 25/0074* (2013.01); *A61M 25/0097* (2013.01); *A61M 2025/0175* (2013.01); *A61M 2025/0681* (2013.01); *A61M 2025/1084* (2013.01); *A61M 2210/0693* (2013.01); *A61M 2210/12* (2013.01)

(58) Field of Classification Search

CPC .......... A61M 25/0108; A61M 25/0141; A61M 2025/0004; A61M 2025/0006; A61M 2025/0042; A61M 2025/0081; A61M 2025/0681; A61M 2210/0693

See application file for complete search history.

(56) References Cited

U.S. PATENT DOCUMENTS

| | | | |
|---|---|---|---|
| 3,589,368 | A | 6/1971 | Jackson et al. |
| 3,612,050 | A | 10/1971 | Sheridan |
| 3,631,848 | A | 1/1972 | Muller |
| 3,949,757 | A | 4/1976 | Sabel |
| 3,996,938 | A | 12/1976 | Clark, III |
| 4,013,080 | A | 3/1977 | Froning |
| 4,020,829 | A | 5/1977 | Willson et al. |
| 4,033,331 | A | 7/1977 | Guss et al. |
| 4,174,715 | A | 11/1979 | Hasson |
| 4,319,580 | A | 3/1982 | Colley et al. |
| 4,323,071 | A | 4/1982 | Simpson et al. |
| 4,406,656 | A | 9/1983 | Hattler et al. |
| 4,571,240 | A | 2/1986 | Samson et al. |
| 4,610,662 | A | 9/1986 | Weikl et al. |
| 4,619,263 | A | 10/1986 | Frisbie et al. |
| 4,676,249 | A | 6/1987 | Arenas et al. |
| 4,723,549 | A | 2/1988 | Wholey et al. |
| 4,728,319 | A | 3/1988 | Masch |
| 4,739,768 | A | 4/1988 | Engelson |
| 4,762,128 | A | 8/1988 | Rosenbluth |
| 4,771,777 | A | 9/1988 | Horzewski et al. |
| 4,784,636 | A | 11/1988 | Rydell |
| 4,790,812 | A | 12/1988 | Hawkins, Jr. et al. |
| 4,794,928 | A | 1/1989 | Kletschka |
| 4,795,434 | A | 1/1989 | Kujawski |
| 4,799,496 | A | 1/1989 | Hargreaves et al. |
| 4,834,709 | A | 5/1989 | Banning et al. |
| 4,840,690 | A | 6/1989 | Melinyshyn et al. |
| 4,863,431 | A | 9/1989 | Vaillancourt |
| 4,865,581 | A | 9/1989 | Lundquist et al. |
| 4,873,978 | A | 10/1989 | Ginsburg |
| 4,873,979 | A | 10/1989 | Hanna |
| 4,883,460 | A | 11/1989 | Zanetti |
| 4,887,613 | A | 12/1989 | Farr et al. |
| 4,898,575 | A | 2/1990 | Fischell et al. |
| 4,900,303 | A | 2/1990 | Lemelson |
| 4,921,478 | A | 5/1990 | Solano et al. |
| 4,921,479 | A | 5/1990 | Grayzel |
| 4,921,484 | A | 5/1990 | Hillstead |
| 4,923,462 | A | 5/1990 | Stevens |
| 4,946,440 | A | 8/1990 | Hall |
| 4,946,443 | A | 8/1990 | Hauser et al. |
| 4,994,033 | A | 2/1991 | Shockey et al. |
| 4,994,067 | A | 2/1991 | Summers |
| 4,998,919 | A | 3/1991 | Schnepp-Pesch et al. |
| 5,011,488 | A | 4/1991 | Ginsburg |
| 5,011,490 | A | 4/1991 | Fischell et al. |
| 5,053,008 | A | 10/1991 | Bajaj |
| 5,059,178 | A | 10/1991 | Ya |
| 5,102,415 | A | 4/1992 | Guenther et al. |
| 5,103,827 | A | 4/1992 | Smith |
| 5,108,419 | A | 4/1992 | Reger et al. |
| 5,135,484 | A | 8/1992 | Wright |
| 5,152,277 | A | 10/1992 | Honda et al. |
| 5,161,534 | A | 11/1992 | Berthiaume |
| 5,163,906 | A | 11/1992 | Ahmadi |
| 5,185,004 | A | 2/1993 | Lashinski |
| 5,188,621 | A | 2/1993 | Samson |
| 5,200,248 | A | 4/1993 | Thompson et al. |
| 5,207,648 | A | 5/1993 | Gross |
| 5,211,651 | A | 5/1993 | Reger et al. |
| 5,217,705 | A | 6/1993 | Reno et al. |
| 5,219,332 | A | 6/1993 | Nelson et al. |
| 5,243,997 | A | 9/1993 | Uflacker et al. |
| 5,250,060 | A | 10/1993 | Carbo et al. |
| 5,257,979 | A | 11/1993 | Jagpal |
| 5,267,960 | A | 12/1993 | Hayman et al. |
| 5,269,297 | A | 12/1993 | Weng et al. |
| 5,303,714 | A | 4/1994 | Abele et al. |
| 5,308,318 | A | 5/1994 | Plassche, Jr. |
| 5,312,338 | A | 5/1994 | Nelson et al. |
| 5,312,356 | A | 5/1994 | Engelson et al. |
| RE34,633 | E | 6/1994 | Sos et al. |
| 5,318,032 | A | 6/1994 | Lonsbury et al. |
| 5,324,262 | A | 6/1994 | Fischell et al. |
| 5,325,868 | A | 7/1994 | Kimmelstiel |
| 5,328,471 | A | 7/1994 | Slepian |
| 5,338,300 | A | 8/1994 | Cox |
| 5,352,197 | A | 10/1994 | Hammersmark et al. |
| 5,364,358 | A | 11/1994 | Hewitt et al. |
| 5,370,623 | A | 12/1994 | Kreamer |
| 5,380,284 | A | 1/1995 | Don Michael |
| 5,385,562 | A | 1/1995 | Adams et al. |
| 5,391,152 | A | 2/1995 | Patterson |
| 5,392,778 | A | 2/1995 | Horzewski |
| 5,395,383 | A | 3/1995 | Adams et al. |
| 5,413,575 | A | 5/1995 | Haenggi |
| 5,423,331 | A | 6/1995 | Wysham |
| 5,429,605 | A | 7/1995 | Richling: Bernd et al. |
| 5,437,632 | A | 8/1995 | Engelson |
| 5,438,993 | A | 8/1995 | Lynch et al. |
| 5,441,051 | A | 8/1995 | Hileman et al. |
| 5,443,454 | A | 8/1995 | Tanabe et al. |
| 5,454,788 | A | 10/1995 | Walker et al. |
| 5,454,795 | A | 10/1995 | Samson |
| 5,465,716 | A | 11/1995 | Avitall |
| 5,466,222 | A | 11/1995 | Ressemann et al. |
| 5,476,450 | A | 12/1995 | Ruggio |
| 5,484,407 | A | 1/1996 | Osypka |
| 5,484,412 | A | 1/1996 | Pierpont |
| 5,484,418 | A | 1/1996 | Quiachon et al. |
| 5,485,667 | A | 1/1996 | Kleshinski |

(56) References Cited

U.S. PATENT DOCUMENTS 5,486,193 A 1/1996 Bourne et al.
5,490,859 A 2/1996 Mische et al.
5,492,530 A 2/1996 Fischell et al.
5,496,294 A 3/1996 Hergenrother et al.
5,499,975 A 3/1996 Cope et al.
5,501,694 A 3/1996 Ressemann et al.
5,522,836 A 6/1996 Palermo
5,527,292 A 6/1996 Adams et al.
5,531,715 A 7/1996 Engelson et al.
5,533,967 A 7/1996 Imran
5,538,512 A 7/1996 Zenzon et al.
5,542,936 A 8/1996 Razi
5,542,937 A 8/1996 Chee et al.
5,546,958 A 8/1996 Thorud et al.
5,549,119 A 8/1996 Solar
5,549,601 A 8/1996 McIntyre et al.
5,549,626 A 8/1996 Miller et al.
5,558,635 A 9/1996 Cannon
5,571,122 A 11/1996 Kelly et al.
5,573,520 A 11/1996 Schwartz et al.
5,578,009 A 11/1996 Kraus et al.
5,591,194 A 1/1997 Berthiaume
5,599,307 A 2/1997 Bacher et al.
5,599,326 A 2/1997 Carter
5,603,698 A 2/1997 Roberts et al.
5,628,754 A 5/1997 Shevlin et al.
5,643,254 A 7/1997 Scheldrup et al.
5,658,263 A 8/1997 Dang et al.
5,658,264 A 8/1997 Samson
5,658,309 A 8/1997 Berthiaume et al.
5,662,622 A 9/1997 Gore et al.
5,667,499 A 9/1997 Welch et al.
5,676,659 A 10/1997 McGurk
5,682,894 A 11/1997 Orr et al.
5,693,029 A 12/1997 Leonhardt
5,695,483 A 12/1997 Samson
5,702,373 A 12/1997 Samson
5,702,439 A 12/1997 Keith et al.
5,707,376 A 1/1998 Kavteladze et al.
5,720,764 A 2/1998 Naderlinger
5,730,734 A 3/1998 Adams et al.
5,749,849 A 5/1998 Engelson
5,749,858 A 5/1998 Cramer
5,766,191 A 6/1998 Trerotola
5,776,141 A 7/1998 Klein et al.
5,776,142 A 7/1998 Gunderson
5,794,629 A 8/1998 Frazee
5,795,341 A 8/1998 Samson
5,807,327 A 9/1998 Green et al.
5,810,869 A 9/1998 Kaplan et al.
5,810,874 A 9/1998 Lefebvre
5,814,064 A 9/1998 Daniel et al.
5,817,101 A 10/1998 Fiedler
5,827,229 A 10/1998 Auth et al.
5,827,242 A 10/1998 Follmer et al.
5,833,650 A 11/1998 Imran
5,836,868 A 11/1998 Ressemann et al.
5,836,926 A 11/1998 Peterson et al.
5,836,955 A 11/1998 Buelna et al.
5,843,002 A 12/1998 Pecor et al.
5,843,051 A 12/1998 Adams et al.
5,843,103 A 12/1998 Wulfman
5,846,251 A 12/1998 Hart
5,851,189 A 12/1998 Forber
5,851,210 A 12/1998 Torossian
5,853,400 A 12/1998 Samson
5,876,367 A 3/1999 Kaganov et al.
5,876,375 A 3/1999 Penny
5,876,386 A 3/1999 Samson
5,882,329 A 3/1999 Patterson et al.
5,882,334 A 3/1999 Sepetka et al.
5,885,209 A 3/1999 Green
5,891,114 A 4/1999 Chien et al.
5,895,399 A 4/1999 Barbut et al.
5,897,567 A 4/1999 Ressemann et al.
5,899,890 A 5/1999 Chiang et al.
5,899,892 A 5/1999 Mortier et al.
5,908,407 A 6/1999 Frazee et al.
5,910,154 A 6/1999 Tsugita et al.
5,911,725 A 6/1999 Boury
5,911,734 A 6/1999 Tsugita et al.
5,913,848 A 6/1999 Luther et al.
5,916,192 A 6/1999 Nita et al.
5,916,208 A 6/1999 Luther et al.
5,921,952 A 7/1999 Desmond, III et al.
5,928,192 A 7/1999 Maahs
5,928,260 A 7/1999 Chin et al.
5,935,122 A 8/1999 Fourkas et al.
5,935,139 A 8/1999 Bates
5,938,645 A 8/1999 Gordon
5,941,869 A 8/1999 Patterson et al.
5,957,882 A 9/1999 Nita et al.
5,972,019 A 10/1999 Engelson et al.
5,976,093 A 11/1999 Jang
5,976,120 A 11/1999 Chow et al.
5,976,178 A 11/1999 Goldsteen et al.
5,997,508 A 12/1999 Lunn et al.
5,997,523 A 12/1999 Jang
5,997,557 A 12/1999 Barbut et al.
6,004,310 A 12/1999 Bardsley et al.
6,007,530 A 12/1999 Dornhofer et al.
6,010,522 A 1/2000 Barbut et al.
6,013,085 A 1/2000 Howard
6,022,336 A 2/2000 Zadno-Azizi et al.
6,022,340 A 2/2000 Sepetka et al.
6,030,349 A 2/2000 Wilson et al.
6,030,369 A 2/2000 Engelson et al.
6,033,388 A 3/2000 Nordstrom et al.
6,044,845 A 4/2000 Lewis
6,053,903 A 4/2000 Samson
6,053,904 A 4/2000 Scribner et al.
6,066,149 A 5/2000 Samson et al.
6,071,263 A 6/2000 Kirkman
6,074,357 A 6/2000 Kaganov et al.
6,074,398 A 6/2000 Leschinsky
6,077,295 A 6/2000 Limon et al.
6,090,072 A 7/2000 Kratoska et al.
6,090,118 A 7/2000 McGuckin, Jr.
6,106,530 A 8/2000 Harada
6,110,139 A 8/2000 Loubser
6,117,141 A 9/2000 Ouchi
6,120,480 A 9/2000 Zhang et al.
6,135,991 A 10/2000 Muni et al.
6,139,524 A 10/2000 Killion
6,142,958 A 11/2000 Hammarstrom et al.
6,142,987 A 11/2000 Tsugita
6,146,370 A 11/2000 Barbut
6,146,373 A 11/2000 Cragg et al.
6,146,396 A 11/2000 Konya et al.
6,146,415 A 11/2000 Fitz
6,152,909 A 11/2000 Bagaoisan et al.
6,152,912 A 11/2000 Jansen et al.
6,156,005 A 12/2000 Theron
6,159,195 A 12/2000 Ha et al.
6,159,230 A 12/2000 Samuels
6,161,547 A 12/2000 Barbut
6,165,163 A 12/2000 Chien et al.
6,165,167 A 12/2000 Delaloye
6,165,199 A 12/2000 Barbut
6,168,579 B1 1/2001 Tsugita
6,171,295 B1 1/2001 Garabedian et al.
6,171,296 B1 1/2001 Chow
6,176,844 B1 1/2001 Lee
6,197,016 B1 3/2001 Fourkas et al.
6,203,561 B1 3/2001 Ramee et al.
6,206,868 B1 3/2001 Parodi
6,210,370 B1 4/2001 Chi-Sing et al.
6,221,038 B1 4/2001 Brisken
6,221,049 B1 4/2001 Selmon et al.
6,228,046 B1 5/2001 Brisken
6,228,052 B1 5/2001 Pohndorf
6,234,971 B1 5/2001 Jang
6,238,402 B1 5/2001 Sullivan, III et al.
6,238,412 B1 5/2001 Dubrul et al.

(56) References Cited

U.S. PATENT DOCUMENTS 6,238,430 B1 5/2001 Klumb et al.
6,240,231 B1 5/2001 Ferrera et al.
6,254,628 B1 7/2001 Wallace et al.
6,258,052 B1 7/2001 Milo
6,258,080 B1 7/2001 Samson
6,258,115 B1 7/2001 Dubrul
6,270,477 B1 8/2001 Bagaoisan et al.
6,277,115 B1 8/2001 Saadat
6,277,139 B1 8/2001 Levinson et al.
6,287,319 B1 9/2001 Aboul-Hosn et al.
6,295,989 B1 10/2001 Connors, III
6,295,990 B1 10/2001 Lewis et al.
6,306,106 B1 10/2001 Boyle
6,306,163 B1 10/2001 Fitz
6,309,379 B1 10/2001 Willard et al.
6,346,116 B1 2/2002 Brooks et al.
6,355,027 B1 3/2002 Le et al.
6,361,545 B1 3/2002 Macoviak et al.
6,364,894 B1 4/2002 Healy et al.
6,364,900 B1 4/2002 Heuser
6,368,316 B1 4/2002 Jansen et al.
6,368,338 B1 4/2002 Konya et al.
6,368,344 B1 4/2002 Fitz
6,368,355 B1 4/2002 Uflacker
6,379,325 B1 4/2002 Benett et al.
6,383,172 B1 5/2002 Barbut
6,391,044 B1 5/2002 Yadav et al.
6,394,976 B1 5/2002 Winston et al.
6,413,235 B1 7/2002 Parodi
6,423,032 B2 7/2002 Parodi
6,423,086 B1 7/2002 Barbut et al.
6,428,531 B1 8/2002 Visuri et al.
6,435,189 B1 8/2002 Lewis et al.
6,436,087 B1 8/2002 Lewis et al.
6,451,005 B1 9/2002 Saitou et al.
6,454,741 B1 9/2002 Muni et al.
6,454,775 B1 9/2002 Demarais et al.
6,458,151 B1 10/2002 Saltiel
6,464,664 B1 10/2002 Jonkman et al.
6,468,219 B1 10/2002 Njemanze
6,475,195 B1 11/2002 Voda
6,475,244 B2 11/2002 Herweck et al.
6,481,439 B1 11/2002 Lewis et al.
6,482,172 B1 11/2002 Thramann
6,482,217 B1 11/2002 Pintor et al.
6,485,466 B2 11/2002 Hamilton
6,485,500 B1 11/2002 Kokish et al.
6,485,501 B1 11/2002 Green
6,508,824 B1 1/2003 Flaherty et al.
6,511,470 B1 1/2003 Hamilton
6,511,471 B2 1/2003 Rosenman et al.
6,514,261 B1 2/2003 Randall et al.
6,514,273 B1 2/2003 Voss et al.
6,517,520 B2 2/2003 Chang et al.
6,524,303 B1 2/2003 Garibaldi
6,527,746 B1 3/2003 Oslund et al.
6,533,770 B1 3/2003 Lepulu et al.
6,533,800 B1 3/2003 Barbut
6,537,241 B1 3/2003 Odland
6,537,295 B2 3/2003 Petersen
6,540,712 B1 4/2003 Parodi et al.
6,540,768 B1 4/2003 Diaz et al.
6,544,276 B1 4/2003 Azizi
6,549,800 B1 4/2003 Atalar et al.
6,551,268 B1 4/2003 Kaganov et al.
6,551,273 B1 4/2003 Olson et al.
6,551,302 B1 4/2003 Rosinko et al.
6,554,820 B1 4/2003 Wendlandt et al.
6,554,827 B2 4/2003 Chandrasekaran et al.
6,554,849 B1 4/2003 Jones et al.
6,555,057 B1 4/2003 Barbut et al.
6,558,377 B2 5/2003 Lee et al.
6,558,405 B1 5/2003 McInnes
6,562,049 B1 5/2003 Norlander et al.
6,562,052 B2 5/2003 Nobles et al.
6,569,148 B2 5/2003 Bagaoisan et al.
6,579,246 B2 6/2003 Jacobsen et al.
6,579,260 B2 6/2003 Maki et al.
6,579,264 B1 6/2003 Rossi
6,579,484 B1 6/2003 Tiernan et al.
6,582,390 B1 6/2003 Sanderson
6,582,396 B1 6/2003 Parodi
6,582,440 B1 6/2003 Brumbach
6,582,448 B1 6/2003 Boyle et al.
6,589,262 B1 7/2003 Honebrink et al.
6,592,616 B1 7/2003 Stack et al.
6,595,953 B1 7/2003 Coppi et al.
6,595,980 B1 7/2003 Barbut
6,595,989 B1 7/2003 Schaer
6,596,011 B2 7/2003 Johnson et al.
6,605,074 B2 8/2003 Zadno-Azizi et al.
6,610,077 B1 8/2003 Hancock et al.
6,612,999 B2 9/2003 Brennan et al.
6,616,681 B2 9/2003 Hanson et al.
6,620,148 B1 9/2003 Tsugita
6,622,367 B1 9/2003 Bolduc et al.
6,623,471 B1 9/2003 Barbut
6,623,491 B2 9/2003 Thompson
6,623,518 B2 9/2003 Thompson et al.
6,626,886 B1 9/2003 Barbut
6,632,236 B2 10/2003 Hogendijk
6,635,070 B2 10/2003 Leeflang et al.
6,638,243 B2 10/2003 Kupiecki
6,638,245 B2 10/2003 Miller et al.
6,641,573 B1 11/2003 Parodi
6,645,160 B1 11/2003 Heesch
6,645,222 B1 11/2003 Parodi et al.
6,652,480 B1 11/2003 Imran et al.
6,656,152 B2 12/2003 Putz
6,663,650 B2 12/2003 Sepetka et al.
6,663,652 B2 12/2003 Daniel et al.
6,673,025 B1 1/2004 Richardson et al.
6,676,637 B1 1/2004 Bonnette et al.
6,679,893 B1 1/2004 Tran
6,682,505 B2 1/2004 Bates et al.
6,685,672 B1 2/2004 Forman
6,685,722 B1 2/2004 Rosenbluth et al.
6,689,144 B2 2/2004 Gerberding
6,692,473 B2 2/2004 St. Cyr et al.
6,695,858 B1 2/2004 Dubrul et al.
6,695,865 B2 2/2004 Boyle et al.
6,702,782 B2 3/2004 Miller et al.
6,702,834 B1 3/2004 Boylan et al.
6,706,055 B2 3/2004 Douk et al.
6,711,436 B1 3/2004 Duhaylongsod
6,716,183 B2 4/2004 Clayman et al.
6,719,717 B1 4/2004 Johnson et al.
6,723,064 B2 4/2004 Babaev
6,726,675 B1 4/2004 Beyar
6,730,104 B1 5/2004 Sepetka et al.
6,733,517 B1 5/2004 Collins
6,740,104 B1 5/2004 Solar et al.
6,749,627 B2 6/2004 Thompson et al.
6,755,803 B1 6/2004 Le et al.
6,755,812 B2 6/2004 Peterson et al.
6,755,847 B2 6/2004 Eskuri
6,758,854 B1 7/2004 Butler et al.
6,761,708 B1 7/2004 Chiu et al.
6,764,464 B2 7/2004 McGuckin, Jr. et al.
6,773,448 B2 8/2004 Kusleika et al.
6,790,204 B2 9/2004 Zadno-Azizi et al.
6,805,684 B2 10/2004 Bonnette et al.
6,805,692 B2 10/2004 Muni et al.
6,824,545 B2 11/2004 Sepetka et al.
6,824,550 B1 11/2004 Noriega et al.
6,824,553 B1 11/2004 Samson et al.
6,827,730 B1 12/2004 Leschinsky
6,837,881 B1 1/2005 Barbut
6,840,949 B2 1/2005 Barbut
6,849,068 B1 2/2005 Bagaoisan et al.
6,855,136 B2 2/2005 Dorros et al.
6,866,669 B2 3/2005 Buzzard et al.
6,878,151 B2 4/2005 Carrison et al.
6,879,854 B2 4/2005 Windheuser et al.

(56) References Cited

U.S. PATENT DOCUMENTS 6,884,235 B2 4/2005 McGuckin, Jr. et al.
6,902,540 B2 6/2005 Dorros et al.
6,905,490 B2 6/2005 Parodi
6,905,505 B2 6/2005 Nash et al.
6,908,474 B2 6/2005 Hogendijk et al.
6,911,036 B2 6/2005 Douk et al.
6,926,658 B2 8/2005 Farnan
6,929,632 B2 8/2005 Nita et al.
6,929,634 B2 8/2005 Dorros et al.
6,936,060 B2 8/2005 Hogendijk et al.
6,945,956 B2 9/2005 Waldhauser et al.
6,949,104 B2 9/2005 Griffis et al.
6,951,570 B2 10/2005 Linder et al.
6,958,059 B2 10/2005 Zadno-Azizi
6,960,189 B2 11/2005 Bates et al.
6,969,395 B2 11/2005 Eskuri
6,972,030 B2 12/2005 Lee et al.
6,977,068 B1 12/2005 Nair et al.
6,991,642 B2 1/2006 Petersen
7,001,400 B1 2/2006 Modesitt et al.
7,004,924 B1 2/2006 Brugger et al.
7,004,931 B2 2/2006 Hogendijk
7,004,952 B2 2/2006 Nobles et al.
7,022,100 B1 4/2006 Aboul-Hosn et al.
7,029,488 B2 4/2006 Schonholz et al.
7,033,325 B1 4/2006 Sullivan
7,033,336 B2 4/2006 Hogendijk
7,033,344 B2 4/2006 Imran
7,037,267 B1 5/2006 Lipson et al.
7,048,758 B2 5/2006 Boyle et al.
7,052,500 B2 5/2006 Bashiri et al.
7,056,328 B2 6/2006 Arnott
7,063,714 B2 6/2006 Dorros et al.
7,083,594 B2 8/2006 Coppi
7,104,979 B2 9/2006 Jansen et al.
7,108,677 B2 9/2006 Courtney et al.
7,115,134 B2 10/2006 Chambers
7,115,138 B2 10/2006 Renati et al.
7,118,539 B2 10/2006 Vrba et al.
7,144,386 B2 12/2006 Korkor et al.
7,150,712 B2 12/2006 Buehlmann et al.
7,152,605 B2 12/2006 Khairkhahan et al.
7,166,088 B2 1/2007 Heuser
7,166,120 B2 1/2007 Kusleika
7,169,165 B2 1/2007 Belef et al.
7,172,621 B2 2/2007 Theron
7,172,623 B2 2/2007 Hansen et al.
7,220,246 B2 5/2007 Raulerson et al.
7,220,271 B2 5/2007 Clubb et al.
7,223,253 B2 5/2007 Hogendijk
7,229,431 B2 6/2007 Houser et al.
7,229,463 B2 6/2007 Sutton et al.
7,229,464 B2 6/2007 Hanson et al.
7,232,452 B2 6/2007 Adams et al.
7,235,061 B2 6/2007 Tsugita
7,242,977 B2 7/2007 Partridge et al.
7,250,042 B2 7/2007 Kataishi et al.
7,285,126 B2 10/2007 Sepetka et al.
7,306,585 B2 12/2007 Ross
7,309,334 B2 12/2007 von Hoffmann
7,316,678 B2 1/2008 Nash et al.
7,329,278 B2 2/2008 Seguin et al.
7,367,982 B2 5/2008 Nash et al.
7,374,560 B2 5/2008 Ressemann et al.
7,374,561 B2 5/2008 Barbut
7,374,564 B2 5/2008 Brown
7,381,200 B2 6/2008 Katoh et al.
7,384,412 B2 6/2008 Coppi
7,402,151 B2 7/2008 Rosenman et al.
7,413,561 B2 8/2008 Raulerson et al.
7,422,579 B2 9/2008 Wahr et al.
7,449,010 B1 11/2008 Hayase et al.
7,458,980 B2 12/2008 Barbut
7,473,271 B2 1/2009 Gunderson
7,476,232 B2 1/2009 Deal
7,497,844 B2 3/2009 Spear et al.
7,507,229 B2 3/2009 Hewitt et al.
7,524,303 B1 4/2009 Don Michael et al.
7,534,250 B2 5/2009 Schaeffer et al.
7,537,568 B2 5/2009 Moehring
7,549,974 B2 6/2009 Nayak
7,558,622 B2 7/2009 Tran
7,604,612 B2 10/2009 Ressemann et al.
7,615,042 B2 11/2009 Beyar et al.
7,625,207 B2 12/2009 Hershey et al.
7,691,121 B2 4/2010 Rosenbluth et al.
7,717,934 B2 5/2010 Kusleika
7,731,683 B2 6/2010 Jang et al.
7,736,355 B2 6/2010 Itou et al.
7,766,049 B2 8/2010 Miller et al.
7,766,820 B2 8/2010 Core
7,771,358 B2 8/2010 Moehring et al.
7,785,286 B2 8/2010 Magnin et al.
7,803,136 B2 9/2010 Schatz
7,806,906 B2 10/2010 Don Michael
7,815,626 B1 10/2010 McFadden et al.
7,827,656 B2 11/2010 Schweikert
7,837,692 B2 11/2010 Mulholland et al.
7,842,055 B2 11/2010 Pintor et al.
7,842,065 B2 11/2010 Belef et al.
7,850,642 B2 12/2010 Moll et al.
7,850,654 B2 12/2010 Belhe et al.
7,854,746 B2 12/2010 Dorn et al.
7,867,216 B2 1/2011 Wahr et al.
7,879,062 B2 2/2011 Galdonik et al.
7,905,856 B2 3/2011 McGuckin, Jr. et al.
7,905,877 B1 3/2011 Jimenez et al.
7,905,891 B2 3/2011 Self
7,909,812 B2 3/2011 Jansen et al.
7,927,309 B2 4/2011 Palm
7,927,347 B2 4/2011 Hogendijk et al.
7,931,659 B2 4/2011 Bose et al.
7,938,820 B2 5/2011 Webster et al.
7,967,789 B2 6/2011 Solar et al.
7,972,294 B2 7/2011 Nash et al.
7,972,298 B2 7/2011 Wallace et al.
7,972,308 B2 7/2011 Putz
7,988,646 B2 8/2011 Taber
7,998,104 B2 8/2011 Chang
8,021,351 B2 9/2011 Boldenow et al.
8,029,533 B2 10/2011 Bagaoisan et al.
8,043,279 B2 10/2011 Hisamatsu et al.
8,048,032 B2 11/2011 Root et al.
8,052,636 B2 11/2011 Moll et al.
8,052,640 B2 11/2011 Fiorella et al.
8,066,757 B2 11/2011 Ferrera et al.
8,070,694 B2 12/2011 Galdonik et al.
8,084,246 B2 12/2011 Hoon et al.
8,092,483 B2 1/2012 Galdonik et al.
8,114,032 B2 2/2012 Ferry et al.
8,142,413 B2 3/2012 Root et al.
RE43,300 E 4/2012 Saadat et al.
8,152,782 B2 4/2012 Jang et al.
8,157,760 B2 4/2012 Criado et al.
8,172,831 B2 5/2012 Webler, Jr.
8,181,324 B2 5/2012 McFadden et al.
8,211,023 B2 7/2012 Swan et al.
8,221,348 B2 7/2012 Hackett et al.
8,231,600 B2 7/2012 von Hoffmann
8,235,968 B2 8/2012 Tremaglio
8,251,978 B2 8/2012 Nash et al.
8,252,010 B1 8/2012 Raju et al.
8,252,014 B2 8/2012 Fisher
8,257,302 B2 9/2012 Beyar et al.
8,292,850 B2 10/2012 Root et al.
8,308,712 B2 11/2012 Provost et al.
8,343,089 B2 1/2013 Chang
8,361,105 B2 1/2013 Adams et al.
8,366,735 B2 2/2013 Bose et al.
8,414,516 B2 4/2013 Chang
8,419,786 B2 4/2013 Cottone, Jr. et al.
8,425,549 B2 4/2013 Lenker et al.
8,460,312 B2 6/2013 Bose et al.
8,465,456 B2 6/2013 Stivland

(56) References Cited

U.S. PATENT DOCUMENTS 8,523,801 B2 9/2013 Nash et al.
8,535,272 B2 9/2013 Wang et al.
8,540,759 B2 9/2013 Porter
8,545,514 B2 10/2013 Ferrera
8,545,552 B2 10/2013 Garrison et al.
8,574,245 B2 11/2013 Garrison et al.
8,600,477 B2 12/2013 Beyar et al.
8,609,426 B2 12/2013 Silver
8,636,714 B2 1/2014 McFerran
8,663,259 B2 3/2014 Levine et al.
8,682,411 B2 3/2014 Kassab et al.
8,690,907 B1 4/2014 Janardhan et al.
8,702,680 B2 4/2014 Jimenez et al.
8,708,954 B2 4/2014 Webler
8,715,314 B1 5/2014 Janardhan et al.
8,725,249 B2 5/2014 Bar-Yoseph et al.
8,734,374 B2 5/2014 Aklog et al.
8,758,325 B2 6/2014 Webster et al.
8,764,779 B2 7/2014 Levine et al.
8,764,813 B2 7/2014 Jantzen et al.
8,795,305 B2 8/2014 Martin et al.
8,801,670 B2 8/2014 Drontle et al.
8,801,749 B2 8/2014 Adams et al.
8,814,892 B2 8/2014 Galdonik et al.
8,870,805 B2 10/2014 Chang
8,876,776 B2 11/2014 Kassab et al.
8,932,286 B2 1/2015 Terry et al.
8,932,320 B1 1/2015 Janardhan et al.
RE45,380 E 2/2015 Root et al.
8,961,533 B2 2/2015 Stahler et al.
8,961,549 B2 2/2015 Conn
8,974,411 B2 3/2015 McKinnon
8,996,095 B2 3/2015 Anderson et al.
9,014,786 B2 4/2015 Carmeli et al.
9,023,070 B2 5/2015 Levine et al.
9,034,007 B2 5/2015 Janardhan
9,107,691 B2 8/2015 Fojtik
9,119,656 B2 9/2015 Bose et al.
9,126,018 B1 9/2015 Garrison
9,144,383 B2 9/2015 Zharov
9,144,662 B2 9/2015 Di Caprio et al.
RE45,760 E 10/2015 Root et al.
RE45,776 E 10/2015 Root et al.
9,199,057 B2 12/2015 Nielsen
9,211,132 B2 12/2015 Bowman
9,220,562 B2 12/2015 Brannan et al.
9,233,230 B2 1/2016 Puhasmagi et al.
9,241,699 B1 1/2016 Kume et al.
9,259,215 B2 2/2016 Chou et al.
9,259,228 B2 2/2016 Cruise et al.
9,265,512 B2 2/2016 Garrison et al.
9,278,201 B2 3/2016 Rapaport et al.
9,282,992 B2 3/2016 Levine et al.
9,295,817 B2 3/2016 Chang
9,314,268 B2 4/2016 Cahill
9,333,102 B2 5/2016 Yachia et al.
9,351,993 B2 5/2016 Cruise et al.
9,352,123 B2 5/2016 Zhou et al.
9,370,639 B2 6/2016 Plassman et al.
9,375,223 B2 6/2016 Wallace
9,381,278 B2 7/2016 Constant et al.
9,399,118 B2 7/2016 Kume et al.
RE46,116 E 8/2016 Root et al.
9,408,916 B2 8/2016 Cruise et al.
9,414,819 B2 8/2016 Fitz et al.
9,433,427 B2 9/2016 Look et al.
9,439,791 B2 9/2016 Vong et al.
9,445,828 B2 9/2016 Turjman et al.
9,445,927 B2 9/2016 Lee et al.
9,451,884 B2 9/2016 Zharov et al.
9,451,963 B2 9/2016 Cruise et al.
9,486,221 B2 11/2016 Cruise et al.
9,486,611 B2 11/2016 Petersen et al.
9,492,637 B2 11/2016 Garrison et al.
9,504,476 B2 11/2016 Gulachenski
9,510,855 B2 12/2016 Rapaport et al.
9,526,504 B2 12/2016 Chang
9,526,505 B2 12/2016 Marks et al.
9,532,792 B2 1/2017 Galdonik et al.
9,533,344 B2 1/2017 Monetti et al.
9,539,022 B2 1/2017 Bowman
9,539,122 B2 1/2017 Burke et al.
9,546,236 B2 1/2017 Cruise et al.
9,561,121 B2 2/2017 Sudin et al.
9,561,125 B2 2/2017 Bowman et al.
9,561,345 B2 2/2017 Garrison et al.
9,597,101 B2 3/2017 Galdonik et al.
9,615,832 B2 4/2017 Bose et al.
9,622,753 B2 4/2017 Cox
9,623,228 B2 4/2017 Ryan et al.
9,655,633 B2 5/2017 Leynov et al.
9,655,755 B2 5/2017 Chou et al.
9,655,989 B2 5/2017 Cruise et al.
9,662,118 B2 5/2017 Chang
9,662,129 B2 5/2017 Galdonik et al.
9,662,480 B2 5/2017 Kume et al.
9,669,183 B2 6/2017 Chang
9,669,191 B2 6/2017 Chou et al.
9,681,882 B2 6/2017 Garrison et al.
9,688,788 B2 6/2017 Plotkin et al.
9,693,789 B2 7/2017 Garrison et al.
9,693,852 B2 7/2017 Lam et al.
9,717,500 B2 8/2017 Tieu et al.
9,724,103 B2 8/2017 Cruise et al.
9,764,111 B2 9/2017 Gulachenski
9,764,118 B2 9/2017 Anderson et al.
9,770,251 B2 9/2017 Bowman et al.
9,789,242 B2 10/2017 Criado et al.
9,803,043 B2 10/2017 Cruise et al.
9,820,761 B2 11/2017 Garrison et al.
9,827,047 B2 11/2017 Fudaba et al.
9,861,783 B2 1/2018 Garrison et al.
9,867,725 B2 1/2018 Tieu et al.
9,877,731 B2 1/2018 Cruise et al.
9,883,885 B2 2/2018 Hendrick et al.
9,907,880 B2 3/2018 Cruise et al.
9,993,613 B2 6/2018 Wang et al.
10,058,339 B2 8/2018 Galdonik et al.
10,124,146 B2 11/2018 Di Caprio et al.
10,183,146 B2 1/2019 Yang et al.
10,192,230 B2 1/2019 Look et al.
10,213,582 B2 2/2019 Garrison et al.
10,299,944 B2 5/2019 Al-Lamee et al.
10,441,301 B2 10/2019 Vale et al.
10,456,552 B2 10/2019 Goyal
10,500,074 B2 12/2019 Denison et al.
10,624,772 B2 4/2020 Strauss et al.
10,667,871 B2 6/2020 Romo et al.
11,065,019 B1 7/2021 Chou et al.
11,400,255 B1 8/2022 Chou et al.
11,576,691 B2 2/2023 Chou et al.
2001/0014790 A1 8/2001 Heller et al.
2001/0020161 A1 9/2001 Klima et al.
2001/0027310 A1 10/2001 Parisi et al.
2001/0031980 A1 10/2001 Wensel et al.
2001/0044598 A1 11/2001 Parodi
2001/0044600 A1 11/2001 Elkins
2001/0044632 A1 11/2001 Daniel et al.
2001/0049486 A1 12/2001 Evans et al.
2001/0049517 A1 12/2001 Zadno-Azizi et al.
2001/0051811 A1 12/2001 Bonnette et al.
2002/0016565 A1 2/2002 Zadno-Azizi et al.
2002/0026145 A1 2/2002 Bagaoisan et al.
2002/0035347 A1 3/2002 Bagaoisan et al.
2002/0055747 A1 5/2002 Cano et al.
2002/0062133 A1 5/2002 Gilson et al.
2002/0072705 A1 6/2002 Vrba et al.
2002/0072730 A1 6/2002 McGill et al.
2002/0077600 A1 6/2002 Sirimanne
2002/0087076 A1 7/2002 Meguro et al.
2002/0087119 A1 7/2002 Parodi
2002/0091407 A1 7/2002 Zadno-Azizi et al.
2002/0095174 A1 7/2002 Tsugita et al.
2002/0111648 A1 8/2002 Kusleika et al.

(56) References Cited

U.S. PATENT DOCUMENTS

2002/0111666 A1 8/2002 Hart et al.
2002/0123765 A1 9/2002 Sepetka et al.
2002/0128679 A1 9/2002 Turovskiy et al.
2002/0133111 A1 9/2002 Shadduck
2002/0138094 A1 9/2002 Borillo et al.
2002/0143362 A1 10/2002 Macoviak et al.
2002/0151922 A1 10/2002 Hogendijk et al.
2002/0151927 A1 10/2002 Douk et al.
2002/0156455 A1 10/2002 Barbut
2002/0156460 A1 10/2002 Ye et al.
2002/0165571 A1 11/2002 Hebert et al.
2002/0165574 A1 11/2002 Ressemann et al.
2002/0165598 A1 11/2002 Wahr et al.
2002/0169472 A1 11/2002 Douk et al.
2002/0173785 A1 11/2002 Spear et al.
2002/0173815 A1 11/2002 Hogendijk et al.
2002/0177869 A1 11/2002 Eidenschink et al.
2002/0177899 A1 11/2002 Eum et al.
2002/0183782 A1 12/2002 Tsugita et al.
2002/0183783 A1 12/2002 Shadduck
2003/0023263 A1 1/2003 Krolik et al.
2003/0040762 A1 2/2003 Dorros et al.
2003/0050600 A1 3/2003 Ressemann et al.
2003/0065353 A1 4/2003 Horzewski et al.
2003/0065356 A1 4/2003 Tsugita et al.
2003/0069468 A1 4/2003 Bolling et al.
2003/0078562 A1 4/2003 Makower et al.
2003/0120208 A1 6/2003 Houser et al.
2003/0130577 A1 7/2003 Purdy et al.
2003/0135193 A1 7/2003 Hilgers et al.
2003/0135198 A1 7/2003 Berhow et al.
2003/0135232 A1 7/2003 Douk et al.
2003/0153942 A1 8/2003 Wang et al.
2003/0186203 A1 10/2003 Aboud
2003/0191492 A1 10/2003 Gellman et al.
2003/0212304 A1 11/2003 Lattouf
2003/0212384 A1 11/2003 Hayden
2003/0233038 A1 12/2003 Hassett
2004/0006344 A1 1/2004 Nguyen et al.
2004/0006365 A1 1/2004 Brady et al.
2004/0015138 A1 1/2004 Currier et al.
2004/0015151 A1 1/2004 Chambers
2004/0019322 A1 1/2004 Hoffmann
2004/0059243 A1 3/2004 Flores et al.
2004/0082879 A1 4/2004 Klint
2004/0087933 A1 5/2004 Lee et al.
2004/0106913 A1 6/2004 Eidenschink et al.
2004/0106977 A1 6/2004 Sullivan et al.
2004/0116878 A1 6/2004 Byrd et al.
2004/0122360 A1 6/2004 Waldhauser et al.
2004/0133232 A1 7/2004 Rosenbluth et al.
2004/0138608 A1 7/2004 Barbut et al.
2004/0153049 A1 8/2004 Hewitt et al.
2004/0153118 A1 8/2004 Clubb et al.
2004/0193046 A1 9/2004 Nash et al.
2004/0193177 A1 9/2004 Houghton et al.
2004/0210194 A1 10/2004 Bonnette et al.
2004/0220611 A1 11/2004 Ogle
2004/0230285 A1 11/2004 Gifford, III et al.
2004/0236215 A1 11/2004 Mihara et al.
2004/0243102 A1 12/2004 Berg et al.
2004/0254602 A1 12/2004 Lehe et al.
2005/0004523 A1 1/2005 Osborne et al.
2005/0004553 A1 1/2005 Douk
2005/0021002 A1 1/2005 Deckman et al.
2005/0021075 A1 1/2005 Bonnette et al.
2005/0021152 A1 1/2005 Ogle et al.
2005/0027236 A1 2/2005 Douk
2005/0049574 A1 3/2005 Petrick et al.
2005/0059957 A1 3/2005 Campbell et al.
2005/0065467 A1 3/2005 Pudelko et al.
2005/0065498 A1 3/2005 McFerran
2005/0075661 A1 4/2005 Levine et al.
2005/0085746 A1 4/2005 Adams et al.
2005/0085847 A1 4/2005 Galdonik et al.
2005/0090802 A1 4/2005 Connors et al.
2005/0103332 A1 5/2005 Gingles et al.
2005/0107738 A1 5/2005 Slater et al.
2005/0125021 A1 6/2005 Nance et al.
2005/0131453 A1 6/2005 Parodi
2005/0154344 A1 7/2005 Chang
2005/0154349 A1 7/2005 Renz et al.
2005/0182386 A1 8/2005 Aggerholm
2005/0209559 A1 9/2005 Thornton et al.
2005/0209631 A1 9/2005 Galdonik et al.
2005/0209674 A1 9/2005 Kutscher et al.
2005/0209675 A1 9/2005 Ton et al.
2005/0228479 A1 10/2005 Pavcnik et al.
2005/0245892 A1 11/2005 Elkins et al.
2005/0273051 A1 12/2005 Coppi
2005/0277976 A1 12/2005 Galdonik et al.
2006/0020165 A1 1/2006 Adams
2006/0030835 A1 2/2006 Sherman et al.
2006/0030876 A1 2/2006 Peacock et al.
2006/0047301 A1 3/2006 Ogle
2006/0058836 A1 3/2006 Bose et al.
2006/0058837 A1 3/2006 Bose et al.
2006/0058838 A1 3/2006 Bose et al.
2006/0064036 A1 3/2006 Osborne et al.
2006/0079787 A1 4/2006 Whiting et al.
2006/0089618 A1 4/2006 McFerran et al.
2006/0095062 A1 5/2006 Stephens
2006/0100530 A1 5/2006 Kliot et al.
2006/0129091 A1 6/2006 Bonnette et al.
2006/0135961 A1 6/2006 Rosenman et al.
2006/0173440 A1 8/2006 Lamson et al.
2006/0195137 A1 8/2006 Sepetka et al.
2006/0200047 A1 9/2006 Galdonik et al.
2006/0200191 A1 9/2006 Zadno-Azizi
2006/0217664 A1 9/2006 Hattler et al.
2006/0247755 A1 11/2006 Pal et al.
2006/0258987 A1 11/2006 Lentz et al.
2006/0259063 A1 11/2006 Bates et al.
2006/0264759 A1 11/2006 Moehring et al.
2006/0270977 A1 11/2006 Fisher et al.
2006/0271098 A1 11/2006 Peacock
2007/0005002 A1 1/2007 Millman et al.
2007/0005084 A1 1/2007 Clague et al.
2007/0010863 A1 1/2007 Stenzel
2007/0016132 A1 1/2007 Oepen et al.
2007/0021778 A1 1/2007 Carly
2007/0043333 A1 2/2007 Kampa et al.
2007/0060888 A1 3/2007 Goff et al.
2007/0060908 A1 3/2007 Webster et al.
2007/0060911 A1 3/2007 Webster et al.
2007/0060944 A1 3/2007 Boldenow et al.
2007/0073264 A1 3/2007 Stedman et al.
2007/0088323 A1 4/2007 Campbell et al.
2007/0106211 A1 5/2007 Provost-Tine et al.
2007/0135733 A1 6/2007 Soukup et al.
2007/0135832 A1 6/2007 Wholey et al.
2007/0173784 A1 7/2007 Johansson et al.
2007/0185501 A1 8/2007 Martin et al.
2007/0185521 A1 8/2007 Bui et al.
2007/0185522 A1 8/2007 Davies et al.
2007/0191820 A1 8/2007 Maksimovich
2007/0197956 A1 8/2007 Le et al.
2007/0198028 A1 8/2007 Miloslavski et al.
2007/0198049 A1 8/2007 Barbut
2007/0208302 A1 9/2007 Webster et al.
2007/0227543 A1 10/2007 Peichel
2007/0239261 A1 10/2007 Bose et al.
2007/0250040 A1 10/2007 Provost et al.
2007/0250096 A1 10/2007 Yamane et al.
2007/0260115 A1 11/2007 Brock et al.
2007/0265516 A1 11/2007 Wang
2007/0287956 A1 12/2007 Tal
2008/0027379 A1 1/2008 Wilkins
2008/0033525 A1 2/2008 Shaked et al.
2008/0058839 A1 3/2008 Nobles et al.
2008/0082107 A1 4/2008 Miller et al.
2008/0082109 A1 4/2008 Moll et al.
2008/0086110 A1 4/2008 Galdonik et al.
2008/0097251 A1 4/2008 Babaev

(56) References Cited

U.S. PATENT DOCUMENTS

2008/0097395 A1 4/2008 Adams et al.
2008/0109088 A1 5/2008 Galdonik et al.
2008/0119890 A1 5/2008 Adams et al.
2008/0140010 A1 6/2008 Kennedy et al.
2008/0167678 A1 7/2008 Morsi
2008/0172066 A9 7/2008 Galdonik et al.
2008/0177245 A1 7/2008 Mesallum
2008/0183128 A1 7/2008 Morriss et al.
2008/0188888 A1 8/2008 Adams et al.
2008/0195140 A1 8/2008 Myla et al.
2008/0200946 A1 8/2008 Braun et al.
2008/0234723 A1 9/2008 Buiser et al.
2008/0243222 A1 10/2008 Schafersman et al.
2008/0262350 A1 10/2008 Unger
2008/0262472 A1 10/2008 Lunn et al.
2008/0262506 A1 10/2008 Griffin et al.
2008/0281248 A1 11/2008 Angheloiu et al.
2008/0294111 A1 11/2008 Tal et al.
2008/0312639 A1 12/2008 Weber
2009/0018455 A1 1/2009 Chang
2009/0018525 A1 1/2009 Waite et al.
2009/0024072 A1 1/2009 Criado et al.
2009/0024089 A1 1/2009 Levine et al.
2009/0030400 A1 1/2009 Bose et al.
2009/0076319 A1 3/2009 Muyari
2009/0082800 A1 3/2009 Janardhan
2009/0124956 A1 5/2009 Swetlin et al.
2009/0131970 A1 5/2009 Chanduszko et al.
2009/0163891 A1 6/2009 Ewing et al.
2009/0165881 A1 7/2009 Tegg et al.
2009/0198172 A1 8/2009 Garrison et al.
2009/0209857 A1 8/2009 Secretain et al.
2009/0227992 A1 9/2009 Nir et al.
2009/0234321 A1 9/2009 Shapland et al.
2009/0247987 A1 10/2009 Chevalier, Jr. et al.
2009/0254166 A1 10/2009 Chou et al.
2009/0264865 A1 10/2009 Kawai
2009/0270800 A1 10/2009 Spurchise et al.
2009/0281379 A1 11/2009 Binmoeller et al.
2009/0299393 A1 12/2009 Martin et al.
2009/0312699 A1 12/2009 Pudelko et al.
2009/0312786 A1 12/2009 Trask et al.
2010/0004607 A1 1/2010 Wilson et al.
2010/0022948 A1 1/2010 Wilson et al.
2010/0030141 A1 2/2010 Chermoni
2010/0030186 A1 2/2010 Stivland
2010/0042118 A1 2/2010 Garrison et al.
2010/0049147 A1 2/2010 Tanikawa et al.
2010/0049168 A1 2/2010 Parker et al.
2010/0057051 A1 3/2010 Howat et al.
2010/0063479 A1 3/2010 Merdan et al.
2010/0063480 A1 3/2010 Shireman
2010/0094330 A1 4/2010 Barbut
2010/0114017 A1 5/2010 Lenker et al.
2010/0125322 A1 5/2010 Fitzgerald et al.
2010/0145308 A1 6/2010 Layman et al.
2010/0185216 A1 7/2010 Garrison et al.
2010/0204634 A1 8/2010 Baxter et al.
2010/0204672 A1 8/2010 Lockhart et al.
2010/0204684 A1 8/2010 Garrison et al.
2010/0211050 A1 8/2010 Luther
2010/0217235 A1 8/2010 Thorstenson et al.
2010/0217276 A1 8/2010 Garrison et al.
2010/0228269 A1 9/2010 Garrison et al.
2010/0256600 A1 10/2010 Ferrera
2010/0268029 A1 10/2010 Phan et al.
2010/0280451 A1 11/2010 Teeslink et al.
2010/0305475 A1* 12/2010 Hinchliffe ............. A61M 25/09 600/585
2010/0312141 A1 12/2010 Keast et al.
2010/0318097 A1 12/2010 Ferrera et al.
2011/0009875 A1 1/2011 Grandfield et al.
2011/0015482 A1 1/2011 Carrillo, Jr.
2011/0022149 A1 1/2011 Cox et al.
2011/0034986 A1 2/2011 Chou et al.
2011/0046709 A1 2/2011 Coffey et al.
2011/0082373 A1 4/2011 Gurley et al.
2011/0087147 A1 4/2011 Garrison et al.
2011/0092910 A1 4/2011 Schultz
2011/0093000 A1 4/2011 Ogle et al.
2011/0106200 A1 5/2011 Ziegler
2011/0112567 A1 5/2011 Lenker et al.
2011/0125181 A1 5/2011 Brady et al.
2011/0152760 A1 6/2011 Parker
2011/0160833 A1 6/2011 Gonzalez et al.
2011/0172678 A1 7/2011 Behl et al.
2011/0172700 A1 7/2011 Bose et al.
2011/0230859 A1 9/2011 Galdonik et al.
2011/0238041 A1 9/2011 Lim et al.
2011/0238083 A1 9/2011 Moll et al.
2011/0245751 A1 10/2011 Hofmann
2011/0264133 A1 10/2011 Hanlon et al.
2012/0040858 A1 2/2012 Ford et al.
2012/0065479 A1 3/2012 Lahiji et al.
2012/0065490 A1 3/2012 Zharov et al.
2012/0071838 A1 3/2012 Fojtik
2012/0071856 A1 3/2012 Goldfarb et al.
2012/0078140 A1 3/2012 Nita
2012/0095485 A1 4/2012 Cully et al.
2012/0101561 A1 4/2012 Porter
2012/0109044 A1 5/2012 Santamore et al.
2012/0116350 A1 5/2012 Strauss et al.
2012/0123466 A1 5/2012 Porter et al.
2012/0148175 A1 6/2012 Wesselmann
2012/0150147 A1 6/2012 Leynov et al.
2012/0165756 A1 6/2012 Root et al.
2012/0172918 A1 7/2012 Fifer et al.
2012/0179097 A1 7/2012 Cully et al.
2012/0253313 A1 10/2012 Galdonik et al.
2012/0271281 A1 10/2012 Schertiger
2012/0277671 A1 11/2012 Fuentes
2012/0296275 A1 11/2012 Martin et al.
2012/0310212 A1 12/2012 Fischell et al.
2012/0310319 A1 12/2012 Tieu et al.
2012/0330196 A1 12/2012 Nita
2013/0006174 A1 1/2013 Phan
2013/0006225 A1 1/2013 Cucin
2013/0018318 A1 1/2013 Ravichandran et al.
2013/0035628 A1 2/2013 Garrison et al.
2013/0046285 A1 2/2013 Griffin et al.
2013/0053792 A1 2/2013 Fischell et al.
2013/0060206 A1 3/2013 Consigny
2013/0116701 A1 5/2013 Wang et al.
2013/0131691 A1 5/2013 Kozak et al.
2013/0158507 A1 6/2013 Brown
2013/0158578 A1 6/2013 Ghodke et al.
2013/0165873 A1 6/2013 Morriss et al.
2013/0172851 A1 7/2013 Shimada et al.
2013/0184598 A1 7/2013 Bowe et al.
2013/0184735 A1 7/2013 Fischell et al.
2013/0184742 A1 7/2013 Ganesan et al.
2013/0197621 A1 8/2013 Ryan et al.
2013/0225937 A1 8/2013 Schaeffer et al.
2013/0226276 A1 8/2013 Newell et al.
2013/0261727 A1 10/2013 Perkins et al.
2013/0274783 A1 10/2013 Wynberg
2013/0281788 A1 10/2013 Garrison
2013/0317409 A1 11/2013 Cully et al.
2014/0012281 A1 1/2014 Wang et al.
2014/0018732 A1 1/2014 Bagaoisan et al.
2014/0018773 A1 1/2014 Wang et al.
2014/0025004 A1 1/2014 Falk et al.
2014/0025043 A1 1/2014 Wang et al.
2014/0039461 A1 2/2014 Anderson et al.
2014/0046297 A1 2/2014 Shimada et al.
2014/0081243 A1 3/2014 Zhou et al.
2014/0088510 A1 3/2014 Nimkar et al.
2014/0114287 A1 4/2014 Beasley et al.
2014/0114335 A1 4/2014 Banko
2014/0117397 A1 5/2014 Saeki et al.
2014/0128901 A1 5/2014 Kang et al.
2014/0155783 A1 6/2014 Starksen et al.
2014/0155862 A1 6/2014 Baxter et al.
2014/0155908 A1 6/2014 Rosenbluth et al.

(56) References Cited

U.S. PATENT DOCUMENTS

2014/0155932 A1 6/2014 Weishaupt et al.
2014/0180246 A1 6/2014 Comerota et al.
2014/0207043 A1 7/2014 Anand et al.
2014/0228808 A1 8/2014 Webster et al.
2014/0236120 A1 8/2014 Tsai et al.
2014/0249508 A1 9/2014 Wang et al.
2014/0257018 A1 9/2014 Farnan
2014/0257186 A1 9/2014 Kerr
2014/0273920 A1 9/2014 Smith
2014/0276537 A1 9/2014 Kruse
2014/0276618 A1 9/2014 Di Caprio et al.
2014/0276920 A1 9/2014 Hendrick et al.
2014/0276923 A1 9/2014 Miller
2014/0288525 A1 9/2014 Fudaba et al.
2014/0296769 A1 10/2014 Hyde et al.
2014/0296868 A1 10/2014 Garrison et al.
2014/0296889 A1 10/2014 Avneri et al.
2014/0343537 A1 11/2014 Eversull et al.
2014/0343585 A1 11/2014 Ferrera et al.
2014/0358123 A1 12/2014 Ueda et al.
2014/0358178 A1 12/2014 Hewitt et al.
2014/0371709 A1 12/2014 Allen et al.
2015/0018937 A1 1/2015 Lagodzki et al.
2015/0025562 A1 1/2015 Dinh et al.
2015/0080939 A1 3/2015 Adams et al.
2015/0105729 A1 4/2015 Valeti et al.
2015/0119859 A1 4/2015 Cajamarca et al.
2015/0126861 A1 5/2015 Gambhir et al.
2015/0133978 A1 5/2015 Paul, Jr.
2015/0151090 A1 6/2015 Sutton et al.
2015/0165160 A1 6/2015 Thungana et al.
2015/0173782 A1 6/2015 Garrison et al.
2015/0174368 A1 6/2015 Garrison et al.
2015/0196210 A1 7/2015 McCaffrey et al.
2015/0209066 A1 7/2015 Dahm et al.
2015/0216650 A1 8/2015 Shaltis
2015/0245848 A1 9/2015 Shimon
2015/0265802 A1 9/2015 Fukuoka et al.
2015/0282821 A1 10/2015 Look et al.
2015/0314111 A1 11/2015 Solar et al.
2015/0327843 A1 11/2015 Garrison
2015/0327919 A1 11/2015 Clopp et al.
2015/0335857 A1 11/2015 Ishikawa
2015/0352330 A1 12/2015 Wasdyke et al.
2016/0008025 A1 1/2016 Gupta et al.
2016/0008572 A1 1/2016 Di Caprio et al.
2016/0015935 A1 1/2016 Chan et al.
2016/0022964 A1 1/2016 Goyal
2016/0058459 A1 3/2016 Bowman
2016/0066931 A1 3/2016 Kugler et al.
2016/0081825 A1 3/2016 Sudin et al.
2016/0096002 A1 4/2016 Di Caprio et al.
2016/0100819 A1 4/2016 Tieu
2016/0121081 A1 5/2016 Iwano et al.
2016/0128688 A1 5/2016 Garrison et al.
2016/0129221 A1 5/2016 Haverkost et al.
2016/0135829 A1 5/2016 Holochwost et al.
2016/0136398 A1 5/2016 Heilman et al.
2016/0143661 A1 5/2016 Wood et al.
2016/0144157 A1 5/2016 Gulachenski et al.
2016/0166265 A1 6/2016 Nita
2016/0166266 A1 6/2016 Nita
2016/0166754 A1 6/2016 Kassab et al.
2016/0199204 A1 7/2016 Pung et al.
2016/0199620 A1 7/2016 Pokorney et al.
2016/0206322 A1 7/2016 Fitz et al.
2016/0220396 A1 8/2016 Zhou et al.
2016/0220741 A1 8/2016 Garrison et al.
2016/0242764 A1 8/2016 Garrison et al.
2016/0242893 A1 8/2016 Joshi et al.
2016/0243157 A1 8/2016 Cruise et al.
2016/0256611 A1 9/2016 Fitz
2016/0270806 A1 9/2016 Wallace
2016/0271315 A1 9/2016 Chang
2016/0296690 A1 10/2016 Kume et al.
2016/0311990 A1 10/2016 Cruise et al.
2016/0317156 A1 11/2016 Fitz et al.
2016/0317288 A1 11/2016 Rogers et al.
2016/0345904 A1 12/2016 Bowman
2016/0346502 A1 12/2016 Fuller et al.
2016/0346508 A1 12/2016 Williams et al.
2016/0346509 A1 12/2016 Anderson et al.
2016/0361180 A1 12/2016 Vong et al.
2016/0361459 A1 12/2016 Baldwin
2016/0367272 A1 12/2016 Garrison et al.
2016/0367274 A1 12/2016 Wallace
2016/0367275 A1 12/2016 Wallace
2017/0007264 A1 1/2017 Cruise et al.
2017/0007277 A1 1/2017 Drapeau et al.
2017/0020540 A1 1/2017 Chou et al.
2017/0027604 A1 2/2017 Wallace
2017/0028170 A1 2/2017 Ho
2017/0035436 A1 2/2017 Morita
2017/0035446 A1 2/2017 Rapaport et al.
2017/0042548 A1 2/2017 Lam
2017/0056032 A1 3/2017 Look et al.
2017/0056061 A1 3/2017 Ogle et al.
2017/0072165 A1 3/2017 Lim et al.
2017/0072452 A1 3/2017 Monetti et al.
2017/0079680 A1 3/2017 Bowman
2017/0079812 A1 3/2017 Lam et al.
2017/0079817 A1 3/2017 Sepetka et al.
2017/0079819 A1 3/2017 Pung et al.
2017/0079820 A1 3/2017 Lam et al.
2017/0087340 A1 3/2017 Peralta et al.
2017/0100126 A1 4/2017 Bowman et al.
2017/0143938 A1 5/2017 Ogle et al.
2017/0147765 A1 5/2017 Mehta
2017/0164964 A1 6/2017 Galdonik et al.
2017/0172581 A1 6/2017 Bose et al.
2017/0172766 A1 6/2017 Vong et al.
2017/0181760 A1 6/2017 Look et al.
2017/0189033 A1 7/2017 Sepetka et al.
2017/0203036 A1 7/2017 Mazlish et al.
2017/0209260 A1 7/2017 Garrison et al.
2017/0215902 A1 8/2017 Leynov et al.
2017/0216484 A1 8/2017 Cruise et al.
2017/0224350 A1 8/2017 Shimizu et al.
2017/0224355 A1 8/2017 Bowman et al.
2017/0224953 A1 8/2017 Tran et al.
2017/0231647 A1 8/2017 Saunders et al.
2017/0246014 A1 8/2017 Rapaport et al.
2017/0252043 A1 9/2017 Fuller et al.
2017/0265869 A1 9/2017 Cibulski et al.
2017/0265983 A1 9/2017 Lam et al.
2017/0274180 A1 9/2017 Garrison et al.
2017/0281192 A1 10/2017 Tieu et al.
2017/0281204 A1 10/2017 Garrison et al.
2017/0283536 A1 10/2017 Cruise et al.
2017/0290600 A1 10/2017 Ulm, III
2017/0348514 A1 12/2017 Guyon et al.
2017/0354421 A1 12/2017 Maguire et al.
2017/0354523 A1 12/2017 Chou et al.
2017/0354803 A1 12/2017 Kume et al.
2017/0360450 A1 12/2017 Tompkins et al.
2017/0361072 A1 12/2017 Chou et al.
2017/0367713 A1 12/2017 Greene, Jr. et al.
2017/0367857 A1 12/2017 Bennett et al.
2017/0368296 A1 12/2017 Chang
2017/0368309 A1 12/2017 Garrison et al.
2018/0008294 A1 1/2018 Garrison et al.
2018/0008295 A1 1/2018 Ulm, III
2018/0008439 A9 1/2018 Tieu et al.
2018/0014840 A1 1/2018 Panian
2018/0028205 A1 2/2018 Chou et al.
2018/0028209 A1 2/2018 Sudin et al.
2018/0036155 A1 2/2018 Tieu et al.
2018/0055516 A1 3/2018 Baldwin et al.
2018/0064453 A1 3/2018 Garrison et al.
2018/0116684 A1 5/2018 Garrison et al.
2018/0133436 A1 5/2018 Garrison et al.
2018/0242978 A1 8/2018 Chou et al.
2019/0008534 A1 1/2019 Garrison et al.
2019/0046218 A1 2/2019 Garrison et al.

(56) References Cited

U.S. PATENT DOCUMENTS

| | | | |
|---|---|---|---|
| 2019/0133744 | A1 | 5/2019 | Janardhan et al. |
| 2019/0269538 | A1 | 9/2019 | Chou et al. |
| 2019/0366042 | A1 | 12/2019 | Garrison et al. |
| 2019/0366043 | A1 | 12/2019 | Garrison et al. |
| 2020/0016369 | A1 | 1/2020 | Garrison et al. |
| 2020/0046939 | A1 | 2/2020 | Garrison et al. |
| 2020/0060722 | A1 | 2/2020 | O'Connell et al. |
| 2020/0164178 | A1 | 5/2020 | Garrison et al. |
| 2020/0187965 | A1 | 6/2020 | Garrison et al. |
| 2020/0197031 | A1 | 6/2020 | Nguyen et al. |
| 2020/0215306 | A1 | 7/2020 | Garrison et al. |
| 2020/0337716 | A1 | 10/2020 | Garrison et al. |
| 2020/0345981 | A1 | 11/2020 | Garrison et al. |
| 2021/0045758 | A1 | 2/2021 | Garrison et al. |
| 2021/0052296 | A1 | 2/2021 | Garrison |
| 2021/0069467 | A1 | 3/2021 | Garrison et al. |
| 2021/0138193 | A1 | 5/2021 | Garrison et al. |
| 2021/0138194 | A1 | 5/2021 | Garrison et al. |
| 2021/0212707 | A1 | 7/2021 | Chou et al. |
| 2022/0047285 | A1 | 2/2022 | Chou et al. |

FOREIGN PATENT DOCUMENTS

| | | | |
|---|---|---|---|
| CN | 103110998 | A | 5/2013 |
| CN | 103260689 | A | 8/2013 |
| CN | 103284775 | A | 9/2013 |
| CN | 103648574 | A | 3/2014 |
| CN | 103861193 | A | 6/2014 |
| CN | 204158457 | U | 2/2015 |
| CN | 104394785 | A | 3/2015 |
| CN | 104739486 | A | 7/2015 |
| DE | 102006039236 | A1 | 2/2008 |
| EP | 117940 | A2 | 9/1984 |
| EP | 0427429 | A2 | 5/1991 |
| EP | 1226795 | A2 | 7/2002 |
| EP | 1440663 | A1 | 7/2004 |
| EP | 1639951 | A1 | 3/2006 |
| EP | 2069528 | B1 | 3/2013 |
| EP | 2821094 | A1 | 1/2015 |
| EP | 1871292 | B1 | 10/2019 |
| GB | 2020557 | A | 11/1979 |
| JP | 3026200 | U | 7/1996 |
| JP | H08-173540 | A | 7/1996 |
| JP | H09-512445 | A | 12/1997 |
| JP | H11-114053 | A | 4/1999 |
| JP | H11-146883 | A | 6/1999 |
| JP | 2002-291756 | A | 10/2002 |
| JP | 2004-065326 | A | 3/2004 |
| JP | 2005-508230 | A | 3/2005 |
| JP | 2006-087643 | A | 4/2006 |
| JP | 2008-503249 | A | 2/2008 |
| JP | 2008-517652 | A | 5/2008 |
| JP | 3142466 | U | 6/2008 |
| JP | 2009-254764 | A | 11/2009 |
| JP | 2010-017211 | A | 1/2010 |
| JP | 2010-057831 | A | 3/2010 |
| JP | 2014-138756 | A | 7/2014 |
| WO | WO-88/01885 | A1 | 3/1988 |
| WO | WO-93/17750 | A1 | 9/1993 |
| WO | WO-94/02194 | A1 | 2/1994 |
| WO | WO-95/05209 | A1 | 2/1995 |
| WO | WO-98/38930 | A1 | 9/1998 |
| WO | WO-99/45835 | A2 | 9/1999 |
| WO | WO-00/16705 | A1 | 3/2000 |
| WO | WO-00/32266 | A1 | 6/2000 |
| WO | WO-00/76390 | A2 | 12/2000 |
| WO | WO-01/15767 | A1 | 3/2001 |
| WO | WO-01/58365 | A1 | 8/2001 |
| WO | WO-02/32495 | A1 | 4/2002 |
| WO | WO-02/055146 | A1 | 7/2002 |
| WO | WO-02/085092 | A2 | 10/2002 |
| WO | WO-03/018085 | A2 | 3/2003 |
| WO | WO-03/090831 | A2 | 11/2003 |
| WO | WO-2004/006803 | A1 | 1/2004 |
| WO | WO-2005/051206 | A1 | 6/2005 |
| WO | WO-2005/084130 | A2 | 9/2005 |
| WO | WO-2006/111944 | A1 | 10/2006 |
| WO | WO-2006/127929 | A2 | 11/2006 |
| WO | WO-2006/132434 | A1 | 12/2006 |
| WO | WO-2007/098494 | A1 | 8/2007 |
| WO | WO-2008/006111 | A2 | 1/2008 |
| WO | WO-2008/123521 | A1 | 10/2008 |
| WO | WO-2008/144587 | A2 | 11/2008 |
| WO | WO-2009/012473 | A3 | 1/2009 |
| WO | WO-2009/099764 | A1 | 8/2009 |
| WO | WO-2009/100210 | A1 | 8/2009 |
| WO | WO-2010/039456 | A1 | 4/2010 |
| WO | WO-2010/075445 | A1 | 7/2010 |
| WO | WO-2010/075565 | A2 | 7/2010 |
| WO | WO-2011/011493 | A1 | 1/2011 |
| WO | WO-2011/057282 | A2 | 5/2011 |
| WO | WO-2012/009518 | A1 | 1/2012 |
| WO | WO-2012/035633 | A1 | 3/2012 |
| WO | WO-2012/047803 | A2 | 4/2012 |
| WO | WO-2014/008489 | A1 | 1/2014 |
| WO | WO-2014/147815 | A1 | 9/2014 |
| WO | WO-2014/203336 | A1 | 12/2014 |
| WO | WO-2015/042368 | A2 | 3/2015 |
| WO | WO-2015/100178 | A1 | 7/2015 |
| WO | WO-2015/157330 | A1 | 10/2015 |
| WO | WO-2016/059026 | A1 | 4/2016 |
| WO | WO-2017/091554 | A1 | 6/2017 |
| WO | WO-2017/118818 | A1 | 7/2017 |

OTHER PUBLICATIONS

U.S. Appl. No. 17/089,495, filed Nov. 4, 2020, US 2021-0045758.
U.S. Appl. No. 17/093,401, filed Nov. 9, 2020, US 2021-0069467.
U.S. Appl. No. 17/319,943, filed May 13, 2021, US 2021-0259718.
U.S. Appl. No. 17/385,581, filed Jul. 26, 2021, US 2023-0029243.
U.S. Appl. No. 17/497,713, filed Oct. 8, 2021, US 2022-0111177.
U.S. Appl. No. 17/667,828, filed Feb. 9, 2022, US 2023-0359377.
U.S. Appl. No. 17/849,379, filed Jun. 24, 2022, US 2022-0313292.
U.S. Appl. No. 17/859,955, filed Jul. 7, 2022, US 2022-0338888.
U.S. Appl. No. 17/981,164, filed Nov. 4, 2022, US 2023-0059721.
U.S. Appl. No. 18/065,527, filed Dec. 13, 2022, US 2023-0248366.
U.S. Appl. No. 18/159,491, filed Jan. 25, 2023, US 2023-0165597.
U.S. Appl. No. 18/184,495, filed Mar. 15, 2023, US 2023-0293851.
U.S. Appl. No. 18/185,710, filed Mar. 17, 2023, US 2023-0277805.
U.S. Appl. No. 18/238,299, filed Aug. 25, 2023, US 2023-0405272.
U.S. Appl. No. 18/297,443, filed Apr. 7, 2023, US 2023-0241348.
U.S. Appl. No. 18/309,173, filed Apr. 28, 2023, US 2023-0277806.
U.S. Appl. No. 18/311,797, filed May 3, 2023, US 2023-0355255.
U.S. Appl. No. 18/311,802, filed May 3, 2023, US 2023-0355413.
U.S. Appl. No. 18/323,756, filed May 25, 2023, US 2023-0380915.
U.S. Appl. No. 18/350,533, filed Jul. 11, 2023, US 2024-0016633.
U.S. Appl. No. 18/485,168, filed Oct. 11, 2023, US 2024-0042170.
U.S. Appl. No. 18/514,518, filed Nov. 20, 2023, US 2024-0164801.
U.S. Appl. No. 18/514,553, filed Nov. 20, 2023, US 2024-0082542.
U.S. Appl. No. 18/539,695, filed Dec. 14, 2023, US 2024-0198039.
U.S. Appl. No. 18/625,031, filed Apr. 2, 2024, US 2024-0245415.
U.S. Appl. No. 18/651,328, filed Apr. 30, 2024, US 2025-0032289.
U.S. Appl. No. 18/911,081, filed Oct. 9, 2024, US 2025-0108190.
PCT/US2023/80572, Nov. 20, 2023, WO 2024/112693.
PCT/US2023/84030, Dec. 14, 2023, WO 2024/129972.
2007 International Stroke Conference: Abstracts. Stroke, vol. 38, No. 2, 2007, pp. 454-607. Web. Downloaded Jun. 13, 2017.
2012 Buyer's Guide: Microcatheters. Endovascular Today, 2012, pp. 48-51.
2017 Buyer's Guide: Microcatheters. Endovascular Today, http://evtoday.com/buyers-guide/chart.asp?id=25. Accessed on Oct. 10, 2017. 11 pages.
Asahi Fubuki Catheter Dilator Kit. Asahi-Intecc USA Medical. 2017. Web. Accessed Oct. 2, 2017. 3 pages. www.asahi-inteccusa-medical.com/medical-product/fubuki-dilator-kit/. Accessed Oct. 2, 2017.
Adami, M.D., et al., (2002) "Use of the Parodi Anti-Embolism System in Carotid Stenting: Italian Trial Results" J Endovasc Ther 9:147-154.

(56) References Cited

OTHER PUBLICATIONS

Alexandrescu et al. (2006) "Filter-protected carotid stenting via a minimal cervical access with transitory aspirated reversed flow during initial passage of the target lesion" J. Endovasc. Ther. 13(2):196-204.
Alvarez et al. (2008). "Transcervical carotid stenting with flow reversal is safe in octogenarians: A preliminary safety study" J. Vasc. Surg. 47:96-100.
Bates M.D., et al. (2003). "Reversal of the Direction of Internal Carotid Artery Blood Flow by Occlusion of the Common and External Carotid Arteries in a Swine Model" Catherization and Cardiovascular Intervention 60:270-275.
Bates, M.D., et al. (2004) "Internal Carotid Artery Flow Arrest/Reversal Cerebral Protection Techniques" The West Virginal Medical Journal, vol. 99:60-63.
Bergeron et al. (1999). "Percutaneous stenting of the internal carotid artery: the European CAST I Study" J. Endovasc. Surg. 6:155-159.
Bergeron et al. (2008) MEET Presentation, Cannes, French Riviera "Why I do not use routine femoral access for CAS." 12 pages.
Bergeron P. et al. (1996) "Recurrent Carotid Disease: Will Stents be an alternative to surgery?" J Endovasc Surg; 3: 76-79.
Bourekas, E. C., A. P. Slivka, et al. (2004). "Intraarterial thrombolytic therapy within 3 hours of the onset of stroke." Neurosurgery 54(1): 39-44; discussion 44-6.
Chang, D.W., et al, "A new approach to carotid angioplasty and stenting with transcervical occlusion and protective shunting: Why it may be a better carotid artery intervention" (J Vasc Surg 2004; 39:994-1002.).
Chang, M.D., "Carotid Angioplasty And Stenting Using Transcervical Occlusion And Protective Shunting Via A Mini Incision In The Neck: A New Technique For Difficult Femoral Access Or Filter Placement May Be The Better Carotid Artery Intervention" 30th Global: Vascular and Endovascular Issues, Techniques and Horizons Symposium, New York, NY, Nov. 20-23, 2003; XXVII 6.1-XXVII 6.2.
Cohen et al. (2012). "A reappraisal of the common carotid artery as an access site in interventional procedures for acute stroke therapies", Case Reports, Journal of Clinical Neuroscience 19, pp. 323-326.
Coppi et al. (2005). "PRIAMUS Proximal flow blockage cerebral protection during carotid stenting: Results from a multicenter Italian regiStry" J. Cardiovasc. Surg. 46:219-227.
Criado et al. (1997) "Evolving indications for and early results of carotid artery stenting" Am. J. Surg.; 174:111-114.
Criado et al. (2004). "Transcervical carotid artery angioplasty and stenting with carotid flow reversal: Surgical technique" J. Vasc. Surg. 18:257-261.
Criado et al. (2004). "Transcervical carotid stenting with internal carotid artery flow reversal: Feasibility and preliminary results" J. Vasc. Surg. 40:476-483.
Criado, et al. (2007). "Transcervical carotid stenting with carotid artery flow reversal: 3-year follow-up of 103 stents." J Vasc Surg 46(5): 864-9.
Criado, F.J., et al. (2000). "Access strategies for carotid artery intervention." J Invasive Cardiol, 12(1): p. 61-8.
Criado, M.D., et al. (2004) "Carotid angioplasty with internal carotid artery flow reversal is well tolerated in the awake patient" Journal of Vascular Surgery, 40(1):92-7.
Delgado Almandoz, Josser E., et al. "Comparison of clinical outcomes in patients with acute ischemic strokes treated with mechanical thrombectomy using either Solumbra or ADAPT techniques." *Journal of NeuroInterventional Surgery*, vol. 8, 2016, pp. 1123-1128.
Diederich et al. (2004) "First Clinical experiences with an endovascular clamping system for neuroprotection during carotid stenting" *Eur. J. Vasc. Endovasc. Surg.* 28:629-633.
Diethrich et al., (1996). "Percutaneous techniques for endoluminal carotid interventions" J. Endovasc. Surg. 3:182-202.
Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.
Farooq, Vasim et al. "Forward and Back Aspiration during ST-Elevation Myocardial Infarction: a Feasibility Study." EuroIntervention, vol. 11, No. 14, 2016, pp. 1639-1648.
Farooq, Vasim et al. "The Use of A Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.
Feldman, (1987). "Transcatheter Aspiration of a Thrombus in an Aortocoronary Saphenous Vein Graft," *American Journal of Cardiology*, 60(4):379-380.
Feldtman, R. W., C. J. Buckley, et al. (2006). "How I do it: cervical access for carotid artery stenting." Am J Surg 192(6): 779-81.
Fiorella, D., M. Kelly, et al. (2008). "Endovascular Treatment of Cerebral Aneurysms." Endovascular Today Jun. 2008. pp. 53-64.
Frazee, J. G. and X. Luo (1999). "Retrograde transvenous perfusion." Crit Care Clin 15(4):777-88, vii.
Frazee, J. G., X. Luo, et al. (1998). "Retrograde transvenous neuroperfusion: a back door treatment for stroke." Stroke 29(9): 1912-6.
Friedrich, Benjamin, et al. "Distance to Thrombus in Acute Middle Cerebral Artery Occlusion." *Stroke*, vol. 46, No. 3, 2015, pp. 692-696.
Frölich AM, et al. (2020, Epub Sep. 3, 2020). "The novel Tenzing 7 delivery catheter designed to deliver intermediate catheters to the face of embolus without crossing: clinical performance predicted in anatomically challenging model." J NeuroIntervent Surg, 5 pages. doi: 10.1136/ neurintsurg-2020-016412.
Goldstein (2007) "Acute Ischemic Stroke Treatment in 2007" *Circ* 116:1504-1514.
Goyal, M. et al. (Mar. 12, 2015, e-published Feb. 11, 2015). "Randomized Assessment of Rapid Endovascular Treatment of Ischemic Stroke." *N ENGL J MED*, 372(11):1019-1030.
Gray et al. (2007) "The CAPTURE registry: Results of carotid stenting with embolic protection in the post approval setting" *Cath. Cardovasc. Interven.* 69:341-348.
Guidezilla Guide Extension Catheter, Boston Scientific 510k Submission, Feb. 19, 2013, 5 pages. Web. Accessed Oct. 23, 2017.
Heart and Stroke Foundation of Canada. "Vacuum cleaner sucks up strokes." *ScienceDaily*, Jun. 8, 2010, 4 pages, www.sciencedaily.com/releases/2010/06/100608162240.htm.
Henry, et al. (1999). "Carotid Stenting With Cerebral Protection: First Clinical Experience Using the PercuSurge GuardWire System" J. Endovasc. Surg. 6:321-331.
Hoffer et al. (2003). "Percutaneous Arterial Closure Devices" J. Vasc. Interv. Radiol. 14:865-885.
Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.
Jankowitz, Brian, et al. (2012). "Manual Aspiration Thrombectomy Adjunctive Endovascular Recanalization Technique in Acute Stroke Interventions." *Stroke*, vol. 43, No. 5, pp. 1408-1411.
Koebbe, C. J., E. Veznedaroglu, et al. (2006). "Endovascular management of intracranial aneurysms: current experience and future advances." Neurosurgery 59(5 Suppl 3): S93-102; discussion S3-13.
Kopeck, Rachel. "Penumbra, Inc. Launches 5MAX™ ACE—The Newest Clot Extraction Device to Treat Acute Ischemic Stroke Patients." *Penumbra Inc.*, Jul. 8, 2013, 3 pages, http://www.penumbrainc.com/news/penumbra-inc-launches-5max-ace-the-newest-clot- extraction-device-to-treat-acute-ischemic-stroke-patients/.
Lin et al. (2005) "Protected carotid artery stenting and angioplasty via transfemoral versus transcervical approaches" Vasc. Endovasc. Surg. 39(6):499-503.
Lo et al. (2005) "Advantages and indications of transcervical carotid artery stenting with carotid flow reversal" J. Cardovasc. Surg (Torino). 46(3):229-239.
Luebke, T et al. (2007) "Meta-analysis of randomized trials comparing carotid endarterectomy and endovascular treatment" *Eur. J. Vasc. Endovasc. Surg.* 34:470-479.

(56) References Cited

OTHER PUBLICATIONS

Macdonald, S. (2006) "Is there any evidence that cerebral protection is beneficial?" *J. Cardiovasc. Surg.* 47:127-36.
Mas et al. (2006) "Endarterectomy versus stenting in patients with symptomatic severe carotid stenosis" *NEJM* 355:1660-71.
Matas et al. (2007). "Transcervical carotid stenting with flow reversal protection: Experience in high-risk patients" J. Vasc. Surg. 46:49-54.
Merit Medical Systems Acquired Distal Access's SPINR Platform, Jul. 15, 2015, Digital Access, LLC; Merit Medical Systems, 5 pages. Web. Accessed Oct. 23, 2017.
Mokin, Maxim, et al. (2015). "Primary stentriever versus combined stentriever plus aspiration thrombectomy approaches: in vitro stroke model comparison." Journal of NeuroInterventional Surgery, vol. 7, pp. 453-457.
MomaPresn (AET). Biamino, G. MO.MA as a distal protective device, University of Leipzig, Heart Center Department of Clinical and Interventional, Angiology Leipzig, Germany, 2002. 37 pages.
Nesbit, G. M., G. Luh, et al. (2004). "New and future endovascular treatment strategies for acute ischemic stroke." J Vasc Interv Radiol 15(1 Pt 2): S103-10.
Nii, K., K. Kazekawa, et al. (2006). "Direct carotid puncture for the endovascular treatment of anterior circulation aneurysms." AJNR Am J Neuroradiol 27(7): 1502-4.
Ohki, M.D., et al. (2001). "Efficacy of a proximal occlusion catheter with reversal of flow in the prevention of embolic events during carotid artery stenting: An experimental analysis." J Vasc Surg; 33:504-9.
Ouriel, K., R. K. Greenberg, et al. (2001). "Hemodynamic conditions at the carotid bifurcation during protective common carotid occlusion." J Vasc Surg 34(4): 577-80.
Parodi (2005). "Is flow reversal the best method of protection during carotid stenting?" J Endovasc. Ther. 12:166-170.
Parodi et al. (2000). "Initial evaluation of carotid angioplasty and stenting with three different cerebral protection devices" J. Vasc. Surg. 32:1127-1136.
Parodi, J. C., L. M. Ferreira, et al. (2005). "Cerebral protection during carotid stenting using flow reversal." J Vasc Surg 41(3): 416-22.
Patel, Tejas et al. (2014) "Balloon-Assisted Tracking: A Must-Know Technique to Overcome Difficult Anatomy During Transradial Approach," *Catheter Cardiovasc. Interv.*, 83(2):211-220.
Paullus WS, Pait TG, Rhoton Al Jr. Microsurgical exposure of the petrous portion of the carotid artery. J Neurosurg. 1977;47(5):713-726. (Year: 1977).
Pena, Carlos. "Letter to Sequent Medical Inc Re: K150894, Trade/Device Name: VIA™ 21 Microcatheter." Department of Health & Human Services, Aug. 28, 2015, 14 pages.
Penumbra, Inc., "Penumbra, Inc. Completes Pivotal Stroke Trial of Intracranial Revascularization," Press Release, (2007). Web. Accessed Jun. 14, 2017. 2 pages.
Penumbra, Inc., "The Penumbra Pivotal Stroke Trial: Safety and Effectiveness of a New Generation of Mechanical Devices for Clot Removal in Intracranial Large Vessel Occlusive Disease," *Stroke* 2009, 40:2761-2768. Web. Downloaded Jun. 15, 2017.
Perez-Arjona, E. A., Z. DelProsto, et al. (2004). "Direct percutaneous carotid artery stenting with distal protection: technical case report." Neurol Res 26(3): 338-41.
Pipinos et al. (2005). "Transcervical approach with protective flow reversal for carotid angioplasty and stenting" J. Endovasc. Ther. 12:446-453.
Pipinos et al. (2006). "Transcervical carotid stenting with flow reversal for neuroprotection: Technique, results, advantages, and limitations" 14(5):245-255.
Powers, W.J., et al. (2015, e-published online before print Jun. 29, 2015). "2015 AHA/ASA Focused Update of the 2013 Guidelines for the Early Management of Patients With Acute Ischemic Stroke Regarding Endovascular Treatment: A Guideline for Healthcare Professionals From the American Heart Association/American Stroke Association Powers et al. on behalf of the American Heart Association Stroke Council Stroke." *Stroke*. 46:3020-3035.
Reeder et al., "Aspiration Thrombectomy for Removal of Coronary Thrombus," *American Journal of Cardiology*. (Jul. 1, 1992) 70:107-110 (Abstract only).
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results from a prospective multicenter registry" J. Endovasc. Ther. 12:156-165.
Request for Ex Parte Reexamination Transmittal Form and Request for Ex Parte Reexamination pursuant to 37 CFR 1.150 of U.S. Pat. No. 9,820,761 issued Nov. 21, 2017. Request filed May 11, 2018 and assigned U.S. Appl. No. 90/014,136. 35 pages.
Ribo et al. (2006). "Transcranial doppler monitoring of transcervical carotid stenting with flow reversal protection: a novel carotid revascularization technique" 27:2846-2849 (originally published online Sep. 28, 2006).
Ribo, M., C. Molina, et al. (2008). "Buying Time for Recanalization in Acute Stroke: Arterial Blood Infusion Beyond the Occluding Clot as a Neuroprotective Strategy." J Neuroimaging. 4 pages.
Ross, I. B. and G. D. Luzardo (2006). "Direct access to the carotid circulation by cut down for endovascular neuro-interventions." Surg Neurol 65(2): 207-11; discussion 211.
Saver, J.L. et al. (Jun. 11, 2015, e-published Apr. 17, 2015). "Stent-Retriever Thrombectomy after Intravenous t-PA vs. t-PA Alone in Stroke." *N ENGL J MED*, 372(24):2285-2295.
Seidel, A. et al. (2005). "Relationship between the diameter of great saphenous vein and body mass index," J Vasc Bras, vol. 4, No. 3, p. 265-269.
Simon et al. Hydrodynamic comparison of the Penumbra system and commonly available syringes in forced-suction thrombectomy, J. Neuro Intervent Surg 2014, 6, pp. 205-211. Web. Downloaded Oct. 18, 2017.
Simon, S. et al. (2014, e-published Nov. 14, 2013) "Exploring the efficacy of cyclic vs static aspiration in a cerebral thrombectomy model: an initial proof of concept study." *J. Neurointervent Surg* 6: 677-683. Web. Date accessed Oct. 18, 2017.
Spinnaker® Elite™ Flow Directed Catheters Go with the Flow. Indications for Use. 2 pages. Web. Aug. 27, 2019.
Spinnaker® Elite ™ Flow Directed Catheters Go with the Flow. Promotional Brochure. 1 page. Web. Aug. 27, 2019.
Spiotta et al., Evolution of thrombectomy approaches and devices for acute stroke: a technical review, J. Neuro Intervent Surg 2015, 7, pp. 2-7. Web. Downloaded Oct. 18, 2017.
Stecker et al., (2002). "Stent placement in common carotid and internal carotid artery stenoses with use of an open transcervical approach in a patient with previous endarterectomy" J. Vasc. Interv. Radiol. 13:413-417.
Stejskal, et al. "Experience of 500 Cases of Neurophysiological Monitoring in Carotid Endarterectomy", Acta Neurochir, 2007, 149:681-689.
Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-E259. 6 pages. (http://www.invasivecardiology.com/issue/4284).
Theron, et al. "New Triple Coaxial Catheter System for Carotid Angioplasty with Cerebral Protection" AJNR 11:869-874, Sep./Oct. 1990 0195-6108/90/1106-0869 @ American Society of Neurology.
Trevo ProVue Retriever. Stryker Trevo® ProVue™ Retrieval System (bu Concentric Medical®). (2016) Web. Apr. 13, 2018. 2 pages.
Turk, Aquilla S et al. (2014, e-published Apr. 27, 2013) "Initial clinical experience with the ADAPT technique: A direct aspiration first pass technique for stroke thrombectomy." J NeuroIntervent Surg 2014;6:231-237. doi: 10.1136/neurintsurg-2013-010713. Web. Accessed Sep. 26, 2018.
Vijaywargiya et al "Anatomical study of petrous and cavernous parts of internal carotid artery". Anatomy and Cell Biology 2017;50: 163-170. (Year: 2017).
Webb et al, "Retrieval and Analysis of Particulate Debris After Saphenous Vein Graft Intervention," *Journal of the American College of Cardiology*, 34(2);468-475 (1999).

(56) References Cited

OTHER PUBLICATIONS

Yoo et al., "The Penumbra Stroke System: a technical review." *Journal of NeuroInterventional Surgery*. 4:199-205 (2012). Web. Downloaded Jun. 15, 2017.
Zuckerman, Bram. "Letter to Cathera Inc: Re K151638, Trade/ Device Name: Phenom™ Catheters." Department of Health & Human Services, Nov. 13, 2015, 6 pages.
U.S. Appl. No. 16/584,351, filed Sep. 26, 2019, US 2020-0038628.
U.S. Appl. No. 16/596,535, filed Oct. 8, 2019, US 2020-0046940.
U.S. Appl. No. 16/925,708, filed Jul. 10, 2020, US 2020-0337716.
U.S. Appl. No. 17/011,448, filed Sep. 3, 2020, US 2021-0052296.
U.S. Appl. No. 17/481,639, filed Sep. 22, 2021, US 2022-0175565.
U.S. Appl. No. 17/545,885, filed Dec. 8, 2021, US 2022-0096103.
U.S. Appl. No. 17/883,295, filed Aug. 8, 2022, US 2022-0370767.
U.S. Appl. No. 18/297,429, filed Apr. 7, 2023, US 2023-0241347.
U.S. Appl. No. 18/297,450, filed Apr. 7, 2023, US 2023-0263995.
PCT/US2023/20868, May 3, 2023, WO 2023/215402.
PCT/US2023/20871, May 3, 2023, WO 2023/215403.
PCT/US2023/23574, May 3, 2023, WO 2023/230259.
PCT/US2023/64454, Mar. 15, 2023, WO 2023/178189.
Chueh, J.Y. et al. (2013). "Reduction in Distal Emboli with Proximal Flow Control During Mechanical Thrombectomy." Stroke, 44(5), 1396-1401.
Halbach, V.V. et al. (1991). "Management of vascular perforations that occur during neurointerventional procedures." AJNR. American Journal of Neuroradiology, 12(2), 319-327.
Jauch, E.C. et al. (2013). American Heart Association Stroke Council, Council on Cardiovascular Nursing, Council on Peripheral Vascular Disease, & Council on Clinical Cardiology. Guidelines for the early management of patients with acute ischemic stroke: a guideline for healthcare professionals from the American Heart Association/American Stroke Association. Stroke, 44(3), 870-947.
Merci Retrieval System® L Series Animation [Video]. (Mar. 14, 2013). StrokeInfo. YouTube. http://www.youtube.com/embed/9BEH8xzLRSs?wmode=transparent&fs=1&hl=en&modestbranding=1&showsearch=0&rel=0&theme=darkretrieved. Wayback Machine http://web.archive.org/web/20130314142314/http:/www.youtube.com/embed/9BEH8xzLRSs?wmode=transparent&fs=1&hl=en&modestbranding=1&showsearch=0&rel=0&theme=dark , retrieved on May 7, 2025. 2 pages.
Merci® Retrieval Systen. (2006). Concentric Medical. 2 pages. Archived at https://web.archive.org/web/20061107161134/http://www.concentric-medical.com/pdfs/APM0126_A_OUS%20Spec%20Sheet%202006-05.pdf, retrieved on May 7, 2025.
Penumbra, Inc., "5Max™: Direct Aspiration TM Enables Choice," Marketing Brochure © 2013 (4 pages).
Stryker Signs Definitive Agreement to Acquire Concentric Medical, Inc. (Aug. 31, 2011). PR Newswire. https://www.prnewswire.com/news-releases/stryker-signs-definitive-agreement-to-acquire-concentric-medical-inc-128833048.html. Archived Wayback Machine Sep. 26, 2011 http://web.archive.org/web/20110926112841/https:/www.prnewswire.com/news-releases/stryker-signs-definitive-agreement-to-acquire-concentric-medical-inc-128833048.html, retrieved on May 7, 2025. 3 pages.
Yuki et al. (2012). "The Impact of Thromboemboli Histology on the Performance of a Mechanical Thrombectomy Device." AJNR. American Journal of Neuroradiology, 33(4), 643-648.

* cited by examiner 100
200
300
238
236
234
233
232
240
226
228
230
220
222
224
254
250
252
256
264
270
334
330
332
320
326
328
322
324
348
340
343
344
346
400
500
510
350

RAPID ASPIRATION THROMBECTOMY SYSTEM AND METHOD

CROSS-REFERENCE TO RELATED APPLICATIONS

This application is a continuation of U.S. patent application Ser. No. 16/596,535, filed Oct. 8, 2019, which is a continuation of U.S. patent application Ser. No. 15/856,979, filed Dec. 28, 2017, now U.S. Pat. No. 10,456,555, issued Oct. 29, 2019, which is a continuation of U.S. application Ser. No. 15/805,673, filed Nov. 7, 2017, now U.S. Pat. No. 10,485,952, issued Nov. 26, 2019, which is a continuation of U.S. application Ser. No. 15/015,799, filed Feb. 4, 2016, now U.S. Pat. No. 9,820,761, issued Nov. 21, 2017, which claims priority to U.S. Provisional Application Ser. No. 62/111,841, filed Feb. 4, 2015, and U.S. Provisional Application Ser. No. 62/142,637, filed Apr. 3, 2015, the disclosures are each incorporated by reference herein in their entireties.

This application is also related to the following U.S. patent applications, which are incorporated by reference in their entirety: (1) U.S. patent application Ser. No. 14/576,953, filed Dec. 19, 2014; and (2) U.S. patent application Ser. No. 14/569,365, filed Dec. 12, 2014; (3) U.S. patent application Ser. No. 14/537,316, filed Nov. 10, 2014; (4) U.S. patent application Ser. No. 14/221,917, filed Mar. 21, 2014, which are all incorporated by reference.

BACKGROUND

The present disclosure relates generally to medical methods and devices for the treatment of acute ischemic stroke. More particularly, the present disclosure relates to methods and systems for navigating complex anatomy to perform rapid and safe aspiration and removal of cerebral occlusions.

Acute ischemic stroke is the sudden blockage of adequate blood flow to a section of the brain, usually caused by thrombus or other emboli lodging or forming in one of the blood vessels supplying the brain. If this blockage is not quickly resolved, the ischemia may lead to permanent neurologic deficit or death. The timeframe for effective treatment of stroke is within 3 hours for intravenous (IV) thrombolytic therapy and 6 hours for site-directed intra-arterial thrombolytic therapy or up to 8 hours for interventional recanalization of a blocked cerebral artery. Re-perfusing the ischemic brain after this time period has no overall benefit to the patient, and may in fact cause harm due to the increased risk of intracranial hemorrhage from fibrinolytic use. Even within this time period, there is strong evidence that the shorter the time period between onset of symptoms and treatment, the better the results. Unfortunately, the ability to recognize symptoms, deliver patients to stroke treatment sites, and finally to treat these patients within this timeframe is rare. Despite treatment advances, stroke remains the third leading cause of death and the leading cause of serious, long-term disability in the United States.

Endovascular treatment of acute stroke is comprised of either the intra-arterial administration of thrombolytic drugs such as recombinant tissue plasminogen activator (rtPA), mechanical removal of the blockage, or a combination of the two. As mentioned above, these interventional treatments must occur within hours of the onset of symptoms. Both intra-arterial (IA) thrombolytic therapy and interventional thrombectomy involve accessing the blocked cerebral artery via endovascular techniques and devices.

Like IV thrombolytic therapy, IA thrombolytic therapy alone has the limitation in that it may take several hours of infusion to effectively dissolve the clot. Interventional thrombectomy therapies have involved capturing and removing the clot using snares, coils or temporary stents (also known as retrievable stent devices), and suctioning the clot with or without adjunct disruption of the clot. Retrievable stent devices are also utilized to restore flow quickly to the vessel during the intervention. Hybrid procedures are also utilized, combining retrievable stent devices and aspiration via the guide catheter or via intermediate catheters to aid in the removal of the clot and reduce the risk of distal emboli. Finally, balloons or stents have been used to create a patent lumen through the clot when clot removal or dissolution was not possible.

To access the cerebral anatomy, guide catheters or guide sheaths are used to guide interventional devices to the target anatomy from an arterial access site, typically the femoral artery. Balloon guide catheters are often used to enable proximal carotid artery occlusion during periods of the procedure which may potentially liberate a high level of emboli. The proximal occlusion has the effect of arresting forward flow and increasing aspiration efficiency through the lumen of the guide catheter. The length of the guide is determined by the distance between the access site and the desired location of the guide distal tip. Interventional devices such as guidewires, microcatheters, and intermediate catheters used for sub-selective guides and aspiration, are inserted through the guide and advanced to the target site. Often, devices are used in a co-axial fashion, namely, a guidewire inside a microcatheter inside an intermediate catheter is advanced as an assembly to the target site in a stepwise fashion with the inner, most atraumatic elements, advancing distally first and providing support for advancement of the outer elements. The length of each element of the coaxial assemblage takes into account the length of the guide, the length of proximal connectors on the catheters, and the length needed to extend from the distal end. Thus, for example, the working length of an intermediate catheter is typically 20-40 cm longer than the working length of a guide, and the working length of a microcatheter is typically 10-30 cm longer than the working length of the intermediate catheter. The guidewire is typically longer than the microcatheter by another 20-50 cm.

Some exemplary issues with current technology include the time required or even the ability to access the site of the occlusion, the time required to restore flow or the inability to fully, or even partially, restore flow to the vessel, the occurrence of distal emboli during the procedure, which has potentially negative neurologic effect and procedural complications such as perforation and intracerebral hemorrhage. There is a need for a system of devices and methods that enable rapid access, optimized aspiration of the clot, distal protection throughout all stages of the procedure, which potentially liberate emboli, and safe and rapid exchange of devices as needed to fully restore flow to the blocked cerebral vessel.

SUMMARY

In one aspect, there is disclosed an intravascular access system for facilitation of intraluminal medical procedures within the neurovasculature through an access sheath. The system includes an aspiration or support catheter having a flexible, distal luminal portion having an inner diameter defining a lumen extending between a proximal opening at a proximal end of the luminal portion and a distal opening at a distal end of the luminal portion. The catheter has a rigid spine coupled to at least the proximal end of the luminal portion and extending proximally therefrom. The system includes a dilator having a flexible, distal dilator portion sized to be received within the lumen of the luminal portion; and a rigid, dilator spine extending proximally from the dilator portion.

The dilator spine can align side-by-side with the spine of the catheter. The distal dilator portion can have a tapered distal tip. The dilator can have a length at least as long as a length of the catheter such that a distal tip of the dilator protrudes from the distal opening of the luminal portion. The dilator can be generally tubular along at least a portion of the length. A proximal end of the catheter spine can include a gripping feature configured for a user to grasp in order to move the catheter through an access sheath. A proximal end of the dilator spine can include a tab configured to be locked with the gripping feature on the catheter spine. When the catheter and the dilator are in a locked configuration they can be advanced as a single unit through the access sheath. The gripping feature and the dilator tab can be removably coupled such that in a locked configuration the dilator tab engages the gripping feature and in an unlocked configuration the dilator tab disengages from the gripping feature. The dilator tab can be affixed to the dilator or can be slideable on the dilator to accommodate different relative positions between the dilator and the catheter. The distal dilator portion can include one or more detents on an outer surface configured to lock with correspondingly-shaped surface features on an inner surface of the luminal portion lumen through which the dilator portion extends. The dilator spine and the catheter spine can have a similar stiffness and kink-resistance. The dilator can have a visual marker on a distal end and/or a proximal end of the distal tip. A distal end region of the dilator can be more flexible and increasingly stiffen towards a proximal end region of the dilator. The catheter spine and dilator spine can be configured to cause bi-directional sliding movement of the luminal portion through a lumen of an access sheath and navigate the luminal portion into a cerebral vessel to reach a treatment site.

In an interrelated aspect, disclosed is an intravascular access system for facilitation of intraluminal medical procedures within the neurovasculature having an access sheath and an aspiration or support catheter. The access sheath has a sheath body having an inner diameter defining a lumen between a proximal end and a distal end of the sheath body. The sheath body has at least one opening from the lumen near a distal end region of the sheath body. The aspiration or support catheter includes a flexible, distal luminal portion having an outer diameter sized for insertion through the lumen of the access sheath, an inner diameter defining a lumen extending between a proximal opening at a proximal end of the luminal portion and a distal opening at a distal end of the luminal portion, and a length between the proximal opening and the distal opening. The aspiration or support catheter includes a rigid spine coupled to at least the proximal end of the luminal portion and extending proximally therefrom. The rigid spine is configured to cause bi-directional sliding movement of the luminal portion through the lumen of the access sheath and out the at least one opening to navigate the luminal portion into a cerebral vessel to reach a treatment site. A portion of the outer diameter of the luminal portion fluidly seals with the inner diameter of the access sheath when the distal end of the luminal portion extends into the cerebral vessel to reach the treatment site.

The luminal portion and the sheath body can be concentrically aligned and the lumen of the luminal portion and the lumen of the sheath body form a contiguous aspiration lumen from the distal end of the luminal portion to the proximal end of the sheath body. The contiguous aspiration lumen can be used to aspirate fluid and debris from the distal opening of the luminal portion. The contiguous aspiration lumen can be to deliver materials through the distal opening of the luminal portion. The contiguous aspiration lumen can form a step-up in diameter where the lumen of the luminal portion empties into the lumen of the sheath body. The lumen of the luminal portion can be shorter than the lumen of the sheath body. The luminal portion and the sheath body can form an overlap region when the luminal portion extends distally beyond the at least one opening of the sheath body. The outer diameter of the luminal portion can approach the inner diameter of the lumen of the sheath body such that a seal is formed by the overlap region. The seal can be configured to enable sealing against a vacuum of up to 25 inHg, or up to 28 inHg. The seal within the overlap region can be configured to enable sealing against a pressure of up to 300 mmHg or up to 600 or up to 700 mmHg. The seal can be located distal a proximal end of the luminal portion and proximal to the at least one opening of the sheath body.

The system can further include a sealing element positioned on an external surface of the luminal portion. The sealing element can include a stepped up diameter or protruding feature in the overlap region. The sealing element can include one or more external ridge features. The one or more ridge features can be compressible when the luminal portion is inserted into the lumen of the sheath body. The sealing element can include one or more inclined surfaces biased against an inner surface of the sheath body lumen. The sealing element can include one or more expandable members actuated to seal. The sheath body can have an outer diameter suitable for insertion into the carotid artery. The outer diameter of the sheath body can be between 5Fr and 7Fr.

The sheath body can have a length between the proximal end and the distal end suitable for locating the distal end of the sheath body at the petrous portion of an internal carotid artery from a transfemoral approach. The length of the sheath body can be between 80 cm and 105 cm. The length of the luminal portion can be between 10 cm and 25 cm. The length of the luminal portion can be less than a length of the sheath body such that as the catheter is retracted into the sheath body a seal remains between an overlap region of the luminal portion and the inner diameter of the sheath body.

The spine can be longer than an entire length of the sheath body. The luminal portion can include three or more layers including an inner lubricious liner, a reinforcement layer, and an outer jacket layer. The outer jacket layer can be composed of discreet sections of polymer with different durometers, compositions, and/or thicknesses to vary the flexibility along the length of the distal luminal portion. The outer diameter of the distal luminal portion can be sized for navigation into cerebral arteries. The inner diameter of the distal luminal portion can be between 0.040" and 0.088". The outer diameter of the luminal portion can approach the inner diameter of the sheath body creating a sealed area at an overlap region while still allowing the catheter to move through the sheath body. The catheter can be tapered towards the distal opening such that a distal-most end of the luminal portion has a smaller outer diameter compared to a more proximal region of the luminal portion near where the luminal portion seals with the sheath body. The distal end region of the sheath body can include an occlusion element.

The distal end region of the sheath body can include an expanding distal tip. The at least one opening from the lumen can include a side opening located a distance away from a distal tip of the sheath body. The distal tip of the sheath body further can include a ramp feature configured to direct at an angulation the catheter away from a longitudinal axis of the sheath body lumen out through the at least one opening.

The spine can be longer than an entire length of the sheath body. The spine can be a wire having an outer dimension from 0.014" to 0.018". The spine can be a hypotube having a guide-wire passageway extending therethrough. The spine can be a ribbon having an outer dimension from 0.010" to 0.025" thick. The ribbon can be curved along at least a portion of an arc. The spine can be configured to rotate the luminal portion around a longitudinal axis of the access sheath. The spine can be eccentrically coupled to the luminal portion and the spine extend proximally from the luminal portion to outside the proximal end of the sheath body. The proximal end of the luminal portion can have an angled cut. The angled cut can be generally planar or curved. The sheath body can have one or more visual markers on the distal end region of the sheath body. The distal luminal portion can have one or more visual markers at a distal end region of the luminal portion, a proximal end region of the luminal portion or both. The one or more visual markers on the sheath body and the one or more visual markers on the luminal portion can be visually distinct. The spine can have one or more visual markers. The one or more visual markers of the spine can indicate overlap between the distal luminal portion and the sheath body. The one or more visual markers of the spine can be positioned so that when the visual marker of the spine is aligned with a portion of the access sheath, the catheter is positioned at a distal-most position with minimal overlap length needed to create a seal between the catheter and the sheath body.

The system can further include a dilator having a flexible, distal dilator portion having a distal tip and sized to be received within the luminal portion of the catheter. The dilator can be a tubular element along at least a portion of its length. The dilator can be a solid rod formed of malleable material configured to be shaped by a user. The dilator can further include a rigid, dilator spine extending proximally from the dilator portion. The dilator spine can be coaxial and can have a lumen extending through it. The dilator spine can be eccentric. When in use, the dilator spine can align side-by-side with the spine of the catheter. The distal tip of the dilator can be tapered. The dilator can have a length at least as long as a length of the catheter such that the distal tip protrudes from the distal opening of the luminal portion. A proximal end of the spine can include a gripping feature configured for a user to grasp in order to move the catheter through the access sheath. A proximal end of the dilator spine can include a tab configured to be locked with the gripping feature on the catheter spine. When the catheter and dilator are in a locked configuration they can be advanced as a single unit through the sheath body. The gripping feature and the dilator tab can be removably coupled such that in a locked configuration the dilator tab engages the gripping feature and in an unlocked configuration the dilator tab disengages from the gripping feature. The dilator tab can be affixed to the dilator and/or can be slideable on the dilator to accommodate different relative positions between the dilator and the catheter.

The distal dilator portion can include one or more detents on an outer surface configured to lock with correspondingly-shaped surface features on an inner surface of the luminal portion lumen through which the dilator portion extends. The dilator spine and the catheter spine can have a similar stiffness and kink-resistance. The dilator can have a visual marker on a distal end and/or a proximal end of the distal tip. A distal end region of the dilator can be more flexible and increasingly stiffens towards the proximal end region of the dilator.

The access sheath can further include a connector that connects the proximal end of the sheath body to a proximal hemostasis valve. The proximal hemostasis valve can have an adjustable opening sized large enough to allow removal of the catheter without dislodging any clots thereon. When in use with the access sheath, the rigid spine of the catheter can extend proximally from the luminal portion through the access sheath lumen and out the proximal hemostasis valve of the access sheath. The connector can provide a connection of the proximal end of the sheath body to an aspiration line. The connector can have a large bore inner lumen and connects to a large-bore aspiration line. The aspiration line can connect to an aspiration source. The aspiration source can be an active aspiration source. The aspiration line can connect to a forward drip or flush line. The access sheath can further include a proximal extension portion such that when the distal luminal portion of the catheter is withdrawn from the sheath body lumen it remains within the proximal extension portion. The inner diameter of the luminal portion can be sized to permit placement of an interventional device through the luminal portion.

Other features and advantages should be apparent from the following description of various implementations, which illustrate, by way of example, the principles of the invention.

DETAILED DESCRIPTION

Figure 1:
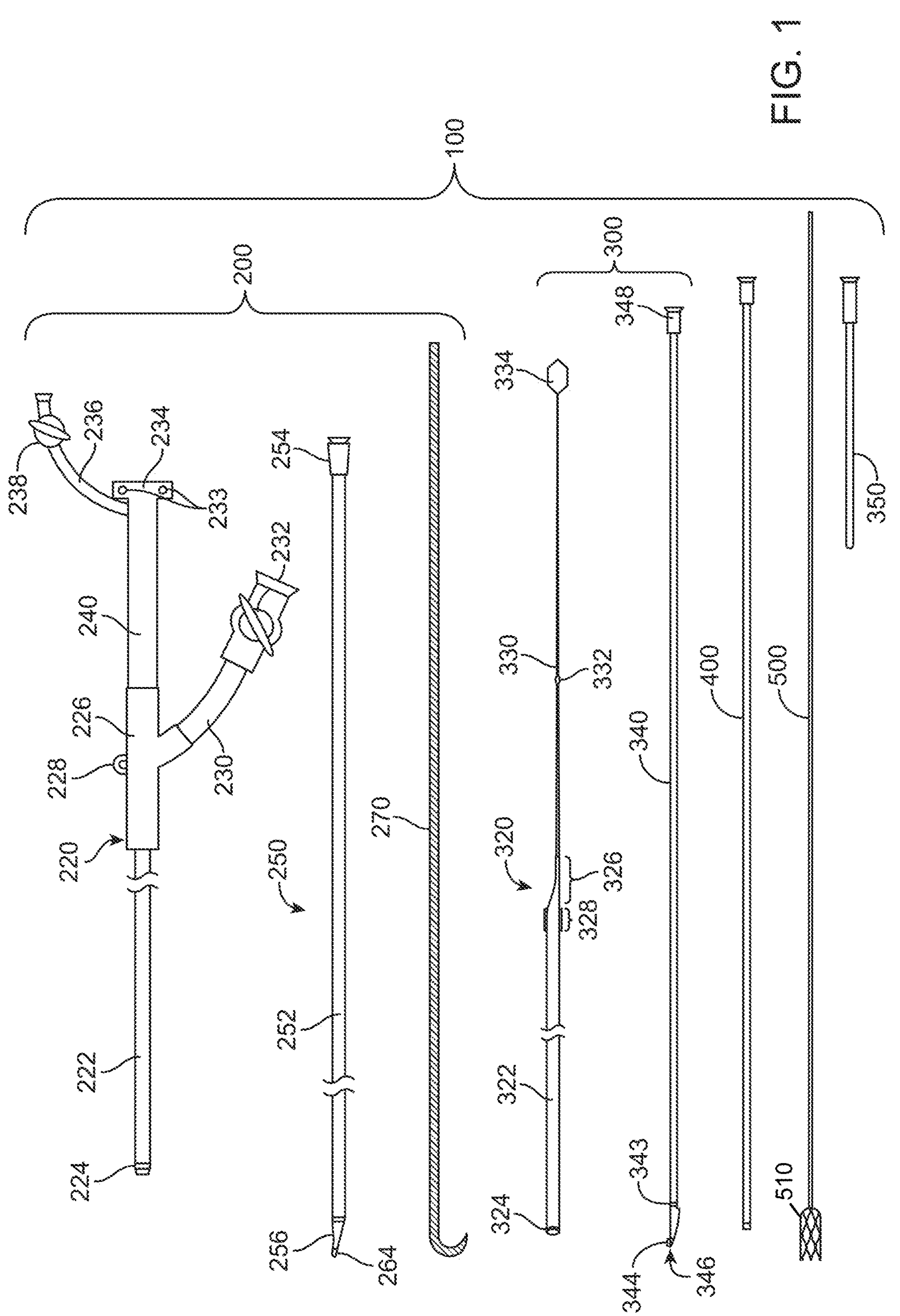
FIG. 1 is an exploded view of a system of devices for accessing and removing a cerebral occlusion to treat acute ischemic stroke from a femoral artery access site.

One of the major drawbacks to current acute stroke intervention procedures is the amount of time required to restore blood perfusion to the brain. This time includes the time it takes to access the occlusive site or sites in the cerebral artery, and the time it takes to completely remove the occlusion in the artery. Because it is often the case that more than one attempt must be made to completely remove the occlusion, reducing the number of attempts as well as reducing the time required to exchange devices for additional attempts is an important factor in minimizing the overall time. Additionally, each attempt is associated with potential procedural risk due to device advancement in the delicate cerebral vasculature.

Disclosed herein are methods and devices that enable safe and rapid access to the complex neurovascular anatomies of the cerebral and intracranial arteries and removal of the occlusion. The methods and devices include one or more access devices, catheters, and thrombectomy devices to remove the occlusion. Methods and devices are also disclosed to provide active aspiration and/or passive flow reversal for the purpose of facilitating removal of the occlusion as well as minimizing distal emboli. The system offers the user a degree of flow control so as to address the specific hemodynamic requirements of the cerebral vasculature. The systems described herein provide superior ease of use in that a single operator may operate the disclosed systems using single-point continuous aspiration for rapid and safe exchange without switching. The higher efficiency of aspiration force through the systems described herein reduces distal embolic debris and increases the rate of "one-pass" thrombectomy.

It should be appreciated that while some embodiments are described with specific regard to aspirating a neurovascular anatomy, the embodiments are not so limited and may also be applicable to other uses. For example, the spined aspiration catheter and one or more components of the access systems described herein may be used to deliver working devices to a target vessel of a coronary anatomy, or other vasculature anatomy. It should be appreciated that where the phrase "aspiration catheter" is used herein that such a catheter may be used for other purposes besides or in addition to aspiration, such as the delivery of fluids to a treatment site or as a support catheter providing a conduit that facilitates and guides the delivery or exchange of other devices such as a guidewire or interventional devices. Alternatively, the access systems need not be limited only to the vasculature can be useful for access of other parts of the body outside the vasculature. It should also be appreciated that reference throughout this specification to a particular feature, structure, configuration, characteristic or implementation or embodiment may be combined in any suitable manner. The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various embodiments below.

FIG. 1 shows a system of devices for accessing and removing a cerebral occlusion to treat acute ischemic stroke from a femoral artery access site. The system 100 includes an access sheath 220, sheath dilator 250, guidewire 270, one or more spined aspiration or support catheters 320, dilator 340, microcatheter 400, and a retrievable stent device 500, each of which will be described in more detail below. Further, the system 100 can include one or more arterial access sheath system 200 that includes an access sheath 220, one or more sheath dilators 250 and a sheath guidewire 270. The system 100 can include one or more spined catheter systems 300 including a spined aspiration or support catheter 320, a tapered dilator 340, and alternatively a catheter clearing tool 350. The spine catheter system 300 can incorporate nested spined catheters to provide for extended reach into distal sites. The system 100 can include an access sheath system 200, a tapered catheter system 300, a microcatheter 400, and a retrievable stent device 500.

Figure 2A:
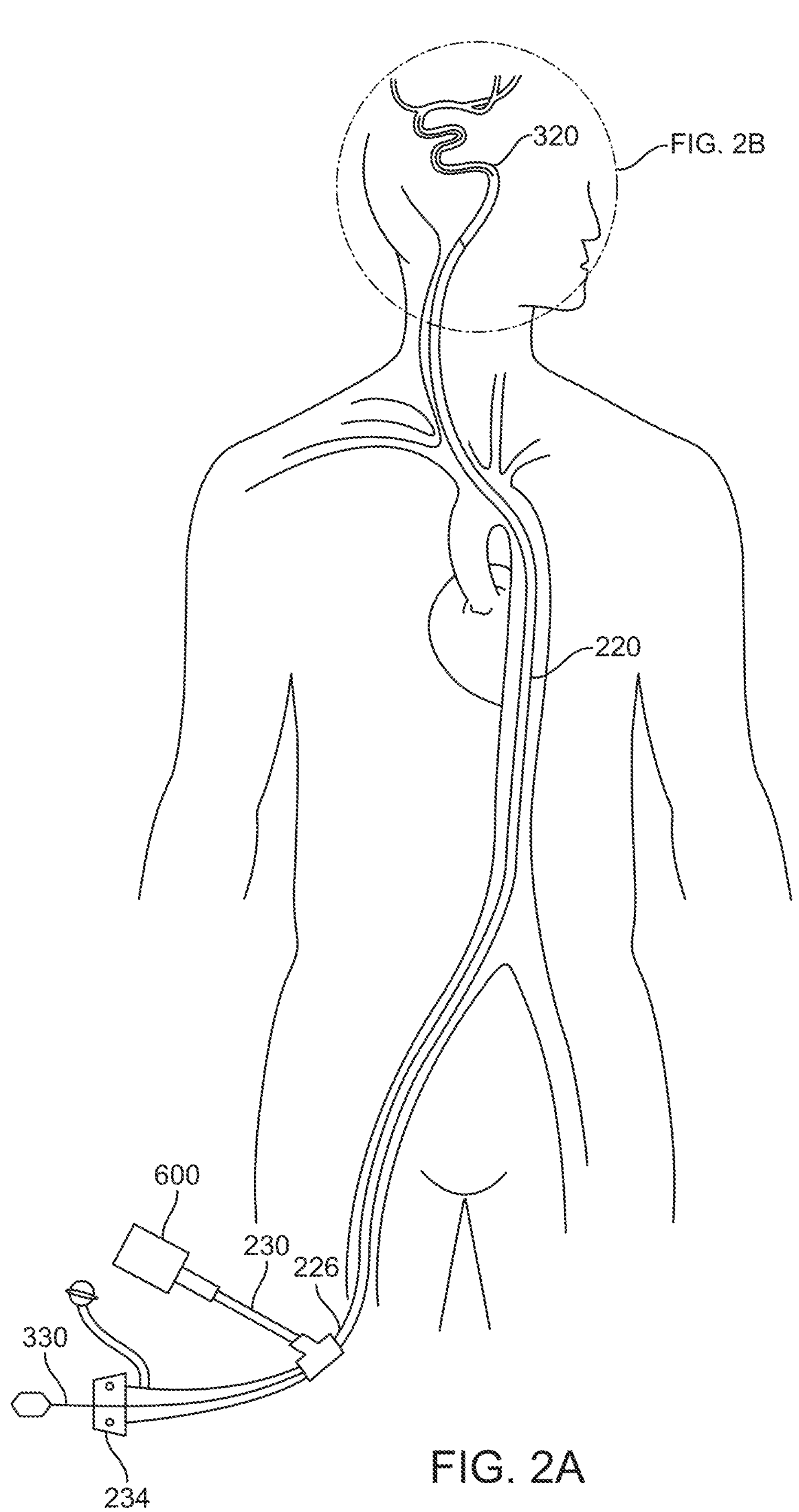
FIG. 2A shows components of the system of FIG. 1 in position in a patient from the transfemoral approach to treat the occlusion.

FIG. 2A shows some elements of the system in position in the patient from the transfemoral approach to treat the occlusion. The access sheath 220 can be inserted through a femoral artery insertion site positioned with the distal tip of the access sheath 220 at or near the petrous portion of the internal carotid artery ICA. The spined aspiration catheter 320 can be positioned with the distal tip at the face of the occlusion in the artery. In some implementations, the access sheath 220 can be inserted through a direct puncture in the wall of the common carotid artery and advanced into the internal carotid artery rather than via a transfemoral approach (see FIG. 3).

Figure 2B:
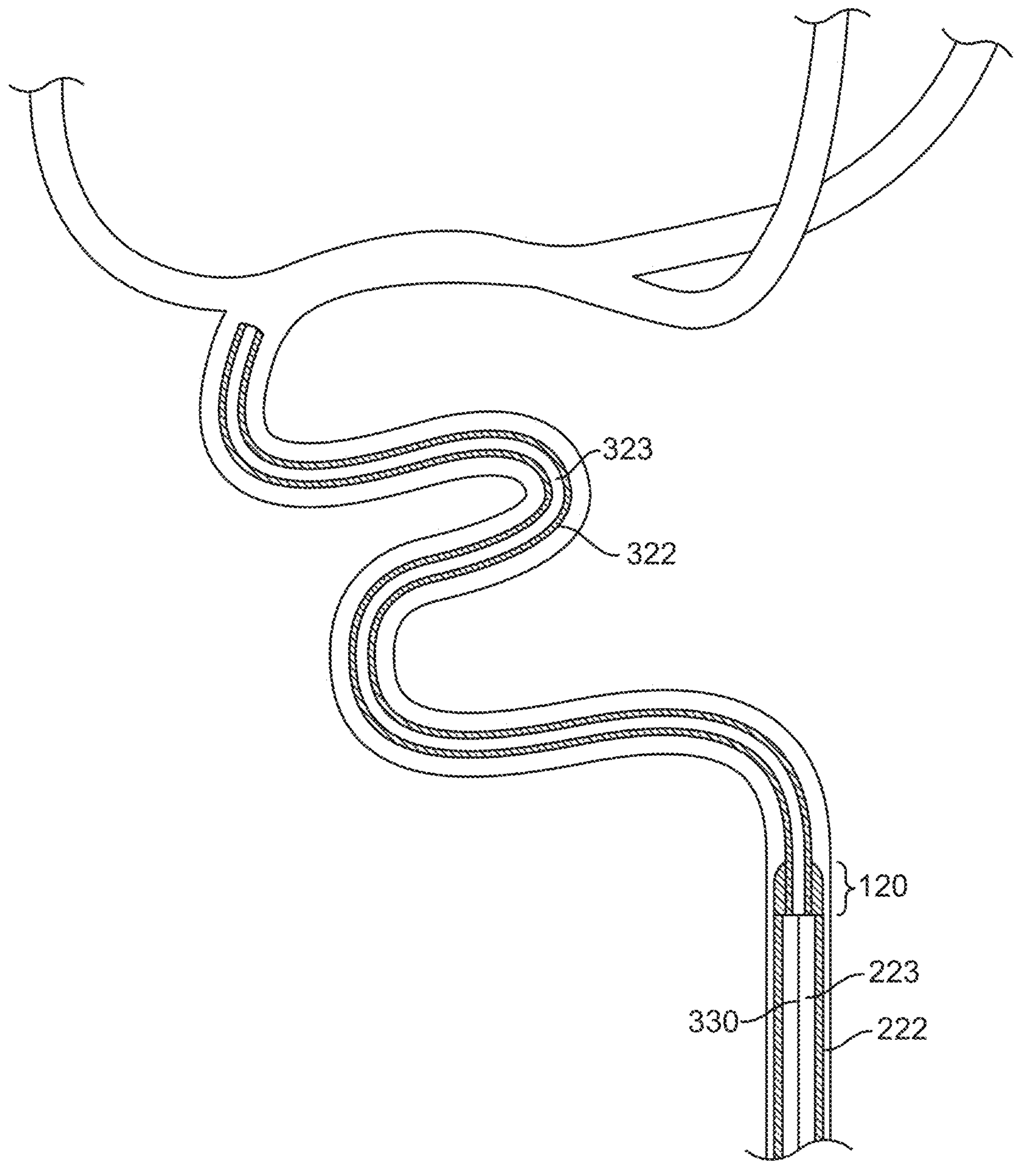
FIG. 2B is a detailed view of a portion of the system of FIG. 2A taken along circle BB.

As seen more clearly in detailed FIG. 2B, the access sheath 220 can have a sheath body 222 and an inner lumen 223 extending between a proximal end and a distal end region of the sheath body 222. The spined aspiration catheter 320 is sized to extend through the inner lumen 223 of the access sheath 220 such that a distal end region of the catheter 320 extends beyond a distal end region of the access sheath 220. The catheter 320 is shown in FIG. 2B exiting the lumen 223 of the sheath body 222 through a distal opening 221. It should be appreciated, however, that the sheath body 222 may have one or more side openings near a distal end region of the body 222 through which the catheter 320 can extend (see FIG. 12C) as will be described in more detail below.

Still with respect to FIG. 2B, the spined aspiration catheter 320 can include a relatively flexible, distal luminal portion 322 coupled to a stiff and kink-resistant proximal spine 330. The distal luminal portion 322 can have an inner lumen 323 extending between a proximal end and a distal end of the luminal portion 322. The lumen 323 of the catheter 320 can have a first inner diameter and the lumen 223 of the access sheath 220 can have a second, larger inner diameter. The lumens 223, 323 are fluidly connected and contiguous such that fluid flow into and/or out of the system is possible, such as by applying suction from an aspiration source coupled to the system via a connector 226 on the access sheath 220. An overlap region 120 between the distal section of the sheath body 222 and the luminal portion 322 of the catheter 320 is sized and configured to create a seal that enables a continuous aspiration lumen from the distal tip region of the spined catheter 320 to the proximal sheath connector 226. If the sheath body 222 has a side opening through which the distal luminal portion 322 of the catheter 320 extends, the seal created at the overlap region 120 between the sheath body 222 and the luminal portion 322 is located proximal to the side opening.

Key dimensions that affect aspiration force through a tube include radius (r), pressure (P), viscosity (n) and length (L) where Flow=$Q=\pi r^4(\Delta P)/8\ nL$. Changes in radius increase flow to the $4^{th}$ power and length is inversely proportional to flow. As will be described in more detail below, the aspiration catheter has an over-the-wire portion that is a fraction of the overall distance required to reach the target site. This configuration greatly speeds up the time required to retract and re-advance the catheter. Further, the systems described herein can provide for a markedly increased radius and luminal area for aspiration of the clot and markedly shorter length, particularly compared to prior systems where the aspiration lumen runs along the entire inner diameter of the aspiration catheter. In the systems described herein, the majority of the aspiration lumen has a radius of the procedural sheath. The catheter 320 is smaller in diameter than the guide, but steps up in luminal diameter upon reaching the lumen of the access sheath 220 allowing for a greater aspiration force to be applied to a majority of the length of the luminal system. Further, the overall length of this narrow diameter region of the catheter 320 is much shorter compared to the overall length of the access sheath. The proximal spine 330 of the catheter 320 has a length and structure that extends through the lumen 223 of the access sheath 220 to a proximal end of the system such that it can be used to advance and retract the catheter 320 through the lumen 223 of the sheath 220. The spine 330 of the aspiration catheter 320, however, takes up only a fraction of the luminal space the system resulting in increased luminal area for aspiration. Increased luminal area for aspiration increases the time it takes to aspirate the occlusion and increases the possibility of removing the occlusion in a single aspiration attempt. The stepped up luminal diameter also increases the annular area available for forward flushing of contrast, saline, or other solutions while devices such as microcatheters or tapered dilators are coaxially positioned in the spined catheter 320 and access sheath 220. This can increase the ease and ability to perform angiograms during device navigation.

Current stroke interventions pose a risk of distal emboli being released. During the effort to remove or dissolve clot blockages in the cerebral artery, for example, there is a significant risk of thrombus fragmentation creating embolic particles that can migrate downstream into either the occluded vessel or other vessels and compromise cerebral perfusion. In carotid artery stenting procedures (CAS), embolic protection devices and systems are commonly used to reduce the risk of embolic material from entering the cerebral vasculature. The types of devices include intravascular distal filters, and reverse flow or static flow systems. Unfortunately, because of the delicate anatomy and access challenges as well as the need for rapid intervention, these types of embolic protection systems are not used in interventional treatment of acute ischemic stroke. The period of a stroke intervention when flow is restored is normally considered an important time as the brain is now being perfused by blood. However, it is also a period of embolic risk. While there is blockage in the artery, there is no flow. Therefore any embolic debris created by crossing the occlusion with guidewire and/or microcatheter, or deployment of a retrievable stent device across the occlusion, remains stagnant. However, when flow is restored to the artery, the emboli can now flow antegrade to distal vascular territories.

A second period of embolic risk occurs when the retrievable stent device is being pulled back into the guide or catheter. In prior methods and devices, aspiration is applied to the intermediate catheter during retrievable stent device retraction into the catheter, or the catheter and retrievable stent device are pulled back together into the guide, while simultaneously applying aspiration to the guide catheter. Two points of aspiration, through the catheter and through the guide, may both be utilized to reduce risk of distal emboli during the critical step of drawing the occlusion through the guide and out of the patient. Often, two people are required to enable two points of aspiration, or aspiration is performed sequentially from first the catheter and then the guide, which may lead to interruption in aspiration or sub-optimal aspiration. In the disclosed systems and methods, reverse flow may be applied to the target site during device advancement, at the critical time of flow restoration, and during the entire time that the occlusion is being removed, with a single point of aspiration.

In an aspect of the disclosure, the level of aspiration may be modified from a low level to achieve adequate protection from distal emboli, to a higher level to provide effective aspiration removal of the occlusion. This aspect allows distal protection without high levels of blood loss, yet allows a strong aspiration force as needed to remove the occlusion.

In another aspect, there are disclosed methods and devices for additionally providing active aspiration or passive retrograde flow during the procedure to remove thrombus and to minimize distal emboli. The system offers the user a degree of blood flow control so as to address the specific hemodynamic requirements of the cerebral vasculature. The system may include a flow controller, which allows the user to control the timing and mode of aspiration.

In another aspect, there are disclosed methods and devices for additionally providing flushing steps to minimize emboli entrapment in the system and increased visibility of particulates in the system during use.

The following descriptions provide detailed implementations and benefits of each aspect of the disclosed invention.

Referring again to FIG. 1 illustrating an implementation of an access sheath 220. The sheath 220 can include a sheath body 222 that is the insertable portion of the sheath 220 (i.e. the portion that inserts into the patient), a proximal connector 226, an aspiration line 230, a proximal hemostasis valve 234 and a flush line 236. The sheath 220 may also include a proximal extension portion 240, and may also include a valve on the connector 226 to fluidly isolate the sheath body 222 from the proximal portion 240 of the access sheath 220. The access sheath 220 may come in a kit with one or more dilators 250, and a sheath guidewire 270.

The diameter of the sheath body 222 is suitable for insertion into the carotid artery, with an inner lumen 223 that is suitably sized for providing a passageway for catheters to treat the occlusion. In an implementation, the sheath body 222 can have an inner diameter of about 0.074" and an outer diameter of about 0.090", corresponding to a 5 French sheath size, an inner diameter of about 0.087" and an outer diameter of about 0.104", corresponding to a 6 French sheath size, or an inner diameter of about 0.100" and an outer diameter of about 0.177", corresponding to a 7 French sheath size. The length of the sheath body 222 is configured to enable the distal tip of the sheath body 222 to be positioned as far distal as the petrous portion of the internal carotid artery. In an implementation, the sheath body 222 length is suitable for a transfemoral approach, in the range 80 to 90 cm or up to about 100 cm or up to about 105 cm. In an implementation, the sheath body 222 length is suitable for a transcarotid approach to the petrous ICA, in the range 20 to 25 cm. In an implementation, the sheath body 222 length is suitable for a transcarotid approach to the CCA or proximal ICA, in the range 10-15 cm. The sheath body 222 is configured to assume and navigate the bends of the vasculature and be subject to high aspiration forces without kinking, collapsing, or causing vascular trauma.

The sheath body 222 can be constructed in two or more layers. An inner liner can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liner and may be constructed from materials such as PEBAX, thermoplastic polyurethane, polyethylene, nylon, or the like. A third layer can be incorporated that can provide reinforcement between the inner liner and the outer jacket. The reinforcement layer can prevent flattening or kinking of the inner lumen of the sheath body 222 to allow unimpeded device navigation through bends in the vasculature as well as aspiration or reverse flow. The sheath body 222 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another implementation, the reinforcement layer can be a cut hypotube such as a Nitinol hypotube or cut rigid polymer, or the like.

The flexibility of the sheath body 222 can vary over its length, with increasing flexibility towards the distal portion of the sheath body 222. The variability in flexibility may be achieved in various ways. For example, the outer jacket may change in durometer and/or material at various sections. A lower durometer outer jacket material can be used in a distal section of the sheath compared to other sections of the sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the sheath body 222. In an implementation, the distal-most section has a flexural stiffness (E*I) in the range 50 to 300 N-mm2 and the remaining portion of the sheath body 222 has a flexural stiffness in the range 500 to 1500 N-mm2, where E is the elastic modulus and I is the area moment of inertia of the device. In another implementation, there is a transition section between the distal-most flexible section and the proximal section, with one or more sections of varying flexibilities between the distal-most section and the remainder of the sheath body 222. In this implementation, the distal-most section is about 2 cm to about 5 cm, the transition section is about 2 cm to about 10 cm and the proximal section takes up the remainder of the sheath length.

The tip of the sheath body 222 may include one or more distal radiopaque markers 224 (see FIG. 1). In an implementation, the radiopaque tip marker 224 is a metal band, for example platinum iridium alloy, embedded near the distal end of the sheath body 222. Alternately, the access sheath tip material may be a separate radiopaque material, for example a barium polymer or tungsten polymer blend. The distal region of the sheath body 222 is also the area of the overlap region 120 that allows a seal between the catheter 320 and the sheath body 222, creating a continuous aspiration lumen. Thus, the outer diameter of the luminal portion 322 of the aspiration catheter 320 approaches the inner diameter of the distal region of the sheath body 222 lumen 223 such that a seal is formed. The relative location of the seal formed may vary depending on where the aspiration catheter 320 exits the lumen 223 of the sheath body 222 and the location of the openings from the sheath body 222, as described in more detail below. For example, if the sheath body 222 has an opening at the distal tip the location of the seal may be closer to the distal end of the sheath body 222 compared to if the sheath body 222 has one or more side openings in the distal end region of the sheath body 222 through which the catheter 320 exits the lumen 223.

Referring again to FIG. 1, the access sheath 220 also can include a connector 226 that connects a proximal end of the sheath body 222 to the proximal hemostasis valve 234, and also provides a connection to the aspiration line 230. This connector 226 can have a large bore inner lumen, and connects to a large-bore aspiration line 230. In an implementation, the inner lumen of the connector 226 is at least 0.080". In an implementation, the inner lumen of the aspiration line 230 is at least 0.080". The aspiration line 230 can terminate in a stopcock, female Luer connector, or other connector 232 that allows connection to an aspiration source. In an implementation, the aspiration source is an active aspiration source such as a syringe or a pump. In another implementation, the aspiration source is a reverse flow shunt line such as that described in U.S. Pat. No. 8,157,760 and US Patent Publication Number 2010/0217276, which are both incorporated by reference. The large bore aspiration line 230 can be constructed to be resistant to collapse. For example, the aspiration line 230 can be a thick-walled polymer tubing or a reinforced polymer tubing. The aspiration line valve 232 enables the line 230 to be opened or closed. In one implementation, the valve 232 also allows connection of one or more additional fluid lines, for connecting a forward drip or a flush line for contrast or saline injections. As an example, the valve 232 may be a stopcock manifold commonly used in interventional procedures to allow multiple connections. The connector 226 may also include means to secure the access sheath 220 to the patient to reduce the risk of sheath dislodgement during the case. For example, the connector 226 may include one or more suture eyelets 233.

With reference still to FIG. 1, the proximal end of the access sheath 220 can terminate in a proximal hemostasis valve 234. This valve 234 allows the introduction of devices through the sheath 220 into the vasculature, while preventing or minimizing blood loss and preventing air introduction into the access sheath 220. The hemostasis valve 234 can include a flush line 236 or a connection to a flush line 236 so that the sheath 220 can be flushed with saline or radiopaque contrast during the procedure as desired. The flush line 236 can also be used as a second point of aspiration during portions of the procedure as described more fully below. The hemostasis valve 234 can be a static seal-type passive valve, or an adjustable-opening valve such as a Tuohy-Borst valve or rotating hemostasis valve (RHV). The hemostasis valve 234 can be integral to the access sheath 220, or the access sheath 220 can terminate on the proximal end in a female Luer adaptor to which a separate hemostasis valve 234 component, such as a passive seal valve, a Tuohy-Borst valve or rotating hemostasis valve may be attached. In an implementation, the valve 234 has an adjustable opening that is open large enough to allow removal of devices that have adherent clot on the tip without causing the clot to dislodge at the valve 234 during removal. Alternately, the valve 234 is removable and is removed when the catheter tip is being removed from the sheath 220 to prevent clot dislodgement at the valve 234.

Referring again to FIG. 1, the arterial sheath system 200 can include one or more sheath dilators 250 and a sheath guidewire 270. The sheath guidewire 270 can be inserted first into the artery using standard vascular access techniques such as a micropuncture technique or Modified Seldinger technique. The sheath dilator 250 allows for smooth insertion of the access sheath 220 through a puncture site in the arterial wall. The dilator 250 can be inserted into the access sheath 220 and then the two components can be inserted together over the sheath guidewire 270 into the artery. The distal end 256 of the dilator 250 can be generally tapered to allow the dilator 250 to dilate the needle puncture site as it is being inserted through the arterial wall into the artery. The tapered distal end 256 can be generally between 6 and 12 degrees total included angle (relative to a longitudinal axis of the dilator), with a radiused leading edge.

An inner lumen of the dilator 250 can accommodate the sheath guidewire 270, and can have an inner diameter of between 0.037" to 0.041" to correspond to a sheath guidewire 270 of between 0.035" to 0.038". Alternately, the inner lumen of the dilator 250 can be between 0.020" to 0.022" to accommodate a sheath guidewire 270 of between 0.014" to 0.018". Alternately, the dilator 250 can be a two part dilator with an inner dilator and an outer dilator. The outer dilator can have an inner diameter of between 0.037" to 0.041", and the inner dilator can have an inner diameter of between 0.020" to 0.022". In use, the sheath 220 can be inserted into the artery with the outer dilator with a sheath guidewire 270 between 0.035" and 0.038". The sheath guidewire 270 may then be removed and replaced with the inner dilator and a smaller guidewire of between 0.014" and 0.018", and the access sheath 220 can then be advanced further distally to the desired site in the carotid artery.

To insert the arterial sheath 220 initially over the sheath guidewire 270 into the artery, the dilator taper 256 can have a certain stiffness and taper angle to provide the adequate dilating force on the arterial puncture site. However, to safely reach the petrous portion of the ICA, it may be desirable to have a sheath dilator 250 with a softer and/or longer taper at a distal end than that used for initial arterial access. In an implementation, the access sheath system 200 can include two or more tapered dilators. The first tapered dilator can be used with the arterial access device to gain entry into the artery, and is thus sized and constructed in a manner similar to standard introducer sheath dilators. Example materials that may be used for the tapered dilator include, for example, high density polyethylene, 72D PEBAX, 90D PEBAX, or equivalent stiffness and lubricity material. A second tapered dilator may be supplied with a softer distal section or a distal section that has a lower bending stiffness relative to the distal section of the first tapered dilator, and/or a longer taper length. That is, the second dilator has a distal region that is softer, more flexible, or articulates or bends more easily than a corresponding distal region of the first dilator. The distal region of the second dilator thus bends more easily than the corresponding distal region of the first dilator. In an implementation, the distal section of the first dilator has a bending stiffness in the range of 50 to 100 N-mm2 and the distal section of the second dilator has a bending stiffness in the range of 5 to 15 N-mm2. The second dilator (which has a distal section with a lower bending stiffness) may be exchanged with the initial, first dilator such that the access sheath 220 may be advanced into the internal carotid artery and around curvature in the artery without undue force or trauma on the vessel due to the softer distal section of the second dilator.

The distal section of the soft, second dilator may be, for example, 35 or 40D PEBAX, with a proximal portion made of, for example 72D PEBAX. An intermediate mid portion or portions may be included on the second dilator to provide a smooth transition between the soft distal section and the stiffer proximal section. In an implementation, both dilators have an inner diameter of between 0.037" to 0.041". In an alternate implementation, the first dilator has an inner diameter of between 0.037" to 0.041" and the second dilator has an inner diameter of between 0.020" to 0.022". In yet another implementation, the second dilator is a two part dilator with an inner dilator and an outer dilator, as described above. In an implementation, one or both dilators may have radiopaque tip markers 224 so that the dilator tip position is visible on fluoroscopy. In one variation, the radiopaque marker 224 is a section of tungsten loaded PEBAX or polyurethane that is heat welded to the distal tip of the dilator. Other radiopaque materials may similarly be used to create a radiopaque marker 224 at the distal tip.

In an implementation, the access sheath 220 includes a proximal extension 240 that extends between the connector 226 and the proximal hemostasis valve 234. In the transcarotid configuration of the system, it may be desirable to move the proximal hemostasis valve 234 away from the distal tip of the access sheath 220, effectively elongating or lengthening the proximal portion of the access sheath that is outside the body while maintaining the length of the insertable sheath body portion 222. This allows the user to insert devices into the proximal hemostasis valve 234 of the access sheath 220 from a point further away from the target site and therefore away from the x-ray source and/or image intensifier used to image the target site fluoroscopically, thereby minimizing radiation exposure of the user's hands and also his or her entire body. In this implementation, the proximal extension 240 can be in the range between 10 and 25 cm, or between 15 and 20 cm. In either the transcarotid or transfemoral configuration, it may also be desirable to provide a section of the access sheath 220 that is fluidly connected to the access sheath aspiration line, but which may extend proximally from the aspiration line connection. This will allow users to pull devices out of the flow of blood from the sheath tip to the aspiration line, without completely removing the device from the access sheath 220.

Figure 4:
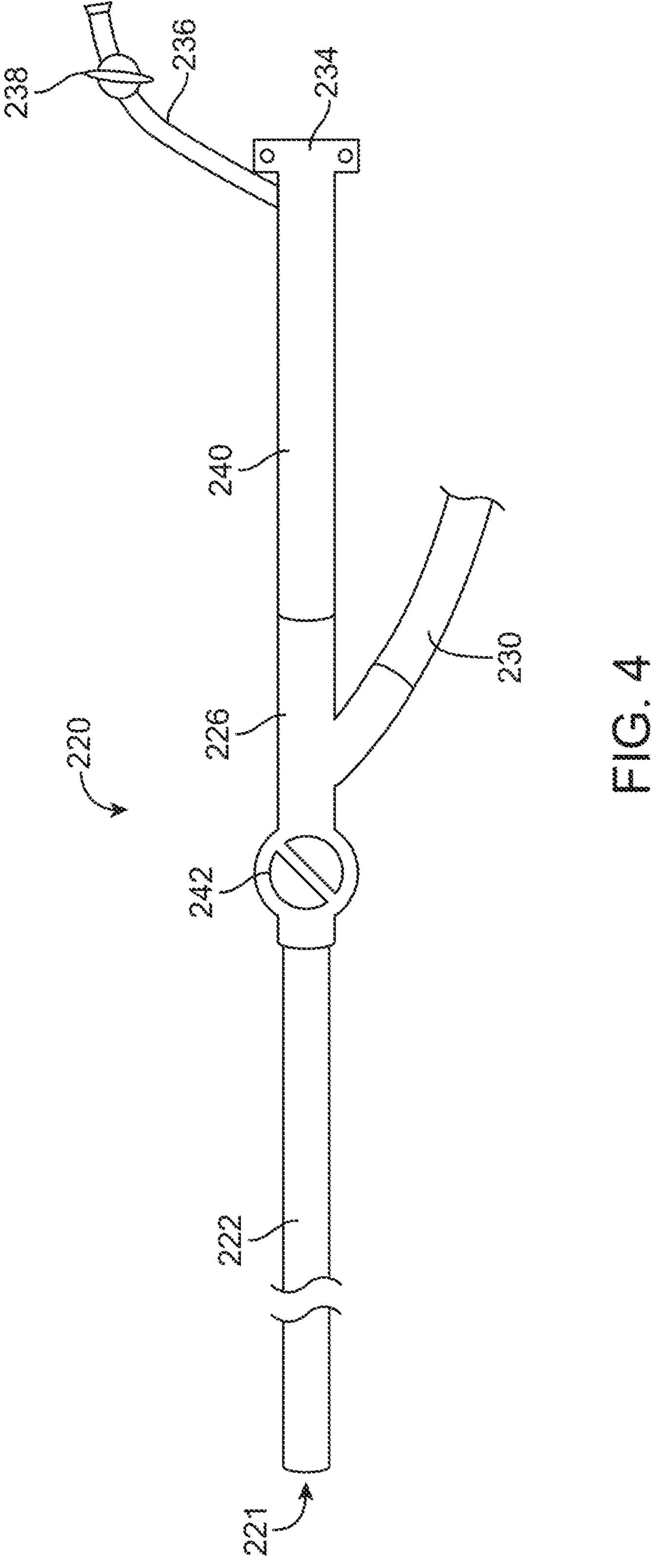
FIG. 4 shows an implementation of an access sheath.

In an alternate implementation, it may also be desirable to intermittently isolate this proximal portion 240 from the sheath body 222. In an implementation, as shown in FIG. 4, the connector 226 includes a valve 242 that can close off the fluid connection between the sheath body 222 and the proximal portion 240 of the access sheath 220, including the aspiration line 230, proximal extension 240 and proximal hemostasis valve 234. This can allow the distal portion of a catheter, retrievable stent device, or other thrombectomy device to be pulled into this proximal extension portion 240, the valve 242 closed to fluidly isolate the sheath body 222 from the proximal portion of the sheath, and then the proximal hemostasis valve 234 to be widely opened or removed, or the entire proximal extension portion 240 of the sheath 220 removed, without arterial bleeding from the sheath 220. The proximal extension 240 can be at least as long as the distal luminal portion 222 of the spined catheter 320 so that the distal luminal portion 322 may be pulled entirely into the proximal extension 240 and the valve 242 closed off before the proximal hemostasis valve 234 is widely opened to remove the catheter 320 entirely from the sheath 220.

Alternately, after the thrombectomy device or other interventional device is pulled into this proximal extension portion 240 and the sheath body 222 closed off via the valve 242, a portion of the thrombectomy device, such as the distal luminal portion 322 of the aspiration catheter 320, may remain in the proximal extension 240 and be flushed or otherwise cleared by creating flow from the flush line to the aspiration lines to dislodge clot without fully removing the device 320 from the access sheath 220. This ability to flush and clear the thrombectomy device without fully removing the thrombectomy device may reduce bleeding, time, and risk of air emboli during the steps between thrombectomy attempts. Also, withdrawing the thrombectomy device into the proximal extension 240 without fully removing it from the sheath body 222 while flushing and clearing also minimizes operator and staff exposure to blood and debris associated with device cleansing. In any of these implementations, the proximal extension tubing is clear so that the flush solution and presence/absence of embolic debris or air is clearly visible through the tubing.

Figure 5:
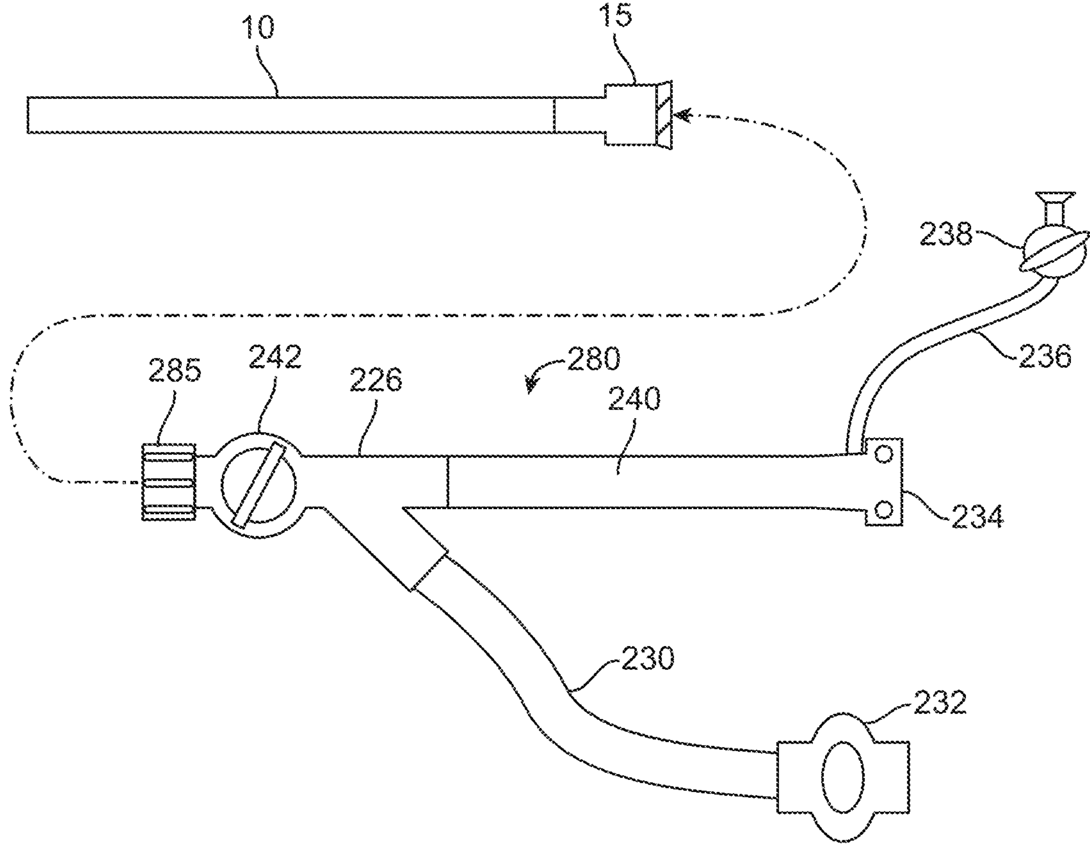
FIG. 5 shows an implementation of a proximal portion of the access sheath of FIG. 4 provided as a separate, removable component.
Figure 6:
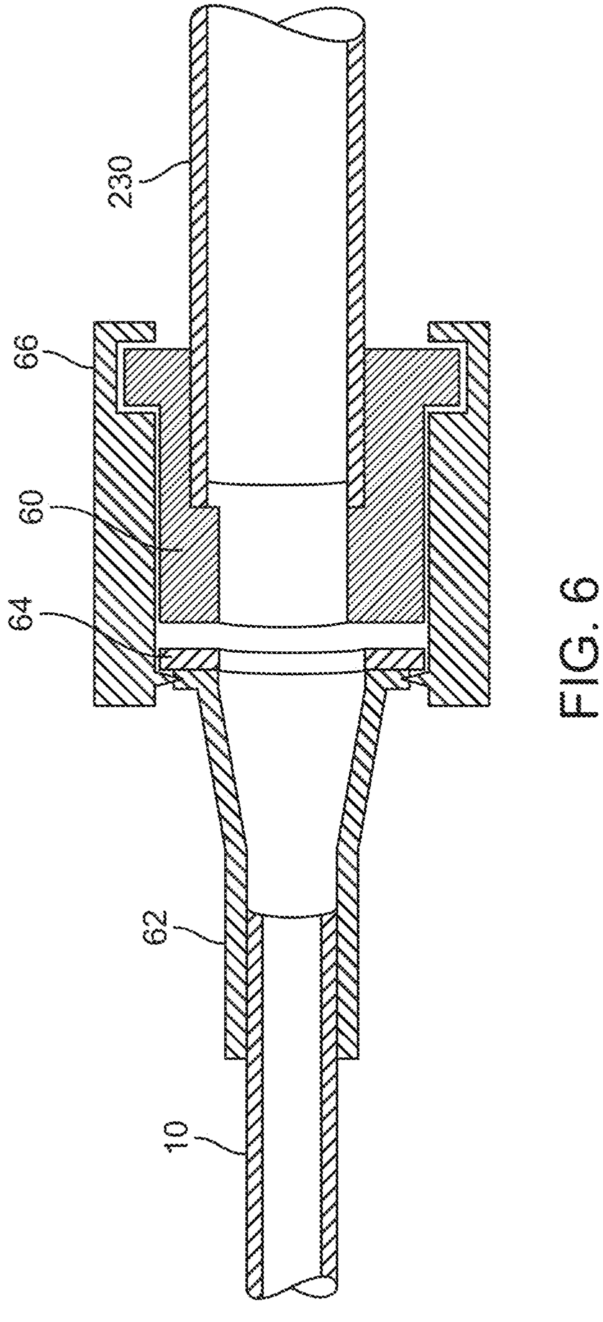
FIG. 6 shows an implementation of a connector to minimize flow resistance through the access sheath of FIG. 4 into the proximal portion.

The proximal extension portion 240 of the access sheath 220 can be provided as a separate, removable component that can be attached to any sheath with a standard connection on the proximal end. As shown in FIG. 5, a proximal component 280 includes a connector 285 that can attach to a proximal hub 15 of a standard sheath 10. The coupled components can create an assembly with the configuration and features of access sheath 220. In this implementation, the user can select from any of several already available sheaths of appropriate length, shape, and mechanical characteristics for the procedure, and perform the steps of the procedure described in this disclosure. The removable proximal component 280 can include the Y-arm connector 226, aspiration line 230, proximal extension 240, proximal hemostasis valve 234 and flush line 236, along with the valve connectors 232 and 238 terminating the aspiration line 230 and flush line 236 respectively. A connector 285 can couple to the proximal connector 226 on the sheath 220. In an implementation as shown in FIG. 6, the connector 285 is configured to minimize the flow resistance through the sheath 10 and into the proximal portion 280. For example, instead of a standard male-female Luer connection, the connector 285 can include an adaptor 60 with an inner lumen and surface that matches a standard female Luer connector 62 typically found on sheaths, a seal element 64 that seals between the adaptor 60 and the sheath female Luer 62, and a rotating nut 66 that engages the thread elements of the female Luer 62 and couples the adaptor 60 and Luer 62 together such that the seal 64 is compressed and can seal against fluid and air vacuum and pressure. Again with respect to FIG. 5, the proximal component 280 may also include a valve 242 on the Y-arm connector 226, so that when the proximal component 280 is attached to a sheath 10, the proximal section may be selectively open or closed to fluid connection with the sheath 10. A similar type of connection can be made for connector 232 connecting the sheath aspiration line 230 to an aspiration source.

In a preferred implementation, the proximal connection has a proximal extension length of about 22 cm, a Y-arm connector of about 7 cm, and a proximal hemostasis valve of length about 5 cm for a total length of about 34 cm.

Figure 7:
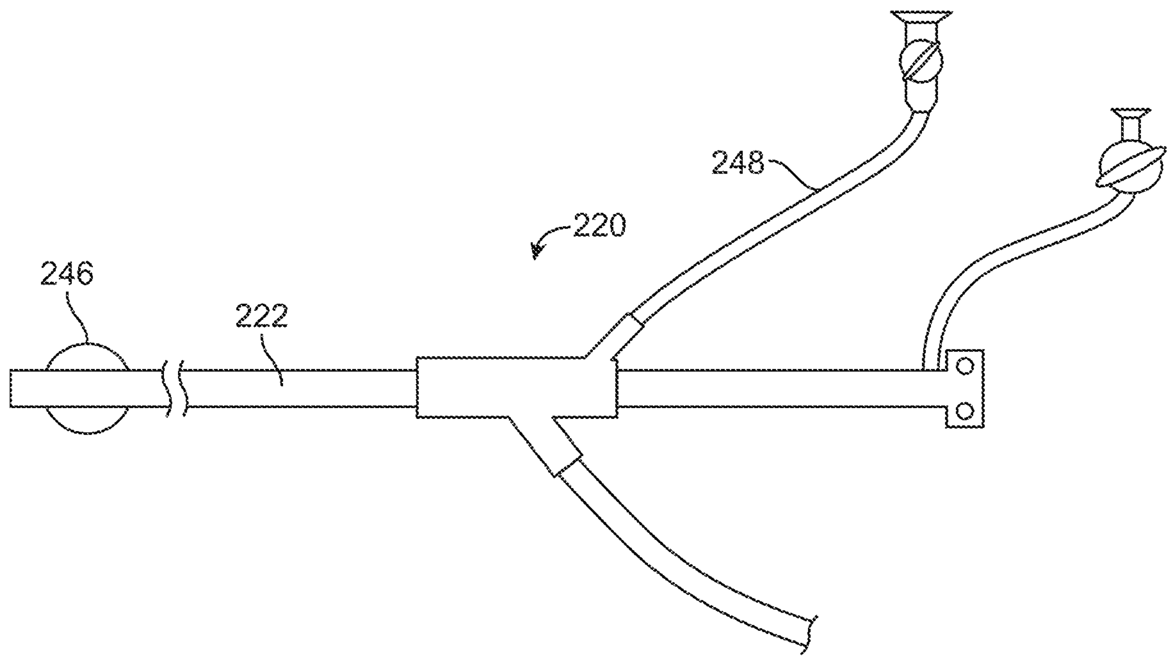
FIG. 7 shows an implementation of an access sheath having an occlusion balloon.

It may be desirable to transiently occlude the carotid artery during the intervention to arrest antegrade flow of emboli during portions of the procedure. In an implementation, as shown in FIG. 7, the access sheath 220 includes an occlusion balloon 246 on the distal tip of the sheath body 222. An additional lumen in sheath body 222 can be connected to an inflation line 248 and fluidly connects the balloon 246 to the inflation line 248. An inflation device is attached to inflation line 248 to inflate the occlusion balloon 246. In this implementation, the balloon 246 is inflated when carotid artery occlusion is desired.

In some instances it is desirable to keep the sheath tip as small as possible during sheath insertion to minimize the diameter of the arterial puncture, but to expand the opening of the sheath 220 after it has been inserted into the vessel. At least one purpose of this feature is to minimize the effect or creation of distal emboli during pull back of an aspiration catheter 320 or other thrombectomy device into the sheath 220. During a thrombectomy procedure, the thrombus may be "pulled back" into a distal opening 221 of the sheath 220 on a device that has captured the thrombus. If the distal tip of the sheath 220 is enlarged relative to its initial size, or flared into a funnel shape, the chance of pieces of the thrombus breaking off and causing emboli is minimized because the larger size or funnel shape of the sheath tip is more likely to accommodate the emboli being drawn into it without being split into multiple pieces. This creates a better clinical outcome for the patient. In an implementation of the access sheath, the distal portion of the sheath body 222 is a material and/or construction such that the tip can be expanded after the sheath 220 is inserted into the artery and positioned in its desired location. In an implementation, the distal region of the sheath has an ID of about 0.087" can be enlarged to a diameter of about 0.100" to 0.120" although the size may vary and/or be flared.

Examples of expanding distal tip constructions include covered braided tips that can be shortened to expand. Another example of an expanding distal tip construction is an umbrella or similar construction that can open up with mechanical actuation or elastic spring force when unconstrained. Other mechanisms of expandable diameter tubes are well known in the art. One particular implementation is a sheath made of material that is deformable when expanded using a high pressure balloon. Co-pending U. S. Patent Publication number 2015/0173782, filed on Dec. 19, 2014, describes exemplary devices and is incorporated herein by reference in its entirety. Construction of such features are described in co-pending Publication number 2015/0173782.

The distal end region of the sheath body 222 also may vary in the location, size and number of openings. The sheath body 222 may incorporate one or more openings near the distal end region of the sheath 220 that allow for fluid flow between the lumen 223 of the sheath body 222 and the vasculature within which the sheath 220 is positioned. The one or more openings can be sized to allow at least the luminal portion 322 of the aspiration catheter 320 to extend therethrough. The one or more openings may be sized larger than the outer diameter of the luminal portion 322 such that the one or more openings form an elongate mouth, slot or notch in a distal end region of the sheath body 222. The one or more openings may be formed within a region of the side wall of the sheath body 222 just proximal to the distal end, such that the opening is located at least 0.25 mm, 0.5 mm, 1.0 mm, 1.5 mm, 2.0 mm, 2.5 mm, 3.0 mm, 3.5 mm, or 4.0 mm or greater from the distal end of the sheath body 222. The one or more openings may be a plurality of openings forming a porous region near the distal end region of the sheath body 222 wherein at least one of the pluralities of openings is sized large enough to allow one or more components of the system to exit the lumen 223 of the sheath body 222. In some implementations, the one or more openings includes a distal opening 221 from the lumen 223 of the sheath body 222 (see FIGS. 4 and 12C). In some implementations, the one or more openings includes an elongate, distal mouth forming a side opening 1219 on a first side of the sheath body 222 located near a distal end region (see FIG. 12C). The side opening 1219 may be located at least 0.25 mm or more from the distal end of the sheath body 222. The side opening 1219 may having a diameter that is at least as large as the outer diameter of the distal luminal portion 322 of the spined catheter 320. Preferably, the side opening 1219 has a diameter that is at least 1.5×, 2×, 2.5×, or 3× as large as the outer diameter of the distal luminal portion 322. In another implementation, the sheath body 222 includes a pair of side openings 1219 on opposing and/or adjacent sides of the sheath body 222 near the distal end region. In another implementation, the sheath body 222 includes a distal opening 221 from the lumen 223 and one or more elongate side openings 1219 from the lumen 223. It should be appreciated that the sheath body 222 can be rotated around the longitudinal axis A such that the one or more side openings 1219 are positioned to allow for distal extension of the catheter 320 from the side openings 1219 in a desired direction relative to the longitudinal axis A of the sheath 220. Inclusion of a wide-mouthed side opening 1219 can allow for a range of exit angles for the catheter 320 from a position substantially (i.e. very nearly) parallel to the sheath body 222 to a position that is at an angle to the sheath body 222, for example substantially perpendicular or at a right angle to the sheath body 222, as well as greater than 90° angle. This arrangement can be critically important in situations where there is severe angulation within the vessel being traversed or where a bifurcation is present. Often, tortuous segments in vessels and bifurcations have severe angulations to 90° or greater angle up to 180°. Classic severe angulation points in the vasculature can include the aorto-iliac junction, the left subclavian artery takeoff from the aorta, the brachiocephalic (innominate) artery takeoff from the ascending aorta as well as many other peripheral locations.

Referring again to FIG. 1, as mentioned above the catheter system 300 can include a spined aspiration catheter 320 having a flexible, distal luminal portion 322 and a rigid, proximal spine 330. The outer diameter of the distal luminal portion 322 as well as the flexibility and lubricity of the luminal portion 322 paired with the rigid spine 330 allow for the spined aspiration catheter 320 to navigate to the site of occlusions in the cerebral vasculature compared to other systems configured to navigate the cardiac vasculature. The systems described herein can reach occlusions in a region of the anatomy that has a long, tortuous access route. The route may contain stenosis plaque material in the aortic arch and carotid and brachiocephalic vessel origins, presenting a risk of embolic complications. Further, cerebral vessels are usually more delicate and prone to perforation than coronary or other peripheral vasculature. The catheter systems described herein can provide for neurovascular interventional procedures more easily due to its ability to overcome these access challenges. The catheter systems described herein are designed for navigating tortuosity rather than pushing through it. U.S. Patent Publication Number 2015/0174368, filed on Dec. 12, 2014, and U.S. Patent Publication Number 2015/0173782, filed on Dec. 19, 2014, which are incorporated herein by reference, describe features of catheter devices that can navigate the tortuous anatomy of the cerebral arteries.

The length of the distal luminal portion 322 can vary. In some implementations, the length of the distal luminal portion 322 extends from a region near the distal tip of the access sheath body 222 to the site of the occlusion in the carotid artery, forming a proximal overlap region 120 with the distal end of the access sheath 220 (see FIG. 2B). Taking into account the variation in occlusion sites and sites where the access sheath distal tip may be positioned, the length of the distal luminal portion 322 may range from about 10 cm to about 25 cm. The length of the distal luminal portion 322 is less than the length of the sheath body 222 of the access sheath 220, such that as the spined aspiration catheter 320 is retracted into the sheath body 222 there remains a seal between the overlap region 328 of the spined aspiration catheter 320, and the inner diameter of the sheath body 222.

The catheter systems described herein can incorporate multiple spined catheters that are nested inside one another to allow for an extended reach into the tortuous anatomy. For example, a first spined catheter 320 having an outer diameter sized to be received within the lumen of the sheath body 222 may have a second spined catheter 320 extending through the inner lumen of the first spined catheter 320. The second spined catheter 320 can be extended using its proximal spine beyond a distal end of the first spined catheter 320 such that the smaller diameter second spined catheter 320 can reach a more distal region of the vasculature, particularly one having a narrower dimension. In this implementation, the first spined catheter 320 can act as a support catheter for the second spined catheter 320. The second spined catheter 320 can have an inner lumen that fluidly communicates with the inner lumen of the first spined catheter 320 that fluidly communicates with an inner lumen of the sheath body 222 forming a contiguous aspiration lumen.

In an implementation, the distal luminal portion 322 of the catheter 320 is constructed to be flexible and lubricious, so as to be able to be safely navigated to the target site, and kink resistant and collapse resistant when subjected to high aspiration forces, so as to be able to effectively aspirate the clot, with sections of increasing flexibility towards the distal end. In an implementation, the distal luminal portion 322 includes three or more layers, including an inner lubricious liner, a reinforcement layer, and an outer jacket layer. The outer jacket layer may be composed of discreet sections of polymer with different durometers, composition, and/or thickness to vary the flexibility along the length of the distal luminal portion 322. In an implementation the lubricious inner liner is a PTFE liner, with one or more thicknesses along variable sections of flexibility. In an implementation, the reinforcement layer is a generally tubular structure formed of, for example, a wound ribbon or wire coil or braid. The material for the reinforcement structure may be stainless steel, for example 304 stainless steel, nitinol, cobalt chromium alloy, or other metal alloy that provides the desired combination of strengths, flexibility, and resistance to crush. In an implementation, the reinforcement structure includes multiple materials and/or designs, again to vary the flexibility along the length of the distal luminal portion 322. In an implementation, the outer surface of the catheter 320 is coated with a lubricious coating such as a hydrophilic coating. In some implementations the coating may be on an inner surface and/or an outer surface to reduce friction during tracking. The coating may include a variety of materials as is known in the art. The spine portion 330 may also be coated to improve tracking through the access sheath 220. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The outer diameter of the distal luminal portion 322 can be sized for navigation into cerebral arteries. It is desirable to have a catheter having an inner diameter that is as large as possible that can be navigated safely to the site of the occlusion, in order to optimize the aspiration force. A suitable size for the inner diameter may range between 0.040" and 0.075" or may range between 0.040" and 0.088", depending on the patient anatomy and the clot size and composition. The outer diameter should be as small as possible while still maintaining the mechanical integrity of the catheter 320. However, at the overlap region 120, the outer diameter (OD) of the catheter 320 approaches the inner diameter (ID) of the access sheath 220, so as to create a sealed area at the overlap region 120 whilst still enabling the catheter 320 to be inserted easily through the sheath 220 and positioned at the desired site. In an implementation, the catheter 320 and access sheath 220 are sized to match at the overlap region 120 with no change in catheter 320 outer diameter (see FIG. 2B). In an implementation, the difference between the catheter OD and the access sheath ID at the overlap region is 0.002" or less. In another implementation, the difference is 0.003" or less. In an implementation, the catheter 320 is tapered towards the distal tip of the distal luminal portion 322 such that the distal-most end of the catheter has a smaller outer diameter compared to a more proximal region of the catheter near where it seals with the access sheath. In another implementation, the catheter OD steps up at an overlap portion 328 to more closely match the sheath inner diameter (see FIG. 1). This implementation is especially useful in a system with more than one catheter suitable for use with a single access sheath size. It should be appreciated where the catheter OD of the spined catheter 320 matches the sheath inner diameter or the difference is 0.002" or less, a seal to fluid being injected or aspirated can be achieved by the overlap portion 328 such that no increase in catheter OD is necessary. A seal to fluid being injected or aspirated between the catheter and the sheath can be achieved by the overlap between their substantially similar dimensions without incorporating any separate sealing structure or seal feature.

Figure 8A:
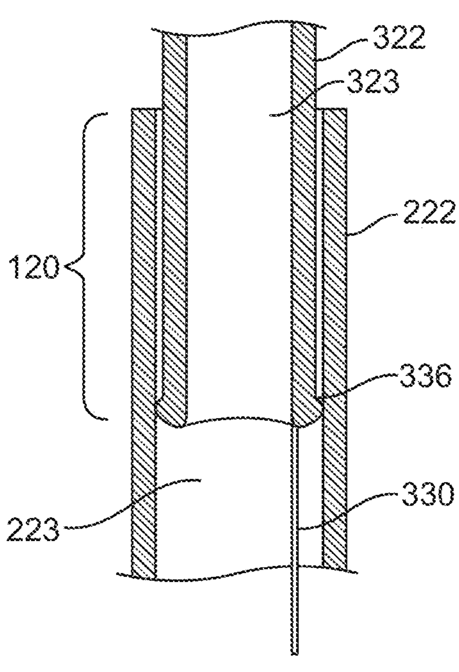
FIGS. 8A-8B show implementations of sealing elements between the access sheath body and luminal portion of a catheter extending therethrough.
Figure 8B:
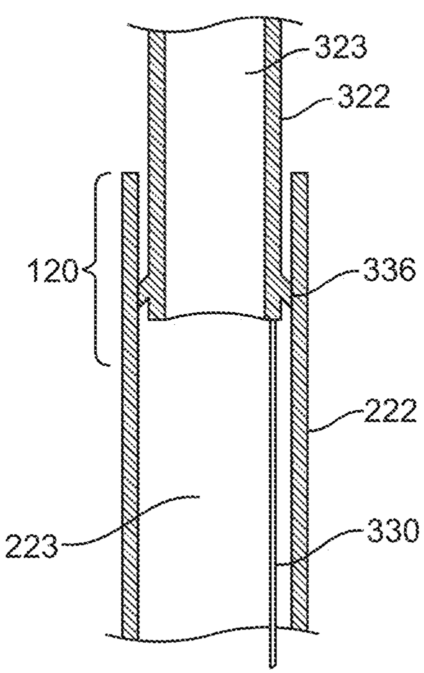

In another implementation as shown in FIGS. 8A and 8B, there is a sealing element 336 positioned on the external surface of the proximal end of the distal luminal portion 322. The sealing element 336 can be one or more external ridge features, and can be compressed when the catheter 320 is inserted into the lumen of the access sheath 220. The ridge geometry can be such that the sealing element 336 behaves as an O-ring, quad ring, or other piston seal design. FIG. 8B shows a similar configuration, with the sealing element 336 having a wiper seal configuration such as an inclined surface that is biased against an inner surface of access sheath body 222. Alternately, the seal element 336 may be an inflatable or expandable member such as a balloon or covered braid structure that can be inflated or expanded and provide sealing between the two devices at any time, including after the catheter 320 is positioned at the desired site. An advantage to this implementation is that there is no sealing force being exerted on the catheter 320 during catheter positioning, but rather is applied or actuated to seal after the catheter 320 is positioned.

It should be appreciated that the shape of the proximal end region of the distal luminal portion 322 may have an angled cut compared to the straight cut shown in the FIGS. 8A-8B. It should also be appreciated that the spine 330 may be coupled to a proximal end region of the catheter 320 and/or may extend along at least a portion of the distal luminal portion 322 such that the spine 330 couples to the distal luminal portion 322 a distance away from the proximal end. The spine 330 can be coupled to the portion 322 by a variety of mechanisms including bonding, welding, gluing, sandwiching, stringing, tethering, or tying one or more components making up the spine 330 and/or portion 322. In some implementations, the spine 330 and luminal portion 322 are coupled together by sandwiching the spine 330 between layers of the distal luminal portion 322. For example, the spine 330 can be a hypotube or rod having a distal end that is skived, ground or cut such that the distal end can be laminated or otherwise attached to the layers of the catheter portion 322 near a proximal end region. The region of overlap between the distal end of the spine 330 and the portion 322 can be at least about 1 cm. This type of coupling allows for a smooth and even transition from the spine 330 to the luminal portion 322.

In an implementation, the overlap region is configured to enable sealing against a vacuum of up to 25 inHg, or up to 28 inHg. In an implementation, the overlap region 120 is configured to enable sealing against a pressure of up to 300 mmHg or up to 600 mmHg or up to 700 mmHg with minimal to no leakage. In addition, there may be features that prevent excessive advancement of the spined aspiration catheter 320 beyond the distal end of the access sheath 220. In any implementation that involves a stepped up diameter or protruding feature at the overlap region 328 of the spined aspiration catheter 320, the access sheath body 222 may include an undercut at the tip that prevents the proximal overlap portion of the spined aspiration catheter 320 to exit the sheath body 222.

The distal luminal portion 322 of the catheter 320 can have a radiopaque marker 324 at the distal tip to aid in navigation and proper positioning of the tip under fluoroscopy (see FIG. 1). Additionally, the proximal overlap region 328 of the catheter 320 may have one or more proximal radiopaque markers 1324 (see FIG. 12C) so that the overlap region 120 can be visualized as the relationship between the access sheath distal marker 224 and the catheter proximal marker 1324. In an implementation, the two markers (marker 324 at distal tip and a more proximal marker 1324) are distinct so as to minimize confusion of the fluoroscopic image, for example the catheter proximal marker 1324 may be a single band and the sheath tip marker 224 may be a double band.

The spine 330 of the spined aspiration catheter 320 is coupled to a proximal end region of the distal luminal portion 322. The spine 330 is configured to allow distal advancement and proximal retraction of the catheter 320 through the lumen 223 of the access sheath 220. In an implementation, the length of the spine 330 is longer than the entire length of the access sheath 220 (from distal tip to proximal valve), such as by about 5 cm to 15 cm. As shown in FIG. 1, the spine 330 can include a mark 332 to indicate the overlap between the distal luminal portion 322 of the catheter 320 and the sheath body 222. The mark 332 can be positioned so that when the mark 332 is aligned with the sheath proximal valve 234 during insertion of the catheter 320 through the sheath 220, the spined aspiration catheter 320 is positioned at the distal-most position with the minimal overlap length needed to create the seal between the spined aspiration catheter 320 and the access sheath 220. The spine 330 can include a gripping feature such as a tab 334 on the proximal end to make the spine easy to grasp and advance or retract. The tab 334 can coupled with one or more other components of the system 300, such as a dilator configured to extend through the lumen 323 of the distal luminal portion 322 as will be described in more detail below. The proximal tab 334 can be designed to be easily identifiable amongst the other devices existing in the sheath proximal valve 234, such as guidewires 270 or retrievable stent device wires 500. In an implementation, the spine 330 is colored a bright color, or marked with a bright color, to make it easily distinguishable from guidewire, retrievable stent tethers, or the like.

The spine 330 can be configured with sufficient stiffness to allow advancement and retraction of the distal luminal portion 322 of the spined aspiration catheter 320, yet also be flexible enough to navigate through the cerebral anatomy as needed. Further, the outer diameter of the spine 330 is sized to avoid taking up too much luminal area in the lumen 223 of the access sheath 220 and sheath body 222. In an implementation, the spine 330 is a round wire, with dimensions from 0.014" to 0.018". In another implementation, the spine 330 is a ribbon with dimensions ranging from 0.010" to 0.015" thick, and 0.015" thick to 0.025" thick. The ribbon can have a variety of cross-sectional shapes such as a flat ribbon or curved ribbon forming a c-shape or other shape along an arc. In another implementation, the spine 330 is a hypotube. In an implementation, the spine 330 material is a metal such as a stainless steel or nitinol as well as a plastic such as any of a variety of polymers.

One or more components of the systems described herein may be made from a metal, metal alloy, polymer, a metal-polymer composite, ceramics, combinations thereof, and the like, or other suitable materials. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UM: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

The junction between the distal luminal portion 322 of the catheter 320 and the proximal spine 330 can be configured to allow a smooth transition of flexibility between the two portions so as not to create a kink or weak point, and also allow smooth passage of devices such as guidewires and microcatheters through the continuous inner lumen created by the lumen 223 of the access sheath 220 and the lumen 323 of the luminal portion 322 of the catheter 320. In an implementation, the distal luminal portion 322 has a transition section 326 (see FIG. 1) near where the portion 322 couples to the spine 330 that has an angled cut such that there is no abrupt step transition from the sheath 220 inner lumen 223 to the catheter 320 inner lumen 323. The angled cut can be generally planer. In an alternate implementation, the angled cut is curved or stepped to provide a more gradual transition zone. The distal luminal portion 322 and the spine 330 may be joined by a weld bond, a mechanical bond, an adhesive bond, or some combination thereof. The distal end of the spine 330 may have features that facilitate a mechanical joint during a weld, such as a textured surface, protruding features, or cut-out features. During a heat weld process, the features would facilitate a mechanical bond between the polymer distal luminal portion 322 and the spine 330. In another implementation, such as the catheter system 1300 shown in FIGS. 12A-12B having a spined catheter 1320 and a dilator 1340 extending therethrough, a smooth transition of flexibility between the two portions is formed so as not to kink or create a weak point during advancement of the system 1300. Loss of this smooth flexibility transition can occur upon removal of the dilator 1340 from the spined catheter 1320. The spine 1330 can be intended primarily to withdraw the spined catheter 1320 where risk of kink or weak spot formation is markedly lower.

Because the spined aspiration catheter 320 does not have a lumen that runs its entire length 320 due to the presence of the spine 330 on its proximal end region, traditional flushing and preparation steps, either before use or during the procedure should the lumen of the catheter become clogged, are ineffective. In a traditional single lumen catheter, a syringe is attached to the proximal adaptor of the catheter and the inner lumen may be forcefully flushed with solution. The spined catheter 320 can be supplied with an accessory catheter flushing and clearing device 350 (see FIG. 1). This device 350 may be a tube with a rounded or tapered tip on a distal end and a female Luer connection on the proximal end. The Luer connector allows a syringe to be connected to the device 350. The blunt or tapered tip enables the device 350 to be inserted into either the distal or proximal end of the luminal portion 322 of the catheter 320, without risk of damaging the catheter 320, and the syringe actuated to flush the device. The OD of the clearing device 350 is closely matched with the ID of the luminal portion 322 of the spined catheter 320, such that the spined aspiration catheter 320 may be flushed with enough force to clear out the catheter of debris and aspirated occlusive material. The device 350 may also be used to mechanically clear out any entrapped thrombus in a plunger-type action, the working length of the device 350 can be at least as long as the distal luminal portion 322 of the catheter 320, so that it may be inserted through the entire lumen 323 of the distal luminal portion 322. Flushing may occur in conjunction with plunging the device 350, to more effectively clear the catheter 320 of entrapped thrombus or other embolic material.

In an alternate implementation, the aspiration catheter 320 is a single lumen catheter, for example, the type of catheter described in co-pending application U.S. Patent Publication Number 2015/0174368, filed Dec. 12, 2014. In such an implementation, the catheter may be supplied with or coupled with a tapered co-axial dilator 340 that is generally tubular and has a tapered distal portion that provides a smooth transition between the catheter and a guidewire positioned within the catheter.

The spined aspiration catheter 320 can be navigated through the vasculature over an appropriately-sized microcatheter and guidewire. Alternately, the spined catheter 320 can be supplied with a co-axial dilator 340 (see FIG. 1). The dilator 340 is sized and shaped to be inserted through the internal lumen 323 of the distal luminal portion 322 of the catheter 320 in a coaxial fashion, such that a proximal end region of the dilator 340 aligns side-by-side with the spine 330 of the catheter 320 when in use. The dilator 340 can have a tapered distal tip 346. The length of the dilator 340 can be at least as long as the spined aspiration catheter 320 allowing for the distal tapered tip 346 as a minimum to protrude from the distal end of the luminal portion 322 of the spined catheter 320. The dilator 340 can have an outer diameter that forms a smooth transition to the distal tip of the catheter, and the distal tapered tip 346 that provides a smooth transition down to the guidewire that extends out the inner lumen of the dilator 340. The dilator 340 can be generally tubular along at least a portion of its length. In an implementation, the tapered dilator 340 is designed to accommodate a guidewire that may be in the range of 0.014" and 0.018" diameter for example. In this implementation, the inner luminal diameter may be between 0.020" and 0.024". The tapered distal tip 346 may be in range from 1.5 cm to 3 cm.

It should be appreciated that the dilators described herein for use with the spined catheters can vary in their configuration. For example, as described above the dilator 340 can be a co-axial dilator 340 that is generally tubular and has a tapered distal portion that provides a smooth transition between the catheter 320 and a guidewire positioned within the catheter 320. The tubular body of the dilator 340 can extend along the entire length of the catheter 320. Alternatively, the dilator 340 can incorporate a proximal spine that aligns side-by-side with the spine of the catheter 320. The proximal spine can be positioned co-axial or eccentric to a distal end region of the dilator 340. The co-axial proximal spine of the dilator 340 can have a lumen extending through it. Alternatively, the dilator 340 can be a solid rod having no lumen. The solid rod dilator can be formed of a malleable material that skives down to have a narrow outer diameter (e.g. 0.010"-0.014") such that the dilator can be shaped to whatever angle or shape is desired by the user, similar to how a guidewire may be used. In this configuration, the catheter system does not include a guidewire or microcatheter. Such a dilator has a benefit over a microcatheter in that it can have an outer diameter that is 0.003"-0.010" smaller than the inner diameter of the spined catheter 320.

The dilator 340 may have a proximal female Luer adaptor 348 at a proximal end to allow the dilator 340 to be flushed with a syringe. The dilator 340 may also incorporate a clip feature at a proximal end allowing the dilator 340 to be the material of the dilator 340 can be flexible enough and the taper distal tip 346 can be long enough to create a smooth transition between the flexibility of the guidewire and the flexibility of the catheter. This configuration can facilitate advancement of the catheter 320 through the curved anatomy and into the target cerebral vasculature. In an implementation, the distal end of the dilator 340 has a radiopaque marker 344 and/or a marker 343 at the proximal end of the taper distal tip 346. The marker material may be a platinum/iridium band, a tungsten, platinum, or tantalum-impregnated polymer, or other radiopaque marker.

The dilator 340 can be constructed to have variable stiffness between the distal and proximal ends of the dilator 340. For example, the distal most section that extends beyond the distal end of the luminal portion 322 of the catheter 320 can be made from a more flexible material, with increasingly stiffer materials towards the more proximal sections. In some implementations, the dilator 340 can be a spined dilator having a proximal spine as will be described in more detail below. The proximal end of the dilator 340 can include a tab 1364 that allows the dilator 340 to lock with the tab 334 on the proximal end of the spine 330 of the catheter 320, such that the two components (the spined catheter 320 and the dilator 340) may be advanced as a single unit over the guidewire (see FIG. 12A). In some implementations, the tab 334 of the catheter 320 can form a ring having a central opening extending therethrough. The tab 1364 of the dilator 340 can have an annular detent with a central post. The central post of the tab 1364 can be sized to insert through the central opening of the tab 334 such that the ring of the tab 334 is received within the annular detent of tab 1364 forming a singular grasping element for a user to advance and/or withdraw the catheter system through the access sheath. The tab 1364 may be affixed to the dilator 340, or may be slideable on the dilator 340 to accommodate different relative positions between the dilator 340 and the spined catheter 320.

Figure 12A:
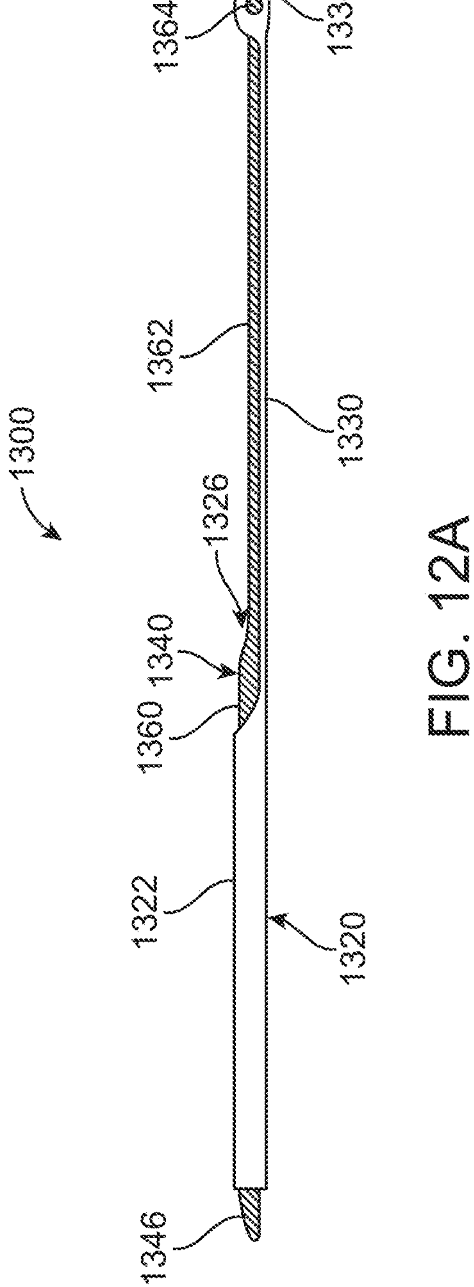
FIG. 12A shows an implementation of a spined catheter system for use with the systems described herein.

FIGS. 12A-16 provide additional views of a spined aspiration catheter and dilator system 1300 as described elsewhere herein. FIGS. 12A-12B show the spined aspiration catheter 1320 having a dilator 1340 extending through an aspiration lumen 1323 of the distal luminal portion 1322. As described elsewhere herein, the catheter 1320 can have a proximal spine 1330 having a tab 1334 and a distal luminal portion 1322 having an aspiration lumen 1323. The spine 1330 can extend between the distal luminal portion 1322 and the tab 1334. The dilator 1340 can be received within the aspiration lumen 1323 of the spined catheter 1320. The dilator 1340 can include a distal dilator portion 1360 and a proximal spine 1362. The dilator portion 1360 can extend between a distal tip 1346 of the dilator 1340 to the start of the proximal spine 1362. When engaged with the catheter 1320, the dilator portion 1360 of the dilator 1340 may extend through an entire length of the distal luminal portion 1322 of the catheter 1320 such that the dilator tip 1346 extends a fixed distance beyond a distal end of the distal luminal portion 1322 of the catheter 1320 providing a smooth transition for improved tracking. The dilator tip 1346 can be tapered as described elsewhere herein and can be soft, atraumatic and flexible to the vessel wall to facilitate endovascular navigation to an embolus in a tortuous anatomy compared to dilators typically used for percutaneous arterial access, which are meant to bluntly dissect through tissue and artery wall.

The dilator 1340 is shown in a locked configuration with the catheter 1320 configured for improved tracking through a tortuous and often diseased vasculature in acute ischemic stroke. The dilator portion 1360 can include one or more detents on an outer surface of the dilator portion 1360. The detents can be located near a proximal end region and/or a distal end region of the dilator portion 1360. The detents are configured to lock with correspondingly-shaped surface features on the inner surface of the lumen 1323 through which the dilator portion 1360 extends. The dilator 1340 can include a dilator tab 1364 on a proximal end of the proximal spine 1362 of the dilator 1340, which as discussed above can be configured to connect and lock with a corresponding feature on the proximal end region of the catheter spine 1330, for example via one or more detents or other surface features. Thus, the dilator 1340 and the catheter 1320 can have more than a single point of locking connection between them. The proximal spine 1362 of the dilator 1340 can extend between the dilator portion 1360 and the tab 1364 of the dilator 1340. The dilator portion 1360 can be a tubular element as described elsewhere herein that forms a guidewire lumen running a length of the dilator portion 1360

(and an entire length of the distal luminal portion 1322 of the spined catheter 1320). It should be appreciated that the entire dilator 1340 can be tubular element configured to receive a guidewire through the spine 1362 as well as the dilator portion 1360. The proximal end of the dilator portion 1360, i.e., the transition section 1326 between the dilator portion 1360 and the proximal spine 1362, may include a "step up" to smooth the transition between the distal luminal portion 1322 of the catheter 1320 and the dilator portion 1360 of the dilator 1340. The transition section 1326 can incorporate an angled cut such that there is no abrupt step transition from the sheath 1220 inner lumen 1223 to the catheter 1320 inner lumen 1323. Accordingly, the spined aspiration catheter-dilator 1300 may be smooth to the vascular wall it interfaces with.

The proximal spine 1362 of the dilator 1340 may have a similar stiffness and character as the spine 1330 of catheter 1320. More particularly, one or both of the spines 1362, 1330 may be stiff and/or kink resistant. Furthermore, one or both of the spines 1362, 1330 may have a stiffness to allow pushing the distal portions, i.e., the combined distal luminal portion 1322 and dilator portion 1360, through an access sheath or a guide-sheath while producing a very low profile. In an embodiment, one or both of the spines 1362, 1330 includes a stiff wire.

The catheter tab 1334 and the dilator tab 1364 can be removably connected with one another. More particularly, the tabs 1334, 1364 may have a locked configuration and an unlocked configuration. In the locked configuration, the dilator tab 1364 can be engaged with the catheter tab 1334. In the unlocked configuration, the dilator tab 1364 may be disengaged from the catheter tab 1334. The dilator tab 1364 may attach, e.g., click or lock into, the catheter tab 1334 in a fashion as to maintain the relationships of corresponding section of the spined dilator 1340 and the spined catheter 1320 in the locked configuration. Such locking may be achieved by, e.g., using a detent on the dilator tab 1364 that snaps into place within a recess formed in the catheter tab 1334, or vice versa. In some implementations, the spine 1330 of the spined catheter 1320 can run alongside or within a specialized channel of the dilator spine 1362. The channel can be located along a length of the dilator spine 1362 and have a cross-sectional shape that matches a cross-sectional shape of the catheter spine 1330 such that the spine 1330 of the catheter 1320 can be received within the channel and slide smoothly along the channel bi-directionally. Once the spined catheter 1320 and spined dilator 1340 are fixed, the combined system, i.e., the spined aspiration catheter-dilator 1300 may be delivered to a target site, for example through the lumen 223 of the access sheath 220 described elsewhere herein.

Figure 12B:
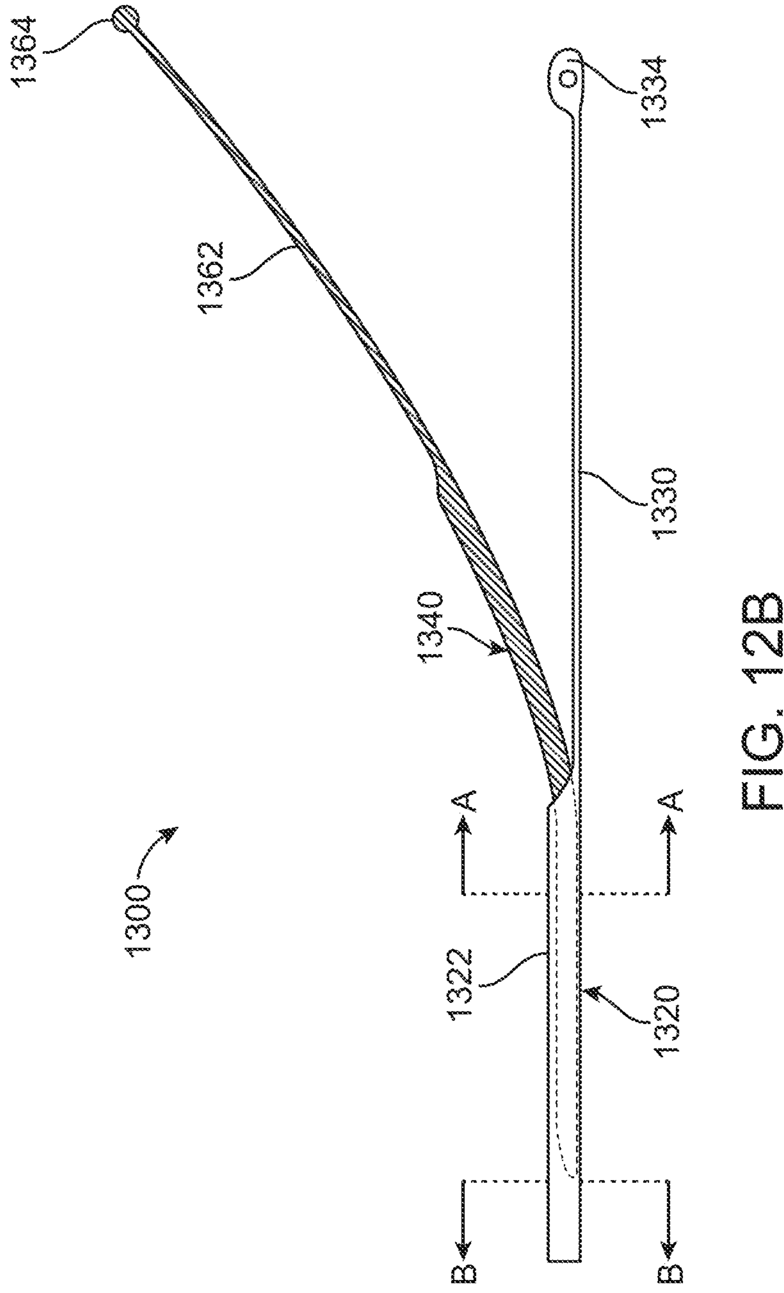
FIG. 12B shows the spined catheter system of FIG. 12A having a spined dilator extending through a lumen of a spined catheter.

Referring to FIG. 12B, a spined aspiration catheter-dilator 1300 having a spined catheter 1320 and a spined dilator 1340 in an unlocked configuration is illustrated in accordance with an embodiment. When the spined aspiration catheter-dilator 1300 is positioned at the target site, as discussed herein, the dilator tab 1364 can be unlocked from the catheter tab 1334. The spined dilator 1340 may be withdrawn and the spined catheter 1320 may be used, e.g., for aspiration or for wire or balloon delivery.

Figure 13:
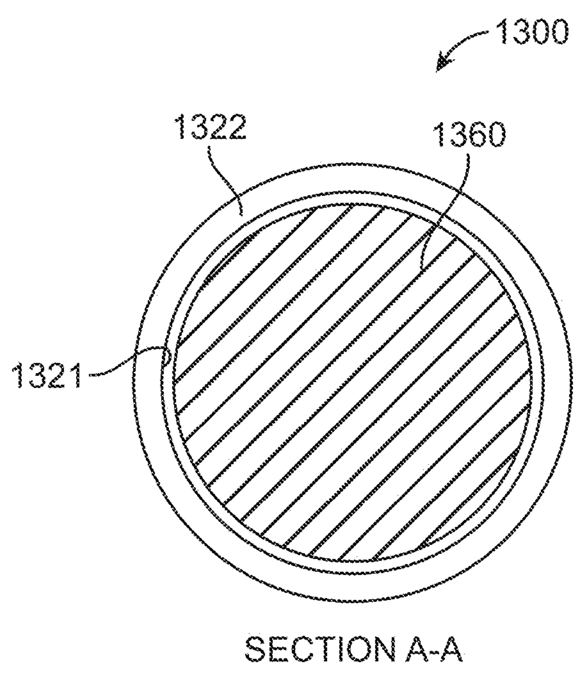
FIG. 13 is a cross-sectional view taken about line A-A of FIG. 12B.

Referring to FIG. 13, a cross-sectional view, taken about line A-A of FIG. 12B, of a spined catheter 1320 coaxially aligned with a spined dilator 1340 is illustrated in accordance with an embodiment. The cross-section illustrates a portion of the catheter-dilator having the dilator portion 1360 received within the aspiration lumen 1323 of distal luminal portion 1322. The lumen 1323 may have an inner diameter in a range up to inches, although a larger or smaller inner diameter is possible (larger or smaller possible). The wall of the distal luminal portion 1322 may resist kinking or ovalizing to provide maximum diameter for aspiration. The dilator portion 1360 may be received in the distal luminal portion 1322 in a slip fit. Thus, in an embodiment, an outer dimension of the dilator portion 1360 may be less than the inner diameter of the distal luminal portion 1322. For example, the lumen 1323 may have a diameter of 0.072 inches and the dilator portion 1360 may have an outer dimension of 0.070 inches.

Figure 14:
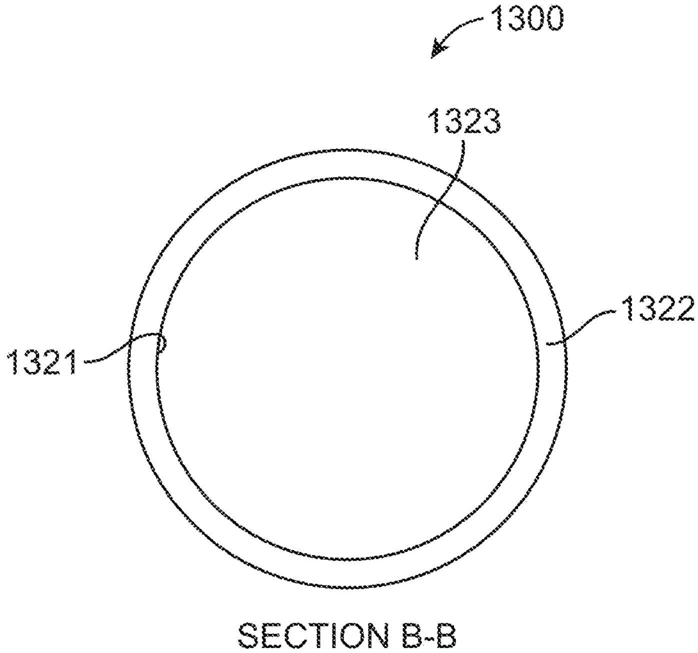
FIG. 14 is a cross-sectional view taken about line B-B of FIG. 12B.

Referring to FIG. 14, a cross-sectional view, taken about line B-B of FIG. 12B, of a spined catheter 1320 after removal of a spined dilator 1340 is illustrated in accordance with an embodiment. The cross-section illustrates the distal luminal portion 1322 after the dilator portion 1360 has been retracted and/or removed. The distal luminal portion 1322 has an inner wall 1321 defining the lumen 1323. The lumen 1323 may be circular, as shown, or may have any other shape. In an embodiment, the effective diameter of the lumen 1323 ranges up to 0.072 inches.

Figure 15A:
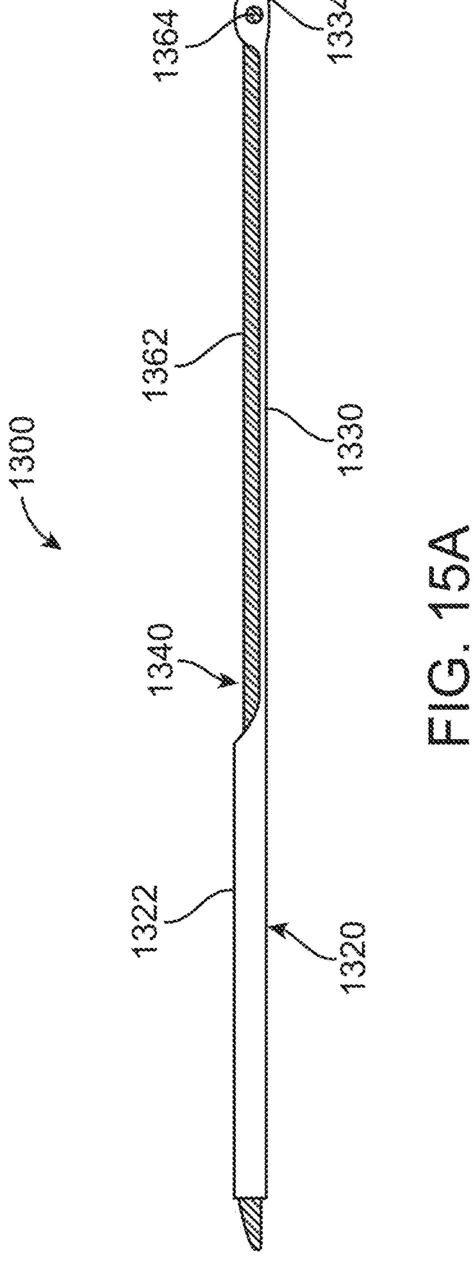
FIG. 15A shows an implementation of a spined aspiration catheter-dilator system having a spined catheter and a spined dilator in a locked configuration.

Referring to FIG. 15A, a spined aspiration catheter-dilator system 1300 having a spined catheter 1320 and a spined dilator 1340 in a locked configuration is illustrated in accordance with an embodiment. In an embodiment, the spine 1330 and dilator 1340 may have an outer dimension that is substantially similar over an entire length. For example, rather than converging to a smaller dimension between the dilator portion 1360 and the dilator spine 1362, the dilator spine 1362 may have a same dimension as the dilator portion 1360. Thus, a catheter-dilator having a substantially same cross-sectional area over at least a majority of its length may be provided. As discussed above, the spine dilator 1340 and the spine catheter 1320 may have corresponding tabs 1334, 1364 that engage in a locked configuration and disengage in an unlocked configuration.

Figure 15B:
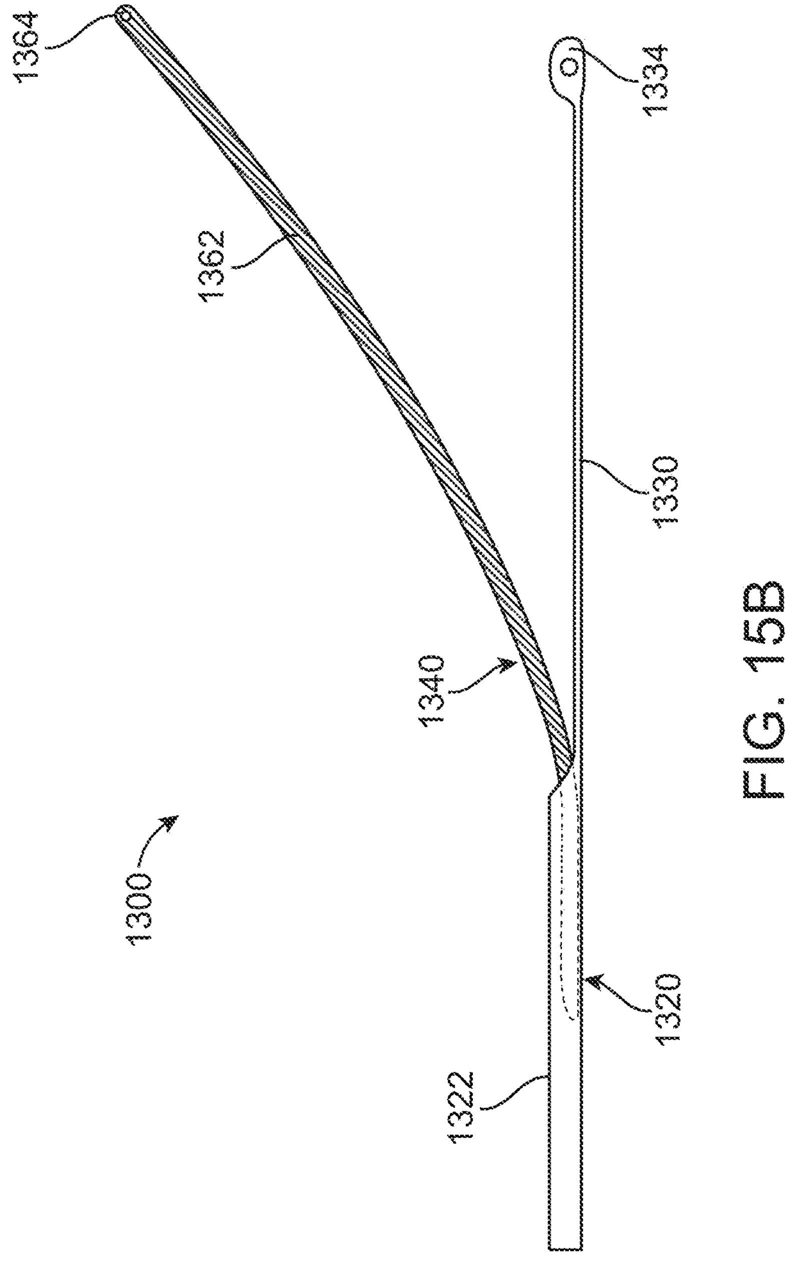
FIG. 15B shows the spined aspiration catheter-dilator system having the spined catheter and the spined dilator in an unlocked configuration.

Referring to FIG. 15B, a spined aspiration catheter-dilator having a spined catheter 1320 and a spined dilator 1340 in an unlocked configuration is illustrated in accordance with an embodiment. The spined dilator 1340 may be removed from the spined catheter 1320 in a manner similar to that described above. In an embodiment, the spined aspiration catheter-dilator may have a similar cross-sectional area over a majority of its length, and thus, the shapes of the spined catheter 1320 and the spined dilator 1340 may be complimentary. For example, the spine 1330 may have a cross-sectional area along an arc, such as a quarter circle, and thus, a cross-sectional area of the dilator spine 1362 may be three quarters of a circle. As such, the spine 1330 may conform to the dilator spine 1362 to provide an overall cross-sectional area of a full circle.

Figure 16:
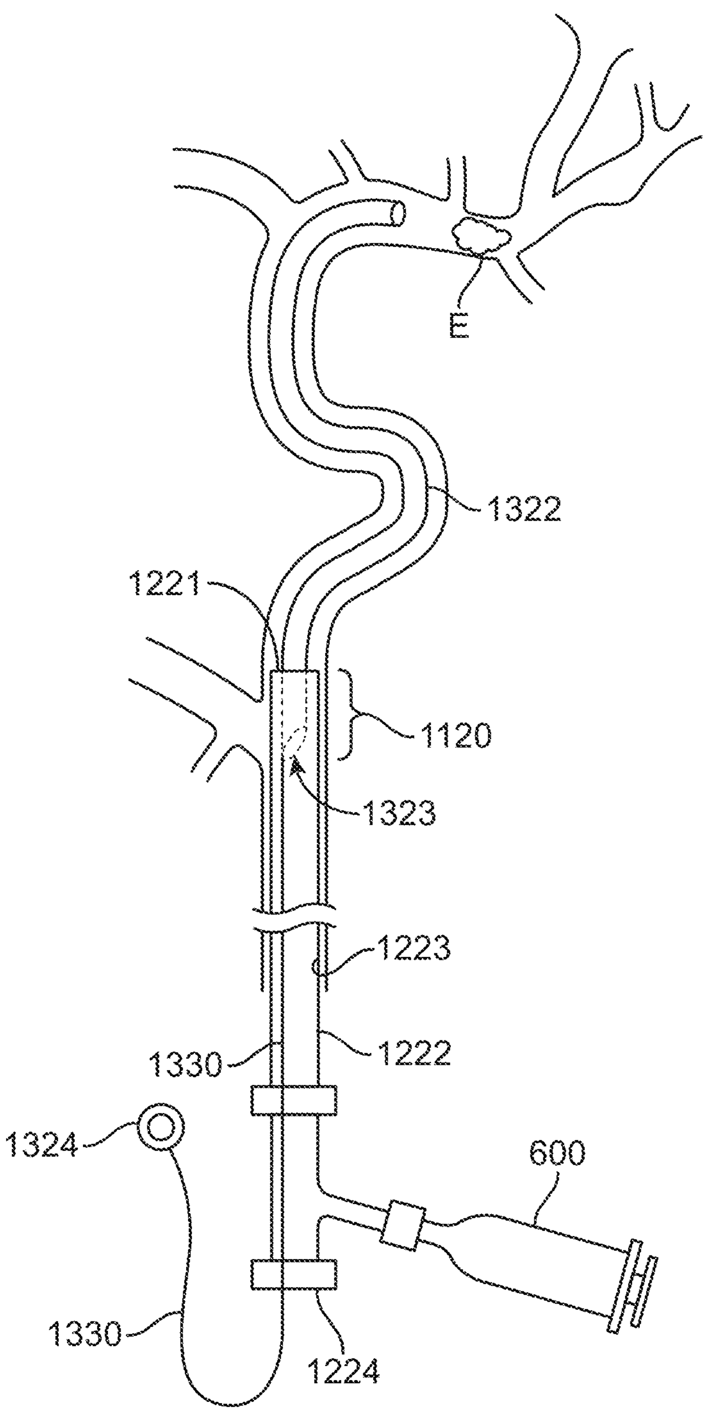
FIG. 16 shows an implementation of a spined catheter system extending distally to an access sheath to treat an embolus in a cerebral vessel.

Referring to FIG. 16, a schematic view of a spined catheter 1320 having a distal luminal portion 1322 having an inner lumen 1323 located in a neurovascular anatomy is illustrated in accordance with an embodiment. Used in conjunction with an access sheath 1220 having a sheath body 1222 and an inner lumen 1232, in an embodiment where the spined catheter 1320 reaches the ICA and the distance to embolus E is consistently felt to be less than 20 cm, one would see that the distal luminal portion 1322 having a length of 25 cm would allow for an overlap region 1120 with the access sheath 1220 to create a seal. The overlap region 1120 may have a length of a few centimeters, and the may vary depending on the distance from the embolus E to the distal end of the distal luminal portion 1322, e.g., depending on how far the spined catheter 1320 is advanced relative to the access sheath 1220.

As described elsewhere herein, the luminal area available for aspiration of the embolus is greater using the spined catheter 1320 as compared to an aspiration system having a conventional large bore catheter in an access sheath. More particularly, the combined volume of the luminal area of the spined catheter 1320 and the luminal area of the access sheath 1220 proximal to the distal luminal portion 1322 is greater than the luminal area of the large bore catheter along the entire length of the system. Thus, the likelihood of removing the embolus in a single aspiration attempt may be increased. More particularly, the stepped up luminal diameter along the spine 1330 may enable a greater aspiration force to be achieved resulting in improved aspiration of the embolus. The stepped up luminal diameter may also increase the annular area available for forward flushing of contrast, saline, or other solutions while devices such as microcatheters or tapered inner members are coaxially positioned in the spined catheter and access sheath. Thus, the ease and ability to perform angiograms during device navigation may be improved.

The disclosed systems may be supplied with ancillary devices that are particularly configured to be used with the system. It should be appreciated that reference to one implementation of an access sheath system or aspiration catheter system is not intended to be limited and that the ancillary devices described herein can be used with any of the systems having any of a variety or combination of features described herein. For example, where an access sheath is described below it should be appreciated that one or more features of any of the access sheaths or access sheath systems described herein can be incorporated. Similarly, where a spined catheter is described below one or more featured of any of the spined catheters or spined catheter systems described herein can be incorporated.

In an implementation, the system includes a microcatheter 400 (see FIG. 1). The microcatheter 400 can be configured to be particularly suited for navigation in the cerebral vasculature. The microcatheter 400 may be used in place of the tapered dilator 340 to help navigate the spined catheter 320 to the desired site. As such, it may include means at the proximal end to lock the spine 330 to the microcatheter 400, so that so that the two components (the spined catheter 320 and the microcatheter 400) may be advanced as a single unit over the guidewire. In some instances the microcatheter 400 is advanced ahead of the catheter 320, to provide support as the catheter 320 is advanced, or to cross the occlusion and perform an angiogram distal to the occlusion. In this case, the length of the microcatheter 400 can be longer than the spined catheter 320 by about 10 to 20 cm. The microcatheter 400 may also be used to deliver a retrievable stent device 500 to the occlusion. In this case, the microcatheter 400 can have an inner diameter suitable for delivery of the retrievable stent device 500, for example, in the range 0.021" to 0.027" and with a PTFE inner liner. The microcatheter 400 can be at least about 5-10 cm longer or at least about 5-20 cm longer than the overall length of the spined catheter 320 to allow the microcatheter 400 to extend beyond the distal end of the aspiration catheter 320 during navigation.

Figure 9:
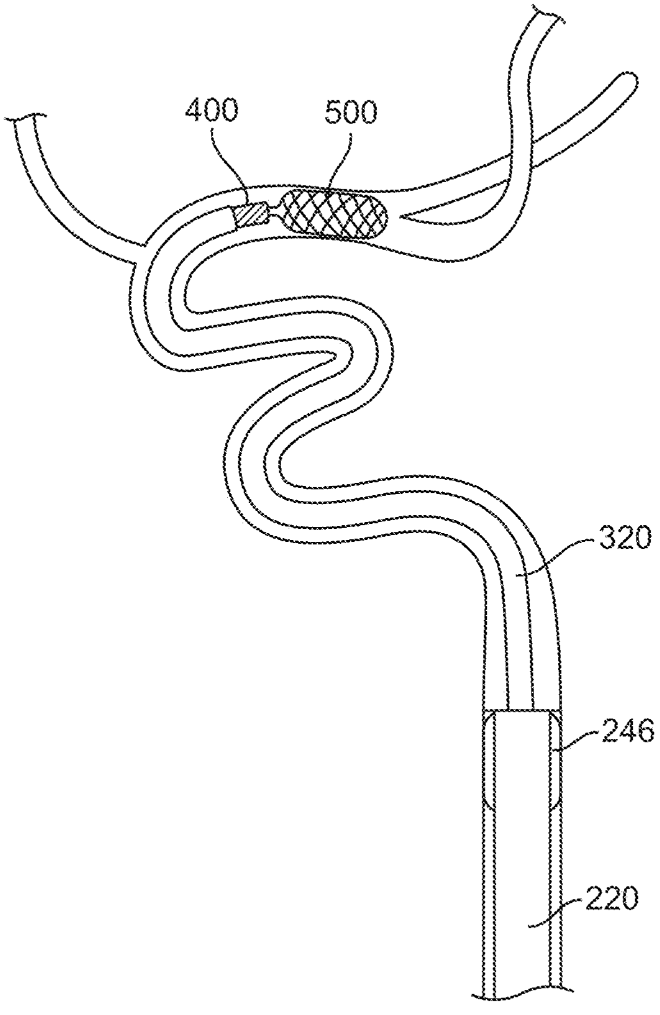
FIG. 9 shows an implementation of a microcatheter and retrievable stent device positioned through a spined catheter.

In an implementation, the system includes a retrievable stent device 500 with a distal expandable section 510, which is sized and configured to be delivered through the microcatheter 400, as shown in FIG. 9. The retrievable stent device 500 may be used in conjunction with the other components of the system to aid in removal of the occlusion. The retrievable stent device 500 may also be used to quickly restore flow to the occluded artery during the thrombectomy procedure. Examples of retrievable stent devices include the Solitaire Revascularization Device (Medtronic) or the Trevo Stentriever (Stryker).

Figure 10A:
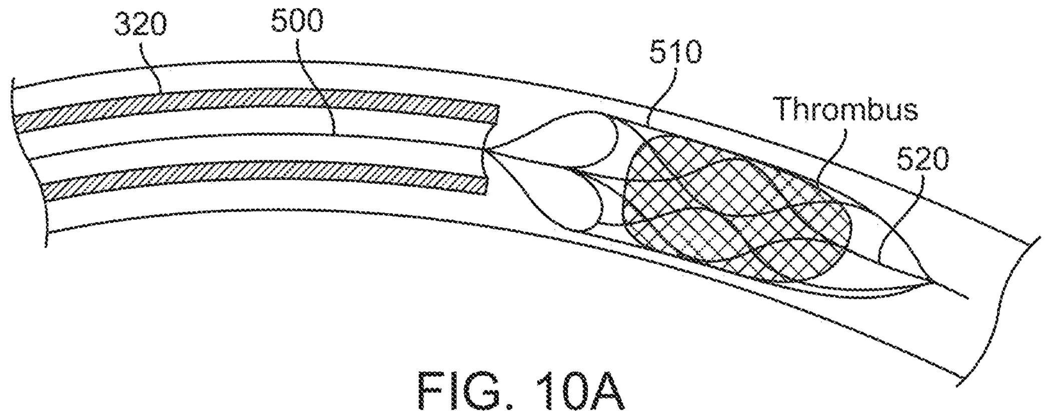
FIGS. 10A-10C show implementations of expandable portions on retrievable stent devices.

In a method of use, the retrievable stent device 500 is used to assist in bringing thrombus into the catheter 320 during an aspiration step, or clearing the catheter 320 that may become clogged during the aspiration step. In an implementation, the retrievable stent device 500 is configured to be particularly suited for performing these functions. For example, as shown in FIG. 10A, the distal end of the expandable portion 510 of the device 500 has multiple struts or elements 520 that come together at the distal tip to close off the distalmost end, such that the device allows blood flow across the device, but captures the thrombus pieces as the device 500 is pulled into the catheter 320, and subsequently through the catheter 320 and out the distal end. Alternately, the distal end 520 is a filter element or a balloon element.

Figure 10B:
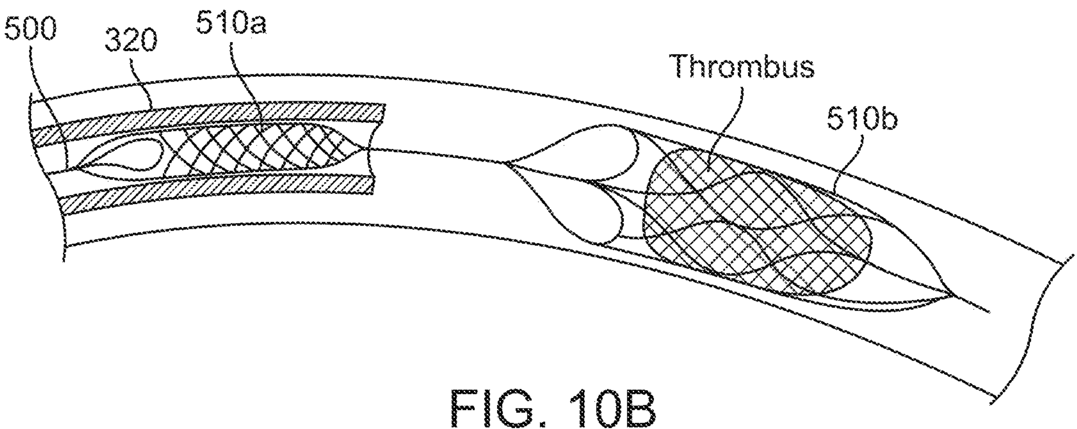
Figure 10C:
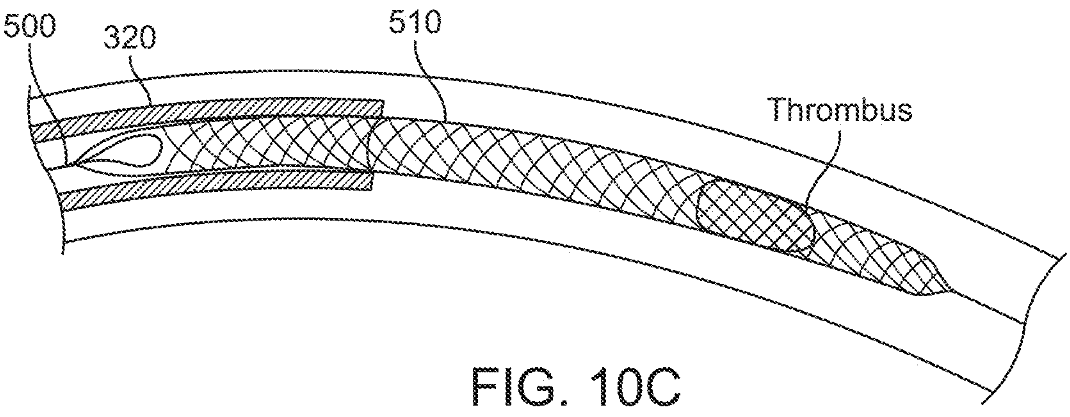

In another example, in FIG. 10B, the retrievable stent device 500 includes two or more segments with one or more proximal segments 510*a* configured to be expanded in the catheter distal inner lumen while one or more distal segments 510*b* are expanded across the occlusion as is done with prior retrievable stent devices. Alternately, as seen in FIG. 10C, the retrievable stent device 500 has a very long expandable portion 510, such that a proximal portion of the expandable portion may be expanded in the catheter distal inner lumen while the distal portion is expanded across the occlusion. In all these implementations, the proximal end of expandable section 510 has minimal structural elements that will allow the expandable section to be pulled easily into the lumen of the catheter 320, and out of the access sheath 320, so as minimize impediment of thrombus aspiration through the device. In these examples, the expandable portion 510 is still engaged with the clot even when the clot is aspirated into the catheter 320, and if the catheter 320 becomes corked, the device 500 is well-positioned to clear the clot when it is pulled back. Once the retrievable stent device 500 has been removed from the luminal portion 322 of the catheter 320, additional aspiration can be applied to the site through the catheter 320 if it is still partially or fully occluded. This step would not be possible if the catheter 320 remained clogged; the catheter would have to be removed and cleared outside the patient before being reinserted for additional aspiration. This configuration of retrievable stent device 500 can be used with either a conventional single lumen aspiration catheter, or a spined aspiration catheter 320.

The implementations of device 500 as shown in FIGS. 10A-10C may be used with known thrombectomy devices and methods to address the issue of catheters clogging during thrombus aspiration.

Figure 3:
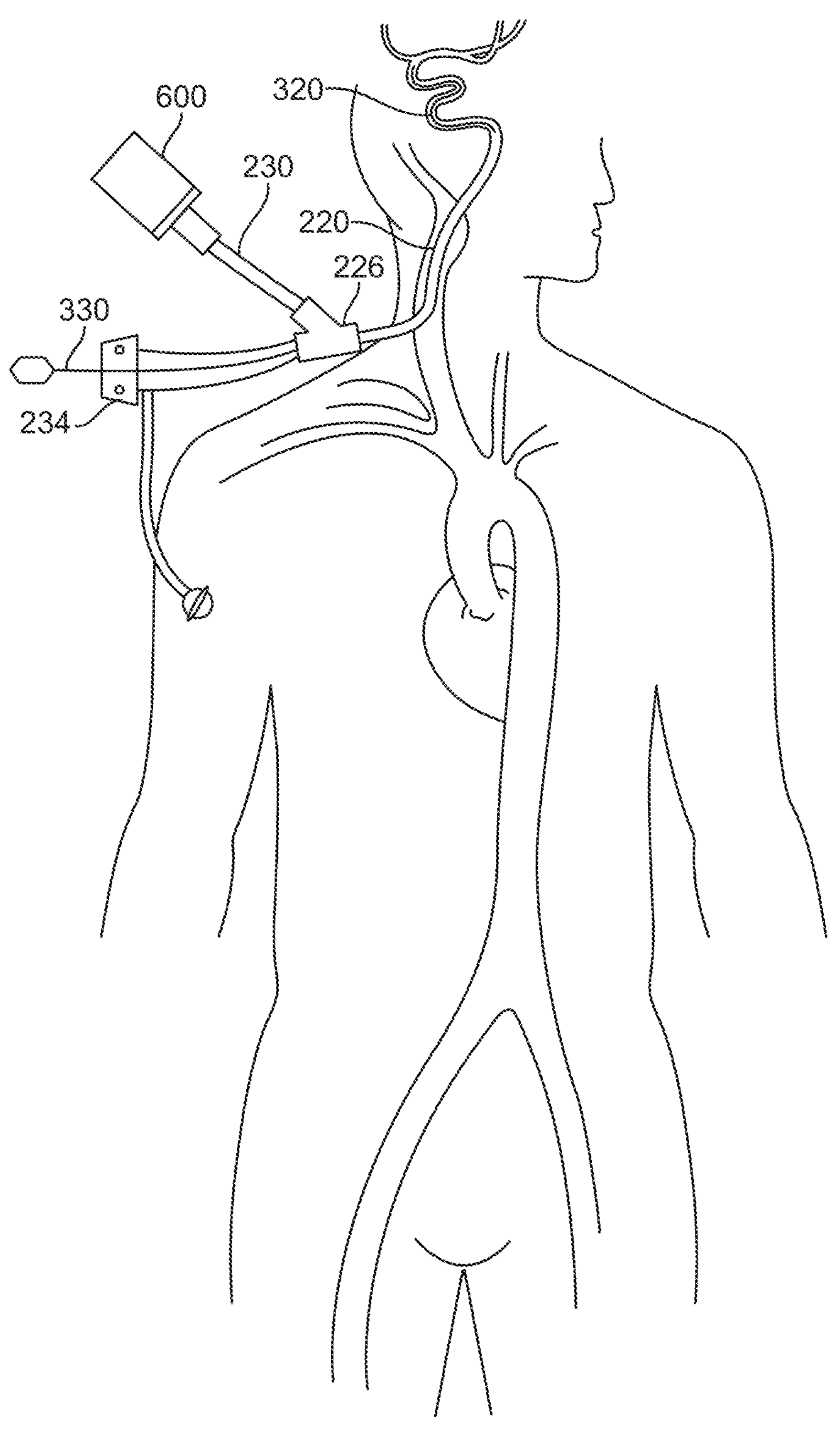
FIG. 3 shows components of the system of FIG. 1 being used via a transcarotid access site.

In an implementation, the system includes an aspiration source 600, as shown in FIG. 2A or FIG. 3. The aspiration source 600 can be attached to the aspiration line 230 on the access sheath 220. Examples of aspiration source 600 include a syringe or an active aspiration pump. The aspiration source 600 may be connected to a delivery location, such as a receptacle. The receptacle and source of aspiration 600 may be separate, such as a mechanical or electromechanical fluid pump whose outlet is connected to a blood collection reservoir or may be combined into a single device such as a syringe or syringe pump. Alternately, the blood collection reservoir is connected to a source of vacuum such as a hospital vacuum line or an air vacuum pump, and is thus the receptacle as well as the source of aspiration. A filter and/or a check valve may be coupled with the aspiration source. The pump may be a positive displacement pump such as a diaphragm or piston pump, a peristaltic pump, centrifugal pump, or other fluid pump mechanism known in the art.

In an implementation, the aspiration source is a variable state or multi-state aspiration source, and includes a mechanism to control the level of aspiration, for example by modifying the vacuum level in the vacuum pump, by modifying the power to the motor of a positive displacement, peristaltic or centrifugal pump, or modifying the syringe pull back speed in the syringe or syringe pump. Alternately, the aspiration rate may be varied by providing an element with variable resistance to flow, for example parallel flow paths that can switch between a high and low flow resistance path, flow orifices or lumens that can be variably opened, or other means to vary flow resistance. In an example, the aspiration source is configured to have two levels of aspiration: a high level of aspiration to be used when the catheter is in contact with the thrombotic material, to aspirate the thrombotic occlusion, and a low level of aspiration to be used during steps in the procedure that are high risk of causing distal emboli, for example crossing the lesion or when flow is restored to the vessel when a retrievable stent device is expanded.

Figure 11:
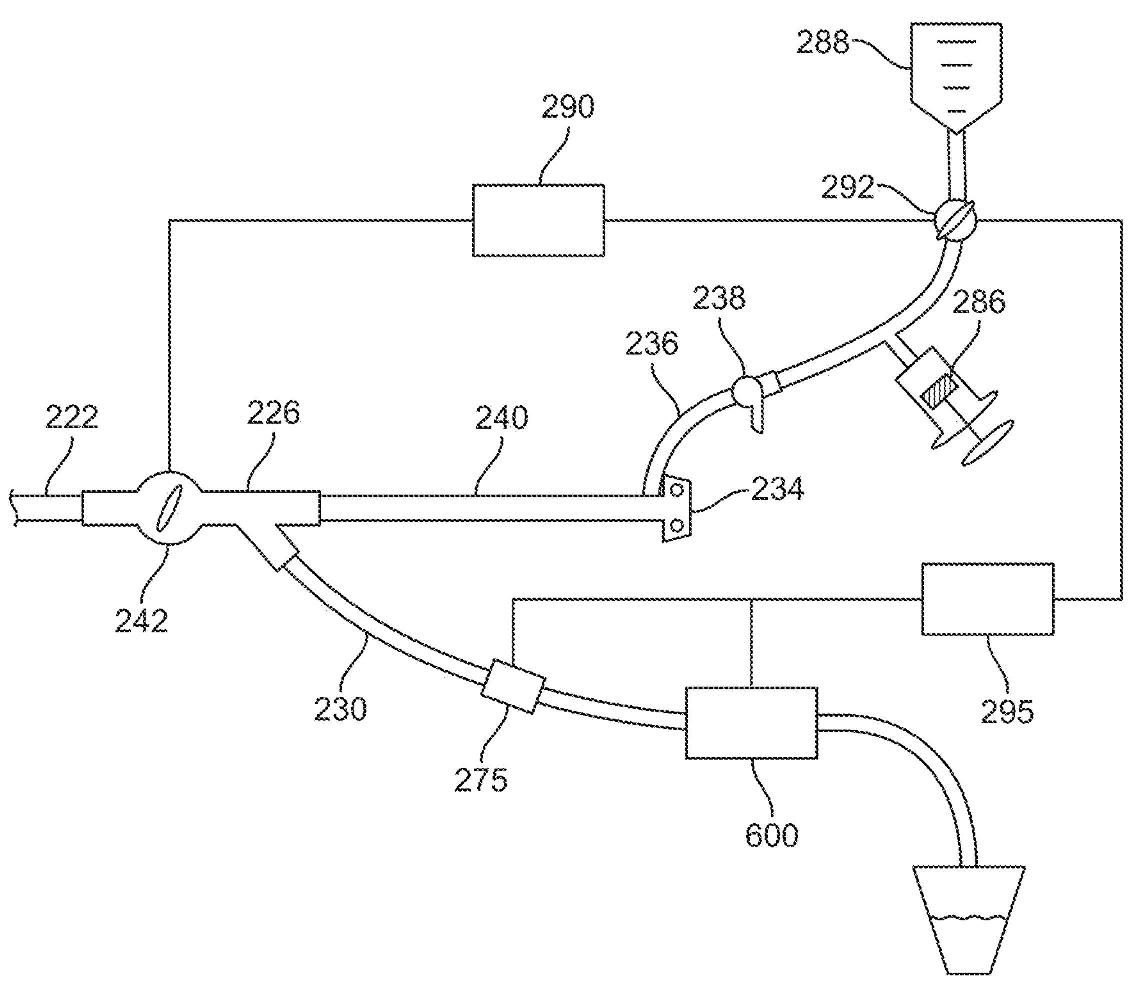
FIG. 11 shows an implementation of an aspiration system for use with the systems described herein.

In another example, as shown in FIG. 11, the aspiration source 600 further includes a flow sensor 275 that senses flow in the aspiration line 230, coupled to a controller that controls the level of aspiration. The aspiration source 600 can increase in aspiration level when the flow rate is slow and decrease when the flow rate is increased. In this manner, the force is greatest when the catheter is clogged or partially clogged, but decreases to a minimal level when there is free flow to ensure protection from distal emboli but limit the volume of aspirated blood. In this manner, the system optimizes the thrombus aspiration while limiting the amount of blood aspirated. Alternately, the aspiration source 600 can include a vacuum gauge. When the flow in the catheter 320 is blocked or restricted the pump creates a higher level of vacuum. In this example the aspiration force may be configured to rise when higher vacuum is detected.

In yet another aspiration source implementation, the aspiration source 600 provides a cyclic level of aspiration force, for example, an aspiration force that cycles between a high level of vacuum to a lower level of vacuum at a set frequency, or from a high level of vacuum to no vacuum, or from a high level of vacuum to a pressure source. A cyclic aspiration mode may provide a jack-hammer type force on the thrombus and increase the ability to aspirate the thrombus through the catheter. The cyclic aspiration force may be enabled through solenoid valves, a programmable pump motor, or the like. In an implementation, cyclic aspiration is applied only when clogged or restricted flow is detected in the aspiration line, either through low flow or high vacuum, as discussed above, and at other times, the aspiration source reverts to a low level of flow, or be turned off. This configuration may be controlled by the user, or controlled automatically via a feedback loop to the aspiration source.

In an implementation, the system includes a mechanism for passive reverse flow that is configured to be connected to the aspiration line on the access sheath. For example, the aspiration line is connected to a lower pressure site such as a central vein, or an external receptacle set to zero or negative pressure.

In an implementation as shown in FIG. 11, the flush line 236 may be connected via stopcock 238 to a syringe 286 that may hold saline fluid or radiopaque contrast. Additionally the flush line 236 may be connected to a flush source 288, for example, a pressurized bag of saline. A valve 292 can control flow from the flush source 288 to the flush line 236. When the valve 292 is opened to the flush line 236 a pressurized source of fluid is provided. In an implementation, the valve 292 is coupled via a mechanical or electromechanical coupler 295 to the aspiration source 600 such that the valve 292 is only open when the aspiration source 600 is on. Alternately, the valve 292 is coupled to a flow sensor 275 in the aspiration line 230, such that the valve 292 is only on when there is flow in the direction towards the aspiration source 600. In these implementations, the flow rate of the flush source 288 is configured to flow just enough to keep the proximal extension 240 clear of blood but not so high as to cause flow to work against the aspiration flow and limit aspiration of thrombus. An advantage of this implementation is that the proximal extension 240 remains clear of blood and any emboli or air that is in the proximal extension 240 is clearly visible. This provides a feedback to the user on when and if to flush the catheter with saline or contrast via syringe 286.

In another implementation, the valve 292 is coupled either mechanically or electromechanically to the valve 242 that connects the sheath body 222 to the proximal portion 240 of the sheath 220. The coupling 290 can be configured such that the valve 292 can only be opened when the valve 242 is closed. This feature allows the proximal extension 240 to be cleared of blood via a flush step, without risk of flushing emboli back through the catheter into the vasculature. The coupling 290 may be configured in one of several ways For example, the coupling 290 may always open the valve 238 when the valve 242 is closed, or the coupling may prevent the valve 238 from opening unless valve 242 is closed but that does not automatically open.

In an implementation, the valve 292 is a variable state valve that allows different levels of flush flow rate. In this example, the valve 292 is configured to allow a slow flush when the aspiration source is on a low setting, a higher level of flush when the aspiration source is on a high setting. In an implementation, the valve allows yet a higher level of flush when the valve 242 is closed. These configurations allow a continuous removal of debris and/or clear visibility of the proximal portion of the access sheath and minimizes the risk of distal emboli or air entering the vasculature during the steps of the procedure. For example, during the step when the distal tip of catheter is being removed from the proximal hemostasis valve 234, any clot that was captured on the tip of the catheter may be liberated when the catheter is pulled through the valve, but with the continuous flush the liberated emboli would be flushed into the aspiration line and not remain in the sheath where it might be re-injected into the vasculature, for example during a contrast injection after the catheter is removed.

Again with respect to FIG. 1, the system 100 may include a kit of multiple devices. In an implementation, the kit includes an access sheath system 200 wherein the access sheath system includes an access sheath, one or more tapered sheath dilators, and one or more sheath guidewires. In another implementation, the system 100 includes an access sheath system 200 and one or more spined catheter systems 300 with one or more inner diameters. In an implementation, the spined catheter system 300 includes a spined aspiration catheter 320 and a tapered dilator 340. In an implementation, the spined catheter system 300 also includes a catheter clearing tool 350. In yet another implementation, the system 100 includes an access sheath system 200, a tapered catheter system 300, a microcatheter 400, and a retrievable stent device 500.

In an implementation configured for transcarotid access, the kit includes an access sheath 220, wherein the insertable sheath body 222 length is about 23 cm, the proximal extension 240 is about 22 cm, the connector 226 is about 7 cm and the proximal hemostasis valve 234 is about 5 cm, for an overall access sheath length of about 57 cm. In an implementation, the kit also includes a spined aspiration catheter 320 wherein the catheter distal luminal portion 322 is about 20 cm, the transition section 326 is about 2-4 cm, and the spine section 330 is about 65 cm, for an overall spined catheter length of about 88 cm. In another implementation, the kit also includes a tapered dilator 340 with a working length of 93 cm. In another implementation, the kit also includes a microcatheter 400 with a working length of about 198 cm and a retrievable stent device 500 with an overall length of 128 cm.

In an implementation configured for transfemoral access, the kit includes an access sheath system 220, wherein the insertable sheath body 222 length is about 90 cm, the proximal extension 240 is about 22 cm, the connector 226 is about 7 cm and the proximal hemostasis valve 234 is about 5 cm, for an overall access sheath length of about 124 cm. The proximal portion of the access sheath may be a removable proximal portion 280. In an implementation, the kit also includes a spined aspiration catheter 320, wherein the catheter distal luminal portion 322 is about 20 cm, the transition section 326 is about 2-4 cm, the spine section 330 is about 132 cm, for an overall spined catheter length of about 155 cm. In another implementation, the kit also includes a tapered dilator 340 with a working length of 160 cm. In another implementation, the kit also includes a microcatheter 400 with a working length of about 165 cm and a retrievable stent device 500 with an overall length of 195 cm.

In another implementation, the kit includes an access sheath 220 with a removable proximal portion 280, and a single lumen aspiration catheter. In another implementation, the kit includes only the proximal portion 280 that can be attached to any introducer sheath suitable for the procedure. In this implementation, the kit may also include a spined aspiration catheter 320 or a single lumen aspiration catheter.

In any of these implementations, the kit may also include an aspiration source, for example a pump, an attachment to a vacuum pump, a syringe, a syringe that is attachable to a syringe pump, or the like. The kit may also include means for automatic flushing, for example coupling means 290 or 292.

As described elsewhere herein, it should be appreciated that reference to one implementation of an access sheath system or catheter system is not intended to be limited and that the kits described herein can incorporate any of the systems and/or ancillary devices described herein as having any of a variety of features. For example, where an access sheath is described as being a part of a kit it should be appreciated that one or more features of any of the access sheaths or access sheath systems described herein can be incorporated. Similarly, where a spined catheter is described as being part of a kit one or more featured of any of the spined catheters or spined catheter systems described herein can be incorporated.

FIGS. 2A and 3 illustrates methods of use. As shown in FIG. 2A, an access sheath 220 is inserted using standard vascular access sheath into the femoral artery, and advanced until the sheath tip is positioned at a site as distal as safely possible in the internal or common carotid artery. In FIG. 3, the access sheath 220 is inserted directly into the common carotid artery, and advanced until the sheath tip is positioned at a site as distal as safely possible in the internal carotid artery. In either scenario, the sheath may be advanced initially to the common carotid artery or proximal internal carotid artery, and then the dilator and is exchanged for a softer dilator before advancing the sheath more distally into the internal carotid artery. The sheath is then secured to the patient using a suture through the eyelet on the sheath connector. The sheath aspiration line 230 is connected to an aspiration source 600 such as a syringe or aspiration pump. The sheath aspiration line may also be connected via a stopcock or stopcock manifold to a forward flush line (such as a pressurized saline bag).

Once the sheath tip is positioned at the desired location, it is secured to the patient. A spined catheter, tapered dilator, and guidewire are pre-assembled in a co-axial configuration and introduced through the sheath proximal hemostasis valve into the carotid artery. The spined aspiration catheter 320 is advanced through access sheath and positioned until the distal tip is at the treatment site. The devices are advanced using standard interventional techniques until the distal catheter tip is at the proximal face of the occlusion. A mark 332 on the spine 330 ensures that there is still an overlap region 120 between the distal luminal portion 322 of the catheter and the access sheath body 222. At this point, the tapered dilator 340 and guidewire can be removed. In an alternate implementation, a microcatheter 400 is used in place of the tapered dilator 340 to help navigate the catheter 320 to the occlusion. During the procedure, the forward flush is opened to the aspiration lumen to keep the lumen clear before or between periods of aspiration. At any point during device navigation, aspiration may be initiated from the aspiration source 600 at a level suitable for distal embolic protection, for example when the guidewire or microcatheter 400 is crossing the occlusion.

Once the distal tip of the spined aspiration catheter 320 is at the face of the clot, aspiration is initiated at a level suitable for aspiration thrombectomy, which is a higher level than for distal embolic protection. The catheter 320 may remain in aspiration mode against the clot for some period of time, as deemed suitable by the user. Depending on the results of the aspiration thrombectomy maneuver (as observed by flow though the aspiration line and/or resistance to backwards force on the spine of the catheter), the user may determine that the clot has been completely aspirated, or if not, the user may choose to move the catheter 320 back and forth to aspirate the clot in situ, or to slowly retract the catheter 320 into the sheath 220. If flow is restored to the artery via aspiration of the clot through the catheter 320 and sheath 220, a final angiogram may be performed and the catheter 320 can be retracted. If however, thrombus occludes the catheter tip and cannot be removed, the catheter 320 is pulled back, with some or all of the occlusion attached through suction force to the tip of the catheter 320.

In the latter scenario, aspiration is maintained at the tip of the catheter 320 the entire time the catheter 320 is being pulled into the access sheath 220. Once the catheter 320 has been completely retracted into the access sheath 220, the catheter 320 can be quickly removed from the sheath body 222 while aspiration is maintained on the sheath 220. It should be appreciated that the catheter 320 may be withdrawn into the sheath body 222 after extending through the distal opening 219 at the distal tip of the sheath body 222. Alternatively, the catheter 320 may be extending through a side opening 219 near a distal end region of the sheath body 222 such that withdrawal of the catheter 320 into the sheath body 220 occurs through this side opening 219. At some time during catheter retraction, depending on if the catheter 320 is clogged with occlusive material, the aspiration level may be changed from a high level desirable for aspiration thrombectomy to a lower level desirable for distal embolic protection. By providing the ability to maintain aspiration continuously from either the catheter tip or the sheath tip or the sheath distal region, and providing the means to change aspiration levels and maintain asp, the procedure optimizes the ability to aspiration clot while minimizing distal emboli and minimizing blood loss from aspiration. If desired, aspiration may also be initiated at the flush line 236 of the proximal valve 234, to reduce chance of distal embolization during removal of the catheter tip with possibly adhered clot through the proximal valve 234.

The spined aspiration catheter 320 may be removed completely from the proximal hemostasis valve 234 of the sheath 220. Alternately, if the access sheath 220 has a proximal extension 240, the distal luminal portion 322 may be pulled into the proximal extension portion 240. In the latter scenario, once pulled in, the catheter 320 and sheath 220 may be flushed to remove potential embolic material without removing the catheter 320 completely from the sheath 220. A vigorous flush from the proximal valve flush line 236 simultaneous with aspiration from the aspiration line 230 creates a flush environment for the catheter 320 and sheath 220. If desired, a catheter clearing tool 350 may be inserted into the sheath proximal valve 234 and used at this time to clear the inner lumen 323 of the catheter 320. If the access sheath 220 has a connector valve 242, the proximal portion 240 may be closed off from the sheath body 222 during this stage, so that there is no risk of flushing embolic material into the sheath body 222 and thence into the artery.

Alternately, the valve 242 may be closed off and aspiration paused while the proximal valve 242 is opened or removed and the catheter 320 is completely removed from the sheath 220. Closing the valve 242 limits the blood loss from the sheath 220 as the catheter 320 is removed. The catheter 320 may then be flushed onto the table or into a bowl or other receptacle, using the cleaning tool 350. The proximal extension portion 240 may also be flushed by providing a flush source 288 from the proximal valve flush line 236 simultaneous with aspiration from the aspiration line 230, or by opening a side port on the aspiration line 230 to flush to the table or into a bowl or other receptacle. If desired, an angiogram may be performed to assess flow through the treated artery. If the procedure dictates, the catheter 320 or another catheter may be re-advanced as above over a guidewire and tapered dilator 340 or microcatheter 400 to the site of the occlusion to attempt another aspiration thrombectomy step. The flushing of the catheters and proximal extension portion 240 of the access sheath 220 minimizing the risk of distal emboli during these subsequent steps.

In another exemplary method, a retrievable stent device 500 can be used in conjunction with aspiration to remove the thrombotic occlusion. FIG. 9 illustrates this method of use through either a transcarotid or transfemoral access site. In this scenario, the access sheath 220 can be positioned as above and advanced until the sheath tip is positioned at a site as distal as safely possible in the internal carotid artery. The spined aspiration catheter 320 can be then pre-loaded onto a microcatheter 400 and guidewire, and the co-axial assembly can be introduced via the access sheath 220 into the carotid artery and advanced into the cerebral vasculature. The microcatheter 400 and guidewire can be advanced across occlusion. The tip of the spined aspiration catheter 320 can be advanced as distal as possible but proximal to the clot.

At this point, the guidewire can be removed and the retrievable stent device 500 inserted through the microcatheter 400 until it too is positioned across the occlusion. The microcatheter 400 can be pulled back to deploy the stent. At any point during device navigation, aspiration may be initiated from the aspiration source at a level suitable for distal embolic protection, for example when the guidewire or microcatheter 400 is crossing the occlusion, or prior to stent deployment. By having aspiration initiated before stent deployment, any emboli that was liberated while crossing the lesion is not carried downstream on restoration of flow in the artery, but is rather captured into the catheter tip. While the retrievable stent device 500 is deployed, aspiration may be maintained. It is typically deployed for several minutes before retraction of the stent is attempted, to maximize the engagement of the stent struts to the occlusion. Then, the retrievable stent device 500 can be pulled into the spined catheter 320 and continued to be retracted until it has been completely removed from the proximal valve of the access sheath 220.

Alternately, the stent device 500 can be pulled into the distal portion of the spined catheter 320, and the stent device 500 and spined catheter 320 can be pulled back together out of the access sheath 220. Aspiration may be increased to a higher level during stent and/or catheter retraction steps, to optimize aspiration of clot and minimize distal emboli. If the access sheath 220 has a proximal extension 240 with a valve on the connector, the device 500 can be pulled into the proximal extension 240 and the valve closed, and then the proximal hemostasis valve 234 may be opened widely and the stent device 500 or the stent device/spined catheter combination may be pulled out. The proximal extension section 240 may then be flushed via the valve flush line 236 and the aspiration line 230 before the same or alternate devices are reinserted for another thrombectomy attempt, if the procedure dictates.

Alternately after placement of an aspiration catheter 320, a long or segmented stent retriever 500 can be positioned as above with a microcatheter 400 such that part of the expandable portion 510 is across the thrombus and part is in the distal segment 322 of the catheter 320, and then expanded. After the expandable portion 510 is expanded aspiration can be initiated so that thrombus either is suctioned completely out of the vessel and catheter 320 into the aspiration source 600, or is suctioned into the distal tip and/or distal lumen 323 of the catheter 320. At that point, the long or segmented stent retriever 500 can be carefully pulled into the catheter 320, while maintaining aspiration. During this time clot that has been clogging the catheter 320 and/or debris that is liberated during this step should be aspirated into the catheter 320. Complete removal of the stent retrieval device 500 from the working channel 323 of the catheter 320 should free up the lumen 323 from occlusive material.

In any of these scenarios, the aspiration source may be a variable or multi-state aspiration source that is configured to maximize the aspiration force on the thrombotic occlusion while minimizing blood loss during periods of free flow in the catheter.

In another exemplary method, the access sheath 220 has an occlusion balloon 246. As seen in FIG. 7, the balloon 246 may be inflated during steps of the procedure that are high risk for distal emboli, for example retraction of the stent device 500 or the spined catheter 320 with adhered clot. The balloon 246 has the effect of stopping antegrade flow and increasing the force of aspiration in the carotid artery, thus increasing the aspiration of clot and reducing the risk of distal emboli.

In another exemplary method, the access sheath 220 has an expandable distal tip. In this method, the distal tip may be expanded sometime after the access sheath tip has been positioned at the desired site, but before retraction of the spined catheter 320 into the access sheath 220. This method would reduce the chance of distal emboli caused by the release of clot that was adhered to the distal tip of the spined catheter 320, as the distal tip is pulled into the tip of the sheath 220. Instead, the access sheath tip that is expanded or flared out acts as a funnel to capture the entire clot.

Figure 12C:
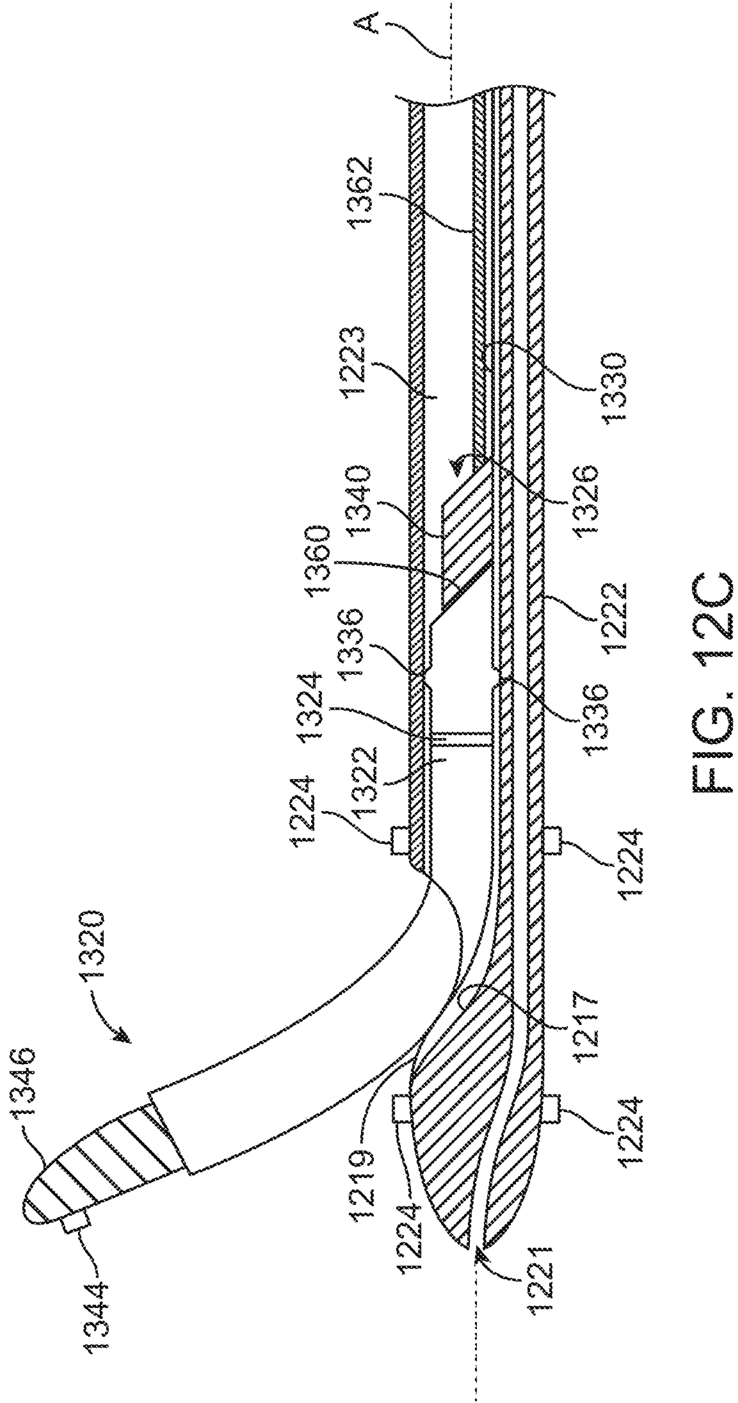
FIG. 12C shows the spined catheter system of FIG. 12A extended through a side opening of an implementation of an access sheath.

In another exemplary method and as discussed briefly above, the access sheath 1220 has a side opening 1219 (best shown in FIG. 12C). In this method, the spined catheter 1320 having a spined dilator 1340 extending through lumen 1323 of the distal luminal portion 1322 of the catheter 1320 can be advanced distally through the lumen 1223 of the access sheath 1220 towards the distal end region of the sheath body 1222. The distal tip of the distal luminal portion 1322 of the spined catheter 1320 (which may having the spined dilator extending through the distal luminal portion 1322 and forming a distal-most end to the catheter system) may exit the lumen 1223 via the side opening 1219 and then be further advanced distally beyond the distal tip of the access sheath 1220. A ramp feature 1217 or other internal feature can be incorporated at a distal end region of the lumen 1223 to provide a surface against which the tip of the dilator can be deflected to guide the catheter 1320 away from a longitudinal axis A of the lumen 1223 of the sheath body 1222 towards the side opening 1219 to achieve a smooth transition or exit from the lumen 1223. The distal tip 1346 of the dilator 1340 can abut against the ramp feature 1217 and be directed at a slight angulation away from the longitudinal axis of the sheath body 1222 towards the side opening 1219. As described elsewhere herein, the sheath body 1222 and thus the side opening 1219 can be rotated around the longitudinal axis A such that the one or more side openings 1219 are positioned to allow for distal extension of the catheter 1320 from the side openings 1219 in a desired direction relative to the longitudinal axis A of the sheath 1220. This will often be dictated by the anatomy encountered by the operator. Also as mentioned elsewhere herein, an overlap region 1120 is formed between the distal luminal portion 1322 of the catheter and the access sheath body 1222. A sealing element 1336 can be positioned on the external surface of the distal luminal portion 1322, for example, near a proximal end region of the distal luminal portion 1322 and may be located within the overlap region 1120. The seal formed can allow for full transmission of aspiration force through the contiguous lumen formed by the lumen 1323 of the luminal portion 1322 and the lumen 1223 of the access sheath body 1222 upon withdrawal of the dilator 1340 from the lumen 1323 of the luminal portion 1322.

In another exemplary method, the aspiration source 600 is connected to a blood collection reservoir that maintains the integrity of the blood in such a way that the blood can be safely returned to the patient at the conclusion of the thrombectomy portion of the procedure, either directly or through subsequent treatment of the blood such as cell washing and/or blood filtration. In another exemplary method, the aspiration source is connected to a blood shunt that is connected in turn to a device such as a venous sheath or a venous return catheter that enables blood to be returned to the patient during the procedure and not requiring a blood reservoir. In another exemplary method, the blood is collected in a reservoir and subsequently discarded at the end of the procedure.

In another exemplary method, the access sheath 1220 is delivered as described elsewhere herein from a femoral insertion site to a right or left subclavian artery or an external carotid artery. The access sheath 1220 may be delivered to a carina of a bifurcation between a target vessel having the embolus, such as the internal carotid artery (ICA), and another vessel, such as the external carotid artery (ECA). Once the access sheath 1220 is in position a working device such as a splined aspiration catheter 1320 can be delivered through the lumen 1223 of the access sheath 1220 into the target vessel. The lumen 1223 of the access sheath 1220 and the lumen 1323 of the catheter 1320 are contiguous and form a stepped up diameter for aspiration as described elsewhere herein. An overlap region 1120 is maintained between the catheter 1320 extending distally from the lumen 1223 of the access sheath 1220. It should be appreciated that the catheter 1320 can extend distally from the lumen 1223 of the access sheath 1220 through an opening 1221 at the distal tip of the access sheath 1220 or a side opening 1119 near the distal region of the access sheath 1220. The body 1222 of the access sheath 1220 may be oriented to provide optimum placement of the side opening 1119 relative to the anatomy. The overlap region 1120 between the distal luminal portion 1322 of the catheter 1320 and the access sheath body 1222 can create a seal and allow for full transmission of aspirating force through the contiguous lumen formed by the lumen 1323 of the luminal portion 1322 and the lumen 1223 of the access sheath body 1222, as well as providing a seal for delivery of fluids to the target vessel such as angiographic contrast injection, saline, one or more drugs or other materials directly into the neurovascular anatomy. The spined aspiration catheter 1320 can create a more powerful aspiration force by allowing for the working lumen 1223 of the access sheath 1220 to provide a majority of the aspiration column. As described elsewhere herein, the dimension of the lumen 1323 of the distal luminal portion 1322 of the aspiration catheter 1320 may be less than the diameter of the lumen 1223 of the access sheath 1220, which is reduced only by a diameter of the spine 1330 extending therethrough. The increased diameter of the lumen can create a larger aspiration column than, e.g., an aspiration column of a large bore catheter having a similar overall length. The spined aspiration catheter 1320 may also be used as a supportive delivery catheter, for example, where the operator wants to reach the petrous carotid or other hard to reach landmarks within the cerebral vasculature. More particularly, after delivering the spined aspiration catheter 1320 into the target vessel through the working lumen 1223 of the access sheath 1220, a secondary working device such as a guidewire, microcatheter, stent retriever, etc. may be delivered through the lumen 1323 into a more distal anatomy to perform other procedural operations as described elsewhere herein.

While this specification contains many specifics, these should not be construed as limitations on the scope of an invention that is claimed or of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Therefore the spirit and scope of the appended claims should not be limited to the description of the implementations contained herein.

What is claimed is:

1. An intravascular access system for facilitation of intraluminal medical procedures within a neurovasculature, the system comprising:
an inner catheter comprising:
a flexible elongate body comprising a single lumen extending from a proximal opening near a proximal end of the flexible elongate body to a single distal opening at a distal end of the flexible elongate body, wherein a length of the flexible elongate body between the proximal opening and the distal opening is sized to position the distal opening within a cerebral artery that is distal to a petrous portion of an internal carotid artery while the proximal opening remains positioned outside a patient's body,
wherein the flexible elongate body comprises a plurality of regions, wherein one of the plurality of regions is a tapered region, wherein a proximal end of the tapered region is connected to a cylindrical region;
at least one marker disposed relative to the tapered region to identify the proximal end of the tapered region; and
an outer catheter comprising:
a catheter lumen extending between a proximal opening and a distal opening at a distal end of the outer catheter, wherein the inner catheter is sized to insert through and be removed entirely from the catheter lumen of the outer catheter, and wherein the tapered region of the flexible elongate body is more flexible than the distal end of the outer catheter; and
at least one locking feature designed to be coupled to the proximal end of the flexible elongate body and coupled to a proximal end of the outer catheter,
wherein, when assembled during advancement through the petrous portion of the internal carotid artery to a treatment site within the cerebral artery, at least a portion of the cylindrical region of the inner catheter is located within the catheter lumen of the outer catheter and at least a portion of the tapered region is located distal to the distal opening of the outer catheter, and the inner catheter is locked with the outer catheter by the at least one locking feature.

2. The access system of claim 1, wherein the plurality of regions of the flexible elongate body comprise unreinforced polymer.

3. The access system of claim 1, wherein the at least one locking feature is configured to reversibly engage with the outer catheter when the inner catheter and the outer catheter are assembled.

4. The access system of claim 1, wherein the at least one locking feature includes a gripping feature.

5. The access system of claim 1, wherein the at least one marker is tungsten, platinum or tantalum-impregnated polymer.

6. The access system of claim 1, further comprising a guidewire sized to extend through the single distal opening of the flexible elongate body.

7. The access system of claim 6, wherein the flexible elongate body forms a smooth transition in flexibility between a flexibility of the distal end of the outer catheter to a flexibility of the guidewire extending outside the single distal opening of the flexible elongate body.

8. The access system of claim 1, wherein the at least one locking feature is configured to be placed in a locked configuration to maintain a fixed position between the outer catheter and the inner catheter and in an unlocked configuration to allow for removal of the inner catheter from the catheter lumen.

9. The access system of claim 1, wherein the flexible elongate body has an inner diameter of between 0.020" and about 0.024" and is sized to receive a guidewire, wherein the guidewire has an outer diameter of between 0.014" and about 0.018".

10. The access system of claim 1, wherein the tapered region tapers over a length that is between 1.5 cm and 3 cm.

11. The access system of claim 1, wherein an outer diameter of the cylindrical region is about 0.003"-0.010" smaller than an inner diameter of the catheter lumen.

12. The access system of claim 11, wherein the inner diameter of the catheter lumen is about 0.040"-0.088".

13. The access system of claim 1, further comprising a guide sheath comprising a working lumen extending between a proximal end region of the guide sheath and a distal end region of the guide sheath, the distal end region of the guide sheath having at least one opening in communication with the working lumen of the guide sheath.

14. The access system of claim 1, wherein the outer catheter is an aspiration catheter and the system further comprises an aspiration pump to apply negative pressure through the aspiration catheter upon removal of the inner catheter from the catheter lumen to perform aspiration thrombectomy.

* * * * *